US 8,076,295 B2

(12) United States Patent
Hulvat et al.

(10) Patent No.: US 8,076,295 B2
(45) Date of Patent: Dec. 13, 2011

(54) PEPTIDE AMPHIPHILES HAVING IMPROVED SOLUBILITY AND METHODS OF USING SAME

(75) Inventors: James F. Hulvat, Chicago, IL (US); Mustafa O. Guler, Chicago, IL (US)

(73) Assignee: Nanotope, Inc., Skokie, IL (US)

( * ) Notice: Subject to any disclaimer, the term of this patent is extended or adjusted under 35 U.S.C. 154(b) by 309 days.

(21) Appl. No.: 12/104,407

(22) Filed: Apr. 16, 2008

(65) Prior Publication Data

US 2009/0042804 A1     Feb. 12, 2009

Related U.S. Application Data

(60) Provisional application No. 60/912,289, filed on Apr. 17, 2007.

(51) Int. Cl.
*A61K 38/10* (2006.01)
*C07K 1/113* (2006.01)
*C07K 7/08* (2006.01)
*C12N 11/08* (2006.01)

(52) U.S. Cl. ..... 514/17.7; 435/397; 514/19.1; 514/21.5; 530/327; 530/334; 530/345

(58) Field of Classification Search .................. None
See application file for complete search history.

(56) References Cited

U.S. PATENT DOCUMENTS

| | | | |
|---|---|---|---|
| 4,554,101 A | 11/1985 | Hopp | |
| 4,930,077 A | 5/1990 | Fan | |
| 5,114,713 A * | 5/1992 | Sinigaglia | 424/191.1 |
| 5,130,123 A | 7/1992 | Reynolds et al. | |
| 5,208,111 A | 5/1993 | Decher et al. | |
| 5,223,409 A | 6/1993 | Ladner et al. | |
| 5,622,699 A | 4/1997 | Ruoslahti et al. | |
| 5,670,483 A | 9/1997 | Zhang et al. | |
| 5,733,868 A | 3/1998 | Peterson et al. | |
| 5,843,780 A | 12/1998 | Thomson | |
| 5,853,830 A | 12/1998 | McCaulley et al. | |
| 5,871,767 A | 2/1999 | Dionne et al. | |
| 5,955,343 A | 9/1999 | Holmes et al. | |
| 5,993,541 A | 11/1999 | Litvin et al. | |
| 6,051,272 A | 4/2000 | Stupp et al. | |
| 6,085,206 A | 7/2000 | Domini et al. | |
| 6,096,863 A | 8/2000 | Fields et al. | |
| 6,114,038 A | 9/2000 | Castro et al. | |

(Continued)

FOREIGN PATENT DOCUMENTS

CN     2007-483492     2/2007

(Continued)

OTHER PUBLICATIONS

Sampson et al. The Synthesis of 'Difficult' Peptides Using 2-Hydroxy-4-Methoxybenzyl or Pseudoproline Amino Acid Building Blocks . . . Journal of Peptide Science. 1999, vol. 5, pp. 403-409.*

(Continued)

*Primary Examiner* — Jeffrey E Russel

(57) ABSTRACT

Disclosed herein are novel peptide amphiphile molecules and compositions discovered to possess improved solubility in aqueous buffers which, in turn, facilitates purification required for pharmaceutical applications, particularly for in vivo administration to human patients. In addition, gels of such peptide amphiphile compositions are shown herein to possess unexpectedly superior gelation kinetics and rheological properties, including an increased mechanical stiffness, which better mimics the mechanical properties of natural central nervous system tissues.

28 Claims, 6 Drawing Sheets

U.S. PATENT DOCUMENTS

| | | |
|---|---|---|
| 6,156,321 A | 12/2000 | Thorpe et al. |
| 6,181,909 B1 | 1/2001 | Burstein et al. |
| 6,201,065 B1 | 3/2001 | Pathak et al. |
| 6,207,218 B1 | 3/2001 | Layrolle et al. |
| 6,265,539 B1 | 7/2001 | Arlinghaus |
| 6,269,368 B1 | 7/2001 | Diamond |
| 6,270,765 B1 | 8/2001 | Deo et al. |
| 6,309,862 B1 | 10/2001 | Jarekrans et al. |
| 6,391,297 B1 | 5/2002 | Halvorsen |
| 6,444,723 B1 | 9/2002 | Kline |
| 6,458,924 B2 | 10/2002 | Knudsen et al. |
| 6,473,730 B1 | 10/2002 | McKeown et al. |
| 6,548,048 B1 | 4/2003 | Cuthbertson et al. |
| 6,548,630 B1 | 4/2003 | Zhang et al. |
| 6,562,619 B1 | 5/2003 | Gearhart et al. |
| 6,800,481 B1 | 10/2004 | Holmes et al. |
| 6,855,329 B1 | 2/2005 | Shakesheff et al. |
| 6,890,654 B2 | 5/2005 | Stupp et al. |
| 7,371,719 B2 | 5/2008 | Stupp et al. |
| 7,390,526 B2 | 6/2008 | Stupp et al. |
| 7,452,679 B2 | 11/2008 | Stupp et al. |
| 7,491,690 B2 | 2/2009 | Stupp et al. |
| 7,534,761 B1 | 5/2009 | Stupp et al. |
| 7,544,661 B2 | 6/2009 | Stupp et al. |
| 7,554,021 B2 | 6/2009 | Stupp et al. |
| 7,683,025 B2 | 3/2010 | Stupp et al. |
| 7,745,708 B2 | 6/2010 | Stupp et al. |
| 2002/0007217 A1 | 1/2002 | Jacob et al. |
| 2002/0046018 A1 | 4/2002 | Marcu et al. |
| 2002/0142277 A1 | 10/2002 | Burstein et al. |
| 2002/0160471 A1 | 10/2002 | Kisiday et al. |
| 2003/0050231 A1 | 3/2003 | Rosen et al. |
| 2003/0059906 A1 | 3/2003 | Hubbell et al. |
| 2003/0092672 A1 | 5/2003 | Darcy et al. |
| 2003/0176335 A1 | 9/2003 | Zhang et al. |
| 2003/0187232 A1 | 10/2003 | Hubbell et al. |
| 2004/0001893 A1* | 1/2004 | Stupp et al. ............... 424/488 |
| 2004/0018961 A1 | 1/2004 | Stupp et al. |
| 2004/0022718 A1 | 2/2004 | Stupp et al. |
| 2004/0068266 A1 | 4/2004 | Delmotte |
| 2004/0214272 A1 | 10/2004 | La Rosa et al. |
| 2004/0258726 A1 | 12/2004 | Stupp et al. |
| 2005/0208589 A1 | 9/2005 | Stupp et al. |
| 2005/0209145 A1 | 9/2005 | Stupp et al. |
| 2005/0214257 A1 | 9/2005 | Zhao et al. |
| 2005/0272662 A1 | 12/2005 | Stupp et al. |
| 2006/0008544 A1 | 1/2006 | Myhill et al. |
| 2006/0123505 A1 | 6/2006 | Kikuchi et al. |
| 2006/0149036 A1 | 7/2006 | Stupp et al. |
| 2006/0188555 A1 | 8/2006 | Cormier et al. |
| 2006/0247165 A1 | 11/2006 | Stupp et al. |
| 2007/0277250 A1 | 11/2007 | Stupp et al. |
| 2008/0175883 A1 | 7/2008 | Hsu et al. |
| 2008/0248569 A1 | 10/2008 | Mata et al. |
| 2008/0299657 A1 | 12/2008 | Stupp et al. |
| 2009/0042804 A1 | 2/2009 | Hulvat et al. |
| 2009/0098652 A1 | 4/2009 | Stupp et al. |
| 2009/0269847 A1 | 10/2009 | Stupp et al. |
| 2010/0221224 A1 | 9/2010 | Stupp et al. |
| 2011/0008890 A1 | 1/2011 | Stupp et al. |

FOREIGN PATENT DOCUMENTS

| | | | |
|---|---|---|---|
| CN | 1915438 A * | 2/2007 | |
| JP | 403099096 A | 4/1991 | |
| WO | 93/22343 A1 | 11/1993 | |
| WO | 94/02506 A1 | 2/1994 | |
| WO | 96/02260 A1 | 2/1996 | |
| WO | WO 97/14713 A1 | 4/1997 | |
| WO | WO 97/20639 A1 | 6/1997 | |
| WO | WO 98/07752 A1 | 2/1998 | |
| WO | 98/43686 A1 | 10/1998 | |
| WO | WO 99/36107 A1 | 7/1999 | |
| WO | 99/55383 A2 | 11/1999 | |
| WO | WO 00/13710 A2 | 3/2000 | |
| WO | WO 00/44808 A1 | 8/2000 | |
| WO | WO 00/45831 A1 | 8/2000 | |
| WO | WO 00/52145 A2 | 9/2000 | |
| WO | WO 00/64481 A1 | 11/2000 | |
| WO | WO 01/00650 A1 | 1/2001 | |
| WO | 01/48148 A1 | 7/2001 | |
| WO | 01/55302 A2 | 8/2001 | |
| WO | 01/56628 A1 | 8/2001 | |
| WO | 02/20822 A2 | 3/2002 | |
| WO | 02/39118 A1 | 5/2002 | |
| WO | WO 02/062969 A2 | 8/2002 | |
| WO | WO 03/040336 A2 | 5/2003 | |
| WO | WO 03/054146 A2 | 7/2003 | |
| WO | WO 03/070749 A2 | 8/2003 | |
| WO | WO 03/084980 A2 | 10/2003 | |
| WO | WO 03/090255 A2 | 10/2003 | |
| WO | WO 2004/003561 A1 | 1/2004 | |
| WO | WO 2004/018628 A2 | 3/2004 | |
| WO | WO 2004/024778 A2 | 3/2004 | |
| WO | WO 2004/046167 A2 | 6/2004 | |
| WO | WO 2004/072104 A2 | 8/2004 | |
| WO | 2004/091370 A2 | 10/2004 | |
| WO | WO 2004/106359 A2 | 12/2004 | |
| WO | WO 2005/003292 A2 | 1/2005 | |
| WO | 2005/014619 A2 | 2/2005 | |
| WO | WO 2005/056039 A1 | 6/2005 | |
| WO | WO 2005/056576 A2 | 6/2005 | |
| WO | WO 2006079036 A2 * | 7/2006 | |
| WO | WO 2006/096614 A2 | 9/2006 | |
| WO | 2008/131052 A2 | 10/2008 | |

OTHER PUBLICATIONS

Translation of CN 1915438 (Feb. 21, 2007).*

Tam, James P. 1996. "Recent Advances in Multiple Antigen Peptides." Journal of Immunological Methods. vol. 196, pp. 17-32.

Merkler, Doron, Gerlinde A. S. Metz, Olivier Raineteau, Volker Dietz, Martin E. Schwab, and Karim Fouad. May 15, 2001. "Locomotor Recovery in Spinal Cord-Injured Rats Treated with an Antibody Neutralizing the Myelin-Associated Neurite Growth Inhibitor Nogo-A." The Journal of Neuroscience. vol. 21, No. 10, pp. 3665-3673.

Bonnet, Dominique, Kader Thiam, Estelle Loing, Oleg Melnyk, and Héelène Gras-Masse. 2001. Synthesis by Chemoselective Ligation and Biological Evaluation of Novel Cell-Permeable PKC-ζ Pseudosubstrate Lipopeptides. J. Med. Chem. vol. 44, No. 3, pp. 468-471.

Grothe, Claudia and Guido Nikkhah. 2001. "The role of Basic Fibroblast Growth Factor in Peripheral Nerve Regeneration." Anat. Embryol. vol. 204, pp. 171-177.

Silva, G. A., C. Czeisler, K. L. Niece, E. Beniash, J. D. Hartgerink, J. A. Kessler, and S. I. Stupp. Nov. 2-7, 2002. "Development of Neural Progenitor Cells Encapsulated in a Peptide Amphiphile Substrate That is Induced to Self Assemble Under Physiological Conditions." Biosis. Society for Neuroscience Abstract Viewer and Itinerary Planner—2002. Abstract No. 825.4. 32nd Annual Meeting of the Society for Neuroscience; Orlando, Florida.

Leng, J., S. U. Egelhaaf, and M. E. Cates. Sep. 2003. "Kinetics of the Micelle-to-Vesicle Transition: Aqueous Lecithin-Bile Salt Mixtures." Biophysical Journal. vol. 85, No. 3, pp. 1624-1646.

Hui, Michael. May 24, 2004. "Heparin Binding Peptide Amphiphile and Transforming Growth Factor: A Novel Approach to Anti-Angiogenic Drug Delivery." The Second Annual Undergraduate Research Symposium. Retrieved from http://www.northwestern.edu/provost/students/research_symposium/program2004.pdf on Oct. 14, 2009. 45 pages.

Wayback Machine. http://www.archive.org/web/ entry, 1 page for http://www.northwestern.edu/provost/students/research_symposium/program2004.pdf retrieved on Oct. 14, 2009.

Clemetson, K. J., and J. M. Clemetson. 1998. "Integrins and Cardiovascular Disease." CMLS Cellular and Molecular Life Sciences. vol. 54, pp. 502-513.

Dupin, Elisabeth, and Nicole M. Le Douarin. 2003. "Development of Melanocyte Precursors from the Vertebrate Neural Crest." Oncogene. vol. 22, pp. 3016-3023.

Mardilovich, Anastasia, and Efrosini Kokkoli. 2004. "Biomimetic Peptide—Amphiphiles for Functional Biomaterials: The Role of GRGDSP and PHSRN." Biomacromolecules. vol. 5, No. 3, pp. 950-957.

Cui, Honggang, Takahiro Muraoka, Andrew G. Cheetham, and Samuel I. Stupp. 2009. "Self-Assembly of Giant Peptide Nanobelts." *Nano Letters.* vol. 9, No. 3, pp. 945-951.

Copping, Aaron M. and Vanda R. G. Pond. Dec. 9, 1950. "Folic Acid as a Growth-Factor for the Rat." *Nature.* No. 4232, p. 993.

Brown, Walter E. Dec. 15, 1962. "Octacalcium Phosphate and Hydroxyapatite." *Nature.* vol. 196, pp. 1048-1050.

Liang, W. Y. and A. D. Yoffe. Jan. 8, 1968. "Transmission Spectra of ZnO Single Crystals." *Physical Review Letters.* vol. 20, No. 2, pp. 59-62.

Greenfield, Norma and Gerald D. Fasman. Oct. 1969. "Computed Circular Dichroism Spectra for the Evaluation of Protein Conformation." *Biochemistry.* vol. 8, No. 10, pp. 4108-4116.

Hantke, Klaus and Volkmar Braun. 1973. "Covalent Binding of Lipid to Protein: Diglyceride and Amide-Linked Fatty Acid at the N-Terminal End of the Murein-Lipoprotein of the *Escherichia coli* Outer Membrane." *Eur. J. Biochem.* vol. 34, No. 2, pp. 284-296.

Balcerski, James S., E. S. Pysh, G. M. Bonora, and C. Toniolo. Jun. 9, 1976. "Vacuum Ultraviolet Circular Dichroism of β-Forming Alkyl Oligopeptides." *Journal of the American Chemical Society.* vol. 98, No. 12, pp. 3470-3473.

Jacobson, Bruce S. and Daniel Branton. Jan. 21, 1977. "Plasma Membrane: Rapid Isolation and Exposure of the Cytoplasmic Surface by Use of Positively Charged Beads." *Science.* vol. 195, No. 4275, pp. 302-304.

Biesecker, G., J. Ieuan Harris, J. C. Thierry, J. E. Walker, and A. J. Wonacott. Mar. 24, 1977. *Nature.* vol. 266, pp. 328-333.

Kelly, Margaret M., E. S. Pysh, G. M. Bonora, and C. Toniolo. May 11, 1977. "Vacuum Ultraviolet Circular Dichroism of Protected Homooligomers Derived from L-Leucine." *Journal of the American Chemical Society.* vol. 99, No. 10, pp. 3264-3266.

Blumenthal, N. C., A. S. Posner, L. D. Silverman, and L. C. Rosenberg. 1979. "Effect of Proteoglycans on in Vitro Hydroxyapatite Formation." *Calcified Tissue International.* vol. 27, No. 1, pp. 75-82.

Richardson, P. M., U. M. McGuinness, and A. J. Aguayo. Mar. 20, 1980. "Axons from CNS Neurones Regenerate into PNS Grafts." *Nature.* vol. 284, pp. 264-265.

Lim, Franklin and Anthony M. Sun. Nov. 21, 1980. "Microencapsulated Islets as Bioartificial Endocrine Pancreas." *Science.* vol. 210, No. 4472, pp. 908-910.

Jain, Rakesh K., Chhitar M. Gupta, and Nitya Anand. 1981. "Synthesis of Peptidylglycophospholipids, Novel Derivatives of Muramyl-Dipeptide." *Tetrahedron Letters.* vol. 22, No. 24, pp. 2317-2320.

Sarin, Virender K., Stephen B. H. Kent, James P. Tam, and R. B. Merrifield. 1981. "Quantitative Monitoring of Solid-Phase Peptide Synthesis by the Ninhydrin Reaction." *Analytical Biochemistry.* vol. 117, pp. 147-157.

Yannas, I. V., J. F. Burke, D. P. Orgill, E. M. Skrabut. Jan. 8, 1982. "Wound Tissue Can Utilize a Polymeric Template to Synthesize a Functional Extension of Skin." *Science.* vol. 215, No. 4529, pp. 174-176.

Montesano, R., L. Orci, and P. Vassalli. Nov. 1983. "In Vitro Rapid Organization of Endothelial Cells into Capillary-like Networks Is Promoted by Collagen Matrices." *The Journal of Cell Biology.* vol. 97, pp. 1648-1652.

Pierschbacher, Michael D. and Erkki Ruoslahti. May 3, 1984. "Cell Attachment Activity of Fibronectin Can Be Duplicated by Small Synthetic Fragments of the Molecule." *Nature.* vol. 309, pp. 30-33.

Landis, W. J. and J. R. Martin. Apr.-Jun. 1984. "X-Ray Photoelectron Spectroscopy Applied to Gold-Decorated Mineral Standards of Biological Interest." *J. Vac. Sci. Technol.* vol. A 2, No. 2, pp. 1108-1111.

Thompson, Nancy L., Adrienne A. Brian, and Harden M. McConnell. 1984. "Covalent Linkage of a Synthetic Peptide to a Fluorescent Phospholipid and Its Incorporation into Supported Phospholipid Monolayers." *Biochimica et Biophysica Acta.* vol. 772, pp. 10-19.

Yamada, Kimiho, Hirotaka Ihara, Toshio Ide, Takanori Fukumoto, and Chuichi Hirayama. 1984. "Formation of Helical Super Structure from Single-Walled Bilayers by Amphiphiles with Oligo-L-Glutamic Acid-Head Group." *Chemistry Letters.* No. 10, pp. 1713-1716.

Addadi, L. and S. Weiner. Jun. 15, 1985. "Interactions Between Acidic Proteins and Crystals: Stereochemical Requirements in Biomineralization." *Proceedings of the National Academy of Sciences of the United States of America.* vol. 82, No. 12, pp. 4110-4114.

"Public Health Service Policy on Humane Care and Use of Laboratory Animals." Sep. 1986. Office for Protection from Research Risks (OPRR), National Institutes of Health.

Weiner, Stephen and Wolfie Traub. Oct. 1986. "Organization of Hydroxyapatite Crystals Within Collagen Fibrils." *FEBS Letters.* vol. 206, No. 2, pp. 262-266.

Mann, Stephen, John P. Hannington, and R. J. P. Williams. Dec. 11, 1986. "Phospholipid Vesicles as a Model System for Biomineralization." *Nature.* vol. 324, pp. 565-567.

Krimm, Samuel and Jagdeesh Bandekar. 1986. "Vibrational Spectroscopy and Conformation of Peptides, Polypeptides, and Proteins." *Advances in Protein Chemistry.* vol. 38, pp. 181-364.

de Groot, K., R. Geesink, C. P. A. T. Klein, and P. Serekian. Dec. 1987. "Plasma Sprayed Coatings of Hydroxylapatite." *Journal of Biomedical Materials Research.* vol. 21, No. 12, pp. 1375-1381.

Bresnahan, J. C., M. S. Beattie, F. D. Todd III, and D. H. Noyes. 1987. "A Behavioral and Anatomical Analysis of Spinal Cord Injury Produced by a Feedback-Controlled Impaction Device." *Experimental Neurology.* vol. 95, pp. 548-570.

Moscatelli, David. 1987. "High and Low Affinity Binding Sites for Basic Fibroblast Growth Factor on Cultured Cells: Absence of a Role for Low Affinity Binding in the Stimulation of Plasminogen Activator Production by Bovine Capillary Endothelial Cells." *Journal of Cellular Physiology.* vol. 131, pp. 123-130.

Lambert, Joseph B., Herbert F. Shurvell, David A. Lightner, and R. Graham Cooks. 1987. "Group Frequencies: Infrared and Raman." *Introduction to Organic Spectroscopy.* New York: Macmillan Publishing Company. pp. 169-182.

Cook, Stephen D., Kevin A. Thomas, John F. Kay, and Michael Jarcho. Jul. 1988. "Hydroxyapatite-Coated Titanium for Orthopedic Implant Applications." *Clinical Orthopaedics and Related Research.* No. 232, pp. 225-243.

Saksela, Olli, David Moscatelli, Andreas Sommer, and Daniel B. Rifkin Aug. 1988. "Endothelial Cell-Derived Heparan Sulfate Binds Basic Fibroblast Growth Factor and Protects It from Proteolytic Degradation." *The Journal of Cell Biology.* vol. 107, pp. 743-751.

Cardin, Alan D. and H. J. R. Weintraub. Jan./Feb. 1989. "Molecular Modeling of Protein-Glycosaminoglycan Interactions." *Arteriosclerosis.* vol. 9, No. 1, pp. 21-32.

Oonishi, H., M. Yamamoto, H. Ishimaru, E. Tsuji, S. Kuskitani, M. Aono, and Y. Ukon. Mar. 1989. "The Effect of Hydroxyapatite Coating on Bone Growth into Porous Titanium Alloy Implants." *The Journal of Bone and Joint Surgery.* vol. 71-B, No. 2, pp. 213-216.

Friedmann, Theodore. Jun. 16, 1989. "Progress Toward Human Gene Therapy." *Science.* vol. 244, No. 4910, pp. 1275-1281.

Traub, Wolfie, Talmon Arad, and Stephen Weiner. Dec. 15, 1989. "Three-Dimensional Ordered Distribution of Crystals in Turkey Tendon Collagen Fibers." *Proceedings of the National Academy of Sciences of the United States of America.* vol. 86, No. 24, pp. 9822-9826.

Knorr, Reinhard, Arnold Trzeciak, Willi Bannwarth, and Dieter Gillessen. 1989. "New Coupling Reagents in Peptide Chemistry." *Tetrahedron Letters.* vol. 30, No. 15, pp. 1927-1930.

Sambrook, Joseph, Edward F. Fritsch, and Thomas Maniatis. 1989. "Genes Encoding Selectable Markers." *Molecular Cloning: A Laboratory Manual.* $2^{nd}$ ed. New York: Cold Spring Harbor Laboratory Press. pp. 16.9-16.15.

Veis, A. 1989. "Biochemical Studies of Vertebrate Tooth Mineralization." *Biomineralization.* S. Maim, J. Webb, and R. J. P. Williams, editors. Weinheim, Federal Republic of Germany: VCH Verlagsgesellschaft and New York: VCH Publishers. pp. 189-222.

Schnell, Lisa and Martin E. Schwab. Jan. 18, 1990. "Axonal Regeneration in the Rat Spinal Cord Produced by an Antibody Against Myelin-Associated Neurite Growth Inhibitors." *Nature.* vol. 343, pp. 269-272.

Ahn, Sang Tae and Thomas A. Mustoe. Jan. 1990. "Effects of Ischemia on Ulcer Wound Healing: A New Model in the Rabbit Ear." *Annals of Plastic Surgery.* vol. 24, No. 1, pp. 17-23.

Van de Pol, Frans C. M. Dec. 1990. "Thin-Film ZnO—Properties and Applications." *Ceramic Bulletin.* vol. 69, No. 12, pp. 1959-1965.

Addadi, L., A. Berman, J. Moradian-Oldak, and S. Weiner. Dec. 28, 1990. "Tuning of Crystal Nucleation and Growth by Proteins: Molecular Interactions at Solid-Liquid Interfaces in Biomineralization." *Croatica Chemica Acta*. vol. 63, No. 3, pp. 539-544.

Sukenik, Chaim N., Natarajan Balachander, Lloyd A. Culp, Kristine Lewandowska, and Katherine Merritt. 1990. "Modulation of Cell Adhesion by Modification of Titanium Surfaces with Covalently Attached Self-Assembled Monolayers." *Journal of Biomedical Materials Research*. vol. 24, pp. 1307-1323.

Fields, C. G., D. H. Lloyd, R. L. Macdonald, K. M. Otteson, and R. L. Noble. Mar./Apr. 1991. "HBTU Activation for Automated Fmoc Solid-Phase Peptide Synthesis." *Peptide Research*. vol. 4, No. 2, pp. 95-101.

Murata, Masayuki, Satoshi Kagiwada, Sho Takahashi, and Shun-ichi Ohnishi. Aug. 5, 1991. "Membrane Fusion Induced by Mutual Interaction of the Two Charge-Reversed Amphiphilic Peptides at Neutral pH." *The Journal of Biological Chemistry*. vol. 56, No. 22, pp. 14353-14358.

Harris, Robin, Editor. 1991. *Electron Microscopy in Biology: A Practical Approach.* New York: Oxford University Press.

Jackson, David Y., David S. King, Jean Chmielewski, Sunil Singh, and Peter G. Schultz. 1991. "General Approach to the Synthesis of Short α-Helical Peptides." *Journal of the American Chemical Society*. vol. 113, pp. 9391-9392.

Polverini, Peter J., Noel P. Bouck, and Farzan Rastinejad. 1991. "Assay and Purification of Naturally Occurring Inhibitor of Angiogenesis." *Methods in Enzymology*. vol. 198, pp. 440-450.

Weiner, Stephen and Wolfie Traub. Feb. 1992. "Bone Structure: From Ångstroms to Microns." *The FASEB Journal*. vol. 6, pp. 879-885.

Nomizu, Motoyoshi, Atsushi Utani, Norio Shiraishi, Maura C. Kibbey, Yoshihiko Yamada, and Peter P. Roller. Jul. 15, 1992. "The All-D-Configuration Segment Containing the IKVAV Sequence of Laminin A Chain Has Similar Activities to the All-L-Peptide in Vitro and in Vivo." *The Journal of Biological Chemistry*. vol. 267, No. 20, pp. 14118-14121.

Addadi, Lia and Stephen Weiner. 1992. "Control and Design Principles in Biological Mineralization." *Angew. Chem. Int. Ed. Engl.* vol. 31, pp. 153-169.

Beresford, J. N., J. H. Bennett, C. Devlin, P. S. Leboy, and M. E. Owen. 1992. "Evidence for an Inverse Relationship Between the Differentiation of Adipocytic and Osteogenic Cells in Rat Marrow Stromal Cell Cultures." *Journal of Cell Science*. vol. 102, pp. 341-351.

Cook, Stephen D., Kevin A. Thomas, Jeanette E. Dalton, Todd K. Volkman, Thomas S. Whitecloud III, and John F. Kay. 1992. "Hydroxylapatite Coating of Porous Implants Improves Bone Ingrowth and Interface Attachment Strength." *Journal of Biomedical Materials Research*. vol. 26, pp. 989-1001.

Geahlen, Robert L., G. Marc Loudon, Lisa A. Paige, and David Lloyd. 1992. "A General Method for Preparation of Peptides Biotinylated at the Carboxy Terminus." *Analytical Biochemistry*. vol. 202, pp. 68-70.

Ghadiri, M. Reza, Christopher Soares, and Chong Choi. 1992. "Design of an Artificial Four-Helix Bundle Metalloprotein via a Novel Ruthenium(II)-Assisted Self-Assembly Process." *Journal of the American Chemical Society*. vol. 114, No. 10, pp. 4000-4002.

Kunitake, Toyoki. 1992. "Synthetic Bilayer Membranes: Molecular Design, Self-Organization, and Application." *Angew. Chem. Int. Ed. Engl.* vol. 31, pp. 709-726.

Stupp, Samuel I. and Glenn W. Ciegler. 1992. "Organoapatites: Materials for Artificial Bone. I. Synthesis and Microstructure." *Journal of Biomedical Materials Research*. vol. 26, pp. 169-183.

Surewicz, Witold K., Henry H. Mantsch, and Dennis Chapman Jan. 19, 1993. "Determination of Protein Secondary Structure by Fourier Transform Infrared Spectroscopy: A Critical Assessment" *Biochemistry*. vol. 32, No. 2, pp. 389-394.

Zhang, Shuguang, Todd Holmes, Curtis Lockshin, and Alexander Rich. Apr. 15, 1993. "Spontaneous Assembly of a Self-Complementary Oligopeptide to Form a Stable Macroscopic Membrane." *Proceedings of the National Academy of Sciences of the United States of America*. vol. 90, No. 8, pp. 3334-3338.

Langer, Robert and Joseph P. Vacanti. May 14, 1993. "Tissue Engineering." *Science*. vol. 260, No. 5110, pp. 920-926.

Mulligan, Richard C. May 14, 1993. "The Basic Science of Gene Therapy." *Science*. vol. 260, No. 5110, pp. 926-932.

Massas, R., S. Pitaru, and M. M. Weinreb. Jun. 1993. "The Effects of Titanium and Hydroxyapatite on Osteoblastic Expression and Proliferation in Rat Parietal Bone Cultures." *Journal of Dental Research*. vol. 72, No. 6, pp. 1005-1008.

Archibald, Douglas D. and Stephen Mann. Jul. 29, 1993. "Template Mineralization of Self-Assembled Anisotropic Lipid Microstructures." *Nature*. vol. 364, pp. 430-433.

Atala, Anthony, Linda G. Cima, Wooseob Kim, Keith T. Paige, Joseph P. Vacanti, Alan B. Retik, and Charles A. Vacanti. Aug. 1993. "Injectable Alginate Seeded with Chondrocytes as a Potential Treatment for Vesicoureteral Reflux." *The Journal of Urology*. vol. 150, No. 2, pp. 745-747.

Nomizu, Motoyoshi, Keizo Yamamura, Hynda K. Kleinman, and Yoshihiko Yamada. Aug. 1, 1993. "Multimeric Forms of Tyr-Ile-Gly-Ser-Arg (YIGSR) Peptide Enhance the Inhibition of Tumor Growth and Metastasis." *Cancer Research*. vol. 53, pp. 3459-3461.

Ross-Murphy, S. B. and K. P. Shatwell. May-Aug. 1993. "Polysaccharide Strong and Weak Gels." *Biorheology*. vol. 30, Nos. 3 & 4, pp. 217-227.

Margalit, Hanah, Nurit Fischer, and Shmuel A. Ben-Sasson. Sep. 15, 1993. "Comparative Analysis of Structurally Defined Heparin Binding Sequences Reveals a Distinct Spatial Distribution of Basic Residues." *The Journal of Biological Chemistry*. vol. 268, No. 26, pp. 19228-19231.

Fowler, Bruce O., Milenko Marković, and Walter E. Brown. 1993. "Octacalcium Phosphate. 3. Infrared and Raman Vibrational Spectra." *Chem. Mater*. vol. 5, No. 10, pp. 1417-1423.

Fuhrhop, Jürgen-Hinrich, Dragan Spiroski, and Christoph Boettcher. 1993. "Molecular Monolayer Rods and Tubules Made of α-(L-Lysine),ω-(Amino) Bolaamphiphiles." *Journal of the American Chemical Society*. vol. 115, No. 4, pp. 1600-1601.

Graham, Stephan and Paul W. Brown. 1993. "The Low Temperature Formation of Octacalcium Phosphate." *Journal of Crystal Growth*. vol. 132, pp. 215-225.

Shimizu, Toshimi and Masakatsu Hato. 1993. "Self-Assembling Properties of Synthetic Peptidic Lipids." *Biochimica et Biophysica Acta*. vol. 1147, pp. 50-58.

Stupp, Samuel I., Jacqueline A. Hanson, Jo Ann Eurell, Glenn W. Ciegler, and Ann Johnson. 1993. "Organoapatites: Materials for Artifical Bone. III. Biological Testing." *Journal of Biomedical Materials Research*. vol. 27, pp. 301-311.

Stupp, Samuel I., George C. Mejicano, and Jacqueline A. Hanson. 1993. "Organoapatites: Materials for Artificial Bone. II. Hardening Reactions and Properties." *Journal of Biomedical Materials Research*. vol. 27, pp. 289-299.

Wald, Heidi L., Georgios Sarakinos, Michelle D. Lyman, Antonios G. Mikos, Joseph P. Vacanti, and Robert Langer. 1993. "Cell Seeding in Porous Transplantation Devices." *Biomaterials*. vol. 14, No. 4, pp. 270-278.

Walsh, Dominic, Joanne L. Kingston, Brigid R. Heywood, and Stephen Mann. 1993. "Influence of Monosaccharides and Related Molecules on the Morphology of Hydroxyapatite." *Journal of Crystal Growth*. vol. 133, pp. 1-12.

Wang, B. C., T. M. Lee, E. Chang, and C. Y. Yang. 1993. "The Shear Strength and the Failure Mode of Plasma-Sprayed Hydroxyapatite Coating to Bone: The Effect of Coating Thickness." *Journal of Biomedical Materials Research*. vol. 27, pp. 1315-1327.

San Antonio, James D., Arthur D. Lander, Morris J. Karnovsky, and Henry S. Slayter. Jun. 1994. "Mapping the Heparin-Binding Sites on Type I Collagen Monomers and Fibrils." *The Journal of Cell Biology*. vol. 125, No. 5, pp. 1179-1188.

Ban, S., S. Maruno, H. Iwata, and H. Itoh. 1994. "Calcium Phosphate Precipitation on the Surface of HA-G-Ti Composite Under Physiologic Conditions." *Journal of Biomedical Materials Research*. vol. 28, pp. 65-71.

de Bruijn, J. D., Y. P. Bovell, and C. A. van Blitterswijk. 1994. "Structural Arrangements at the Interface Between Plasma Sprayed Calcium Phosphates and Bone." *Biomaterials*. vol. 15, No. 7, pp. 543-550.

Hunter, Graeme K. and Harvey A. Goldberg. 1994. "Modulation of Crystal Formation by Bone Phosphoproteins: Role of Glutamic Acid- Rich Sequences in the Nucleation of Hydroxyapatite by Bone Sialoprotein." *Biochem. J.* vol. 302, pp. 175-179.

Klein, C. P. A. T., J. G. C. Wolke, J. M. A. de Blieck-Hogervorst, and K. de Groot. 1994. "Calcium Phosphate Plasma-Sprayed Coatings and Their Stability: An in Vivo Study." *Journal of Biomedical Materials Research.* vol. 28, pp. 909-917.

Margomenou-Leonidopoulou, G. 1994. "Thermotropic Mesophases of Ionic Amphiphiles. II. Ionic Amphiphiles in Aqueous Media." *Journal of Thermal Analysis.* vol. 42, pp. 1041-1061.

Mikos, Antonios G., Michelle D. Lyman, Lisa E. Freed, and Robert Langer. 1994. "Wetting of Poly(L-Lactic Acid) and Poly(DL-Lactic-co-glycolic Acid) Foams for Tissue Culture." *Biomaterials.* vol. 15, No. 1, pp. 55-58.

Bond, G. M., R. H. Richman, and W. P. McNaughton. Jun. 1995. "Mimicry of Natural Material Designs and Processes." *Journal of Materials Engineering and Performance.* vol. 4, No. 3, pp. 334-345.

Hubbell, Jeffrey A. Jun. 1995. "Biomaterials in Tissue Engineering." *Bio/technology.* vol. 13, pp. 565-576.

Fromm, J. R., R. E. Hileman, E. E. O. Caldwell, J. M. Weiler, and R. J. Linhardt. Nov. 10, 1995. "Differences in the Interaction of Heparin with Arginine and Lysine and the Importance of these Basic Amino Acids in the Binding of Heparin to Acidic Fibroblast Growth Factor." *Archives of Biochemistry and Biophysics.* vol. 323, No. 2, pp. 279-287.

Wakitani, Shigeyuki, Tomoyuki Saito, and Arnold I. Caplan. Dec. 1995. "Myogenic Cells Derived from Rat Bone Marrow Mesenchymal Stem Cells Exposed to 5-Azacytidine." *Muscle & Nerve.* vol. 18, pp. 1417-1426.

Aletras, Alexios, Kleomenis Barlos, Dimitrios Gatos, Sophia Koutsogianni, and Petros Mamos. 1995. "Preparation of the Very Acid-Sensitive Fmoc-Lys(Mtt)-OH." *International Journal of Peptide & Protein Research.* vol. 45, pp. 488-496.

Berndt, Peter, Gregg B. Fields, and Matthew Tirrell. 1995. "Synthetic Lipidation of Peptides and Amino Acids: Monolayer Structure and Properties." *Journal of the American Chemical Society.* vol. 117, No. 37, pp. 9515-9522.

Gage, Fred H., Jasodhara Ray, and Lisa J. Fisher. 1995. "Isolation, Characterization, and Use of Stem Cells from the CNS." *Annual Review of Neuroscience.* vol. 18, pp. 159-192.

Jackowski, Andre. 1995. "Neural Injury Repair: Hope for the Future as Barriers to Effective CNS Regeneration Become Clearer." *J. Neurosurg.* vol. 9, pp. 303-317.

Nomizu, Motoyoshi, Benjamin S. Weeks, Christi A. Weston, Woo Hoo Kim, Hynda K. Kleinman, and Yoshihiko Yamada. 1995. "Structure-Activity Study of a Laminin α1 Chain Active Peptide Segment Ile-Lys-Val-Ala-Val (IKVAV)." *FEBS Letters.* vol. 365, pp. 227-231.

Saito, Tomoyuki, James E. Dennis, Donald P. Lennon, Randell G. Young, and Arnold I. Caplan. 1995. "Myogenic Expression of Mesenchymal Stem Cells Within Myotubes of *mdx* Mice in Vitro and in Vivo." *Tissue Engineering.* vol. 1, No. 4, pp. 327-343.

Sasanuma, Michio. 1995. "Optical Processes in ZnO." *J Phys.: Condens. Matter.* vol. 7, pp. 10029-10036.

Zhang, Shuguang, Todd C. Holmes, C. Michael DiPersio, Richard O. Hynes, Xing Su, and Alexander Rich. 1995. "Self-Complementary Oligopeptide Matrices Support Mammalian Cell Attachment." *Biomaterials.* vol. 16, No. 18, pp. 1385-1393.

Falini, Guiseppe, Shira Albeck, Steve Weiner, and Lia Addadi. Jan. 5, 1996. "Control of Aragonite or Calcite Polymorphism by Mollusk Shell Macromolecules." *Science.* vol. 271, No. 5245, pp. 67-69.

Alivisatos, A. P. Feb. 16, 1996. "Semiconductor Clusters, Nanocrystals, and Quantum Dots." *Science.* vol. 271, No. 5251, pp. 933-937.

Keyt, Bruce A., Lea T. Berleau, Hung V. Nguyen, Helen Chen, Henry Heinsohn, Richard Vandlen, and Napoleone Ferrara. Mar. 29, 1996. "The Carboxyl-terminal Domain (111-165) of Vascular Endothelial Growth Factor is Critical for its Mitogenic Potency." *The Journal of Biological Chemistry.* vol. 271, No. 13, pp. 7788-7795.

Belcher, A. M., X. H. Wu, R. J. Christensen, P. K. Hansma, G. D. Stucky, and D. E. Morse. May 2, 1996. "Control of Crystal Phase Switching and Orientation by Soluble Mullusc-Shell Proteins." *Nature.* vol. 381, pp. 56-58.

Hortelano, Gonzalo, Ayman Al-Hendy, Frederick A. Ofosu, and Patricia L. Chang. Jun. 15, 1996. "Delivery of Human Factor IX in Mice by Encapsulated Recombinant Myoblasts: A Novel Approach Towards Allogenic Gene Therapy of Hemophilia B." *Blood.* vol. 87, No. 12, pp. 5095-5103.

Sultzbaugh, K. J. and T. J. Speaker. Jul.-Aug. 1996. "A Method to Attach Lectins to the Surface of Spermine Alginate Microcapsules Based on the Avidin Biotin Interaction." *J. Microencapsulation.* vol. 13, No. 4, pp. 363-375.

Alivisatos, A. Paul, Kai P. Johnsson, Xiaogang Peng, Troy E. Wilson, Colin J. Loweth, Marcel P. Burchez Jr., and Peter G. Schultz. Aug. 15, 1996. "Organization of 'Nanocrystal Molecules' Using DNA." *Nature.* vol. 382, pp. 609-611.

George, Anne, Leslie Bannon, Boris Sabsay, Jerry W. Dillon, James Malone, Arthur Veis, Nancy A. Jenkins, Debra J. Gilbert, and Neal G. Copeland. Dec. 20, 1996. "The Carboxyl-terminal Domain of Phosphophoryn Contains Unique Extended Triplet Amino Acid Repeat Sequences Forming Ordered Carboxyl-Phosphate Interaction Ridges That May Be Essential in the Biomineralization Process." *The Journal of Biological Chemistry.* vol. 271, No. 51, pp. 32869-32873.

Basso, D. Michele, Michael S. Beattie, and Jacqueline C. Bresnahan. 1996. "Graded Histological and Locomotor Outcomes after Spinal Cord Contusion Using the NYU Weight-Drop Device Versus Transection." *Experimental Neurology.* vol. 139, pp. 244-256.

Burkett, Sandra L. and Stephen Mann. 1996. "Spatial Organization and Patterning of Gold Nanoparticles on Self-Assembled Biolipid Tubular Templates." *Chem. Commun.* pp. 321-322.

Hunter, Graeme K., Peter V. Hauschka, A. Robin Poole, Lawrence C. Rosenberg, and Harvey A. Goldberg. 1996. "Nucleation and Inhibition of Hydroxyapatite Formation by Mineralized Tissue Proteins." *Biochem. J.* vol. 317, pp. 59-64.

Karymov, Mikhail A., Karel Procházka, John M. Mendenhall, Thomas J. Martin, Petr Munk, and Stephen E. Webber. 1996. "Chemical Attachment of Polystyrene-*block*-poly(methacrylic acid) Micelles on a Silicon Nitride Surface." *Langmuir.* vol. 12, No. 20, 4748-4753.

Landis, William J., Karen J. Hodgens, James Arena, Min Ja Song, and Bruce F. McEwen. 1996. "Structural Relations Between Collagen and Mineral in Bone as Determined by High Voltage Electron Microscopic Tomography." *Microscopy Research and Technique.* vol. 33, pp. 192-202.

Matsuzawa, Mieko, Forrest F. Weight, Richard S. Potember, and Päivi Liesi. 1996. "Directional Neurite Outgrowth and Axonal Differentiation of Embryonic Hippocampal Neurons Are Promoted by a Neurite Outgrowth Domain of the B2-Chain of Laminin." *Int. J. Devl. Neuroscience.* vol. 14, No. 3, pp. 283-295.

Mooney, David J., Daniel F. Baldwin, Nam P. Suh, Joseph P. Vacanti, and Robert Langer. 1996. "Novel Approach to Fabricate Porous Sponges of Poly(D,L-Lactic-co-glycolic Acid) Without the Use of Organic Solvents." *Biomaterials.* vol. 17, No. 14, pp. 1417-1422.

Rappolt, Michael and Gert Rapp. 1996. "Structure of the Stable and Metastable Ripple Phase of Dipalmitoylphosphatidylcholine." *Eur. Biophys. J.* vol. 24, pp. 381-386.

Ratner, Buddy D., Allan S. Hoffman, Frederick J. Schoen, and Jack E. Lemons, Editors. 1996. *Biomaterials Science: An Introduction to Materials in Medicine.* San Diego, CA: Academic Press.

Ulman, Abraham. 1996. "Formation and Structure of Self-Assembled Monolayers." *Chemical Reviews.* vol. 96, No. 4, pp. 1533-1554.

Yu, Ying-Ching, Peter Berndt, Matthew Tirrell, and Gregg B. Fields. 1996. "Self-Assembling Amphiphiles for Construction of Protein Molecular Architecture." *Journal of the American Chemical Society.* vol. 118, No. 50, pp. 12515-12520.

Zarif, Leila, Ange Polidori, Bernard Pucci, Tadek Gulik-Krzywicki, André A. Pavia, and Jean G. Riess. 1996. "Effect of Chirality on the Formation of Tubules from Glycolipidic Amphiphiles." *Chemistry and Physics of Lipids.* vol. 79, pp. 165-170.

Aggeli, A., M. Bell, N. Boden, J. N. Keen, P. F. Knowles, T. C. B. McLeish, M. Pitkeathly, and S. E. Radford. Mar. 20, 1997. "Responsive Gels Formed by the Spontaneous Self-Assembly of Peptides into Polymeric β-Sheet Tapes." *Nature.* vol. 386, pp. 259-262.

Herr, Andrew B., David M. Ornitz, Ram Sasisekharan, Ganesh Venkataraman, and Gabriel Waksman. Jun. 27, 1997. "Heparin-Induced Self-Association of Fibroblast Growth Factor-2." *The Journal of Biological Chemistry.* vol. 272, No. 26, pp. 16382-16389.

Dimmeler, Stefanie and Andreas M. Zeiher. Aug. 1997. "Nitric Oxide and Apoptosis: Another Paradigm for the Double-Edged Role of Nitric Oxide." *Nitric Oxide: Biology and Chemistry*. vol. 1, No. 4, pp. 275-281.

Stupp, Samuel I. and Paul V. Braun. Aug. 29, 1997. "Molecular Manipulation of Microstructures: Biomaterials, Ceramics, and Semiconductors." *Science*. vol. 277, No. 5330, pp. 1242-1248.

Kaufmann, P. M., S. Heimrath, B. S. Kim, and D. J. Mooney. Sep./Oct. 1997. "Highly Porous Polymer Matrices as a Three-Dimensional Culture System for Hepatocytes." *Cell Transplantation*. vol. 6, No. 5, pp. 463-468.

Aggeli, Amalia, Mark Bell, Neville Boden, Jeff N. Keen, Tom C. B. McLeish, Irina Nyrkova, Sheena E. Radford, and Alexander Semenov. 1997. "Engineering of Peptide β-Sheet Nanotapes." *J. Mater. Chem.* vol. 7, No. 7, pp. 1135-1145.

Anderson, James M. and Matthew S. Shive. 1997. "Biodegradation and Biocompatibility of PLA and PLGA Microspheres." *Advanced Drug Delivery Reviews*. vol. 28, pp. 5-24.

Draget, Kurt Ingar, Gudmund Skjåk-Bræk, Olav Smidsrød. 1997. "Alginate Based New Materials." *International Journal of Biological Macromolecules*. vol. 21, pp. 47-55.

El-Ghannam, Ahmed, Paul Ducheyne, and Irving M. Shapiro. 1997. "Porous Bioactive Glass and Hydroxyapatite Ceramic Affect Bone Cell Function in Vitro Along Different Time Lines." *Journal of Biomedical Materials Research*. vol. 36, pp. 167-180.

Goveas, J. L. and S. T. Milner. 1997. "Dynamics of the Lamellar—Cylindrical Transition in Weakly Segregated Diblock Copolymer Melts." Macromolecules. vol. 30, No. 9, pp. 2605-2612.

Jaiswal, Neelam, Stephen E. Haynesworth, Arnold I. Caplan, and Scott P. Bruder. 1997. "Osteogenic Differentiation of Purified, Culture-Expanded Human Mesenchymal Stem Cells in Vitro." *Journal of Cellular Biochemistry*. vol. 64, pp. 295-312.

Munson, John B. and Stephen B. McMahon. 1997. "Effects of GDNF on Axotomized Sensory and Motor Neurons in Adult Rats." European Journal of Neuroscience. vol. 9, pp. 1126-1129.

Nehrer, Stefan, Howard A. Breinan, Arun Ramappa, Sonya Shortkroff, Gretchen Young, Tom Minas, Clement B. Sledge, Ioannis V. Yannas, and Myron Spector. 1997. "Canine Chondrocytes Seeded in Type I and Type II Collagen Implants Investigated in Vitro." *Journal of Biomedical Materials Research (Appl. Biomater.)*. vol. 38, pp. 95-104.

Mann, Stephen. 1997. "Biomineralization: The Form(id)able Part of Bioinorganic Chemistry!" *J. Chem. Soc., Dalton Trans.* pp. 3953-3961.

Norrby, Klas. 1997. "Angiogenesis: New Aspects Relating to Its Initiation and Control." *APMIS*. vol. 105, pp. 417-437.

Shimizu, Toshimi, Masaki Kogiso, and Mitsutoshi Masuda. 1997. "Noncovalent Formation of Polyglycine II-Type Structure by Hexagonal Self-Assembly of Linear Polymolecular Chains." *Journal of the Americal Chemical Society*. vol. 119, No. 26, pp. 6209-6210, S2-S17.

Smith, George P. and Valery A. Petrenko. 1997. "Phage Display." *Chemical Reviews*. vol. 97, No. 2, pp. 391-410.

Toyotama, Akiko, Shin-ichi Kugimiya, Masakatsu Yonese, Takatoshi Kinoshita, and Yoshiharu Tsujita. 1997. "Controllable Orientation of the Peptide-Based Surfactant at Air-Water Interface." *Chemistry Letters*. pp. 443-444.

Weiner, Stephen and Lia Addadi. 1997. "Design Strategies in Mineralized Biological Materials." *J. Mater. Chem.* vol. 7, No. 5, pp. 689-702.

Wellings, Donald A. and Eric Atherton. 1997. "Standard Fmoc Protocols." *Methods in Enzymology*. vol. 289, pp. 44-67.

Wen, H. B., J. G. C. Wolke, J. R. de Wijn, Q. Liu, F. Z. Cui, and K. de Groot. 1997. "Fast Precipitation of Calcium Phosphate Layers on Titanium Induced by Simple Chemical Treatments." *Biomaterials*. vol. 18, No. 22, pp. 1471-1478.

Yu, Ying-Ching, Teika Pakalns, Yoav Dori, James B. McCarthy, Matthew Tirrell, and Gregg B. Fields. 1997. "Construction of Biologically Active Protein Molecular Architecture Using Self-Assembling Peptide-Amphiphiles." *Methods in Enzymology*. vol. 289, pp. 571-587.

Zhitomirsky, I. and L. Gal-Or. 1997. "Electrophoretic Deposition of Hydroxyapatite." *Journal of Materials Science: Materials in Medicine*. pp. 213-219.

Veis, Arthur, Kuiru Wei, Charles Sfeir, Anne George, and James Malone. Jan. 1998. "Properties of the $(DSS)_n$ Triplet Repeat Domain of Rat Dentin Phosphophoryn." *European Journal of Oral Sciences*. vol. 106 (suppl. 1), pp. 234-238.

Pincus, David W., Robert R. Goodman, Richard A. R. Fraser, Maiken Nedergaard, and Steven A. Goldman. Apr. 1998. "Neural Stem and Progenitor Cells: A Strategy for Gene Therapy and Brain Repair." *Neurosurgery*. vol. 42, No. 4, pp. 858-867.

Ogiso, M., Y. Yamashita, and T. Matsumoto. Jun. 1998. "The Process of Physical Weakening and Dissolution of the HA-Coated Implant in Bone and Soft Tissue." *Journal of Dental Research*. vol. 77, No. 6, pp. 1426-1434.

Petka, Wendy A., James L. Harden, Kevin P. McGrath, Denis Wirtz, and David A. Tirrell. Jul. 17, 1998. "Reversible Hydrogels from Self-Assembling Artificial Proteins." *Science*. vol. 281, No. 5375, pp. 389-392.

Orgill, Dennis P., Charles Butler, John F. Regan, Mark S. Barlow, I. V. Yannas, and Carolyn C. Compton. Aug. 1998. "Vascularized Collagen-Glycosaminoglycan Matrix Provides a Dermal Substrate and Improves Take of Cultured Epithelial Autografts." *Plastic and Reconstructive Surgery*. vol. 102, No. 2, pp. 423-429.

Yu, Ying-Ching, Matthew Tirrell, and Gregg B. Fields. Oct. 7, 1998. "Minimal Lipidation Stabilizes Protein-Like Molecular Architecture." *Journal of the American Chemical Society*. vol. 120, No. 39, pp. 9979-9987.

Borkenhagen, M., J.-F. Clémence, H. Sigrist, and P. Aebischer. 1998. "Three-Dimensional Extracellular Matrix Engineering in the Nervous System." *Journal of Biomedical Materials Research*. vol. 40, pp. 392-400.

Brekke, John H. and Jeffrey M. Toth. 1998. "Principles of Tissue Engineering Applied to Programmable Osteogenesis." *Journal of Biomedical Materials Research (Appl. Biomater.)*. vol. 43, pp. 380-398.

Fernandez, A., M. A. Alsina, I. Haro, R. Galantai, and F. Reig. 1998. "Synthesis and Physicochemical Characterization of Cyclic Laminin Related Peptides." *Langmuir*. vol. 14, No. 13, pp. 3625-3630.

Fields, Gregg B., Janette L. Lauer, Yoav Dori, Pilar Forns, Ying-Ching Yu, and Matthew Tirrell. 1998. "Proteinlike Molecular Architecture: Biomaterial Applications for Inducing Cellular Receptor Binding and Signal Transduction." *Biopolymers (Peptide Science)*. vol. 47, pp. 143-151.

Gu, Keni, Syweren R. Chang, Matt S. Slaven, Brian H. Clarkson, R. Bruce Rutherford, and Helena H. Ritchie. 1998. "Human Dentin Phosphophoryn Nucleotide and Amino Acid Sequence." *European Journal of Oral Sciences*. vol. 106, pp. 1043-1047.

Hartgerink, Jeffrey D., Thomas D. Clark, and M. Reza Ghadiri. 1998. "Peptide Nanotubes and Beyond." *Chem. Eur. J.* vol. 4, No. 8, pp. 1367-1372.

Johnstone, Brian, Thomas M. Hering, Arnold I. Caplan, Victor M. Goldberg, and Jung U. Yoo. 1998. "In Vitro Chondrogenesis of Bone Marrow-Derived Mesenchymal Progenitor Cells." *Experimental Cell Research*. vol. 238, pp. 265-272.

Kawasaki, M., A. Ohtomo, I. Ohkubo, H. Koinuma, Z. K. Tang, P. Yu, G. K. L. Wong, B. P. Zhang, and Y. Segawa. 1998. "Excitonic Ultraviolet Laser Emission at Room Temperature from Naturally Made Cavity in ZnO Nanocrytal Thin Films." *Materials Science and Engineering*. vol. B56, pp. 239-245.

Kogiso, Masaki, Satomi Ohnishi, Kiyoshi Yase, Mitsutoshi Masuda, and Toshimi Shimizu 1998. "Dicarboxylic Oligopeptide Bolaamphiphiles: Proton-Triggered Self-Assembly of Microtubes with Loose Solid Surfaces." *Langmuir*. vol. 14, No. 18, pp. 4978-4986, S1-S7.

Kogiso, Masaki, Takeshi Hanada, Kiyoshi Yase, and Toshimi Shimizu. 1998. "Intralayer Hydrogen-Bond-Directed Self-Assembly of Nano-Fibers from Dicarboxylic Valylvaline Bolaamphiphiles." *Chem. Comm.* pp. 1791-1792.

Li, Panjian and Paul Ducheyne. 1998. "Quasi-Biological Apatite Film Induced by Titanium in a Simulated Body Fluid." *Journal of Biomedical Materials Research*. vol. 41, pp. 341-348.

Nanci, A., J. D. Wuest, L. Peru, P. Brunet, V. Sharma, S. Zalzal, and M. D. McKee. 1998. "Chemical Modification of Titanium Surfaces for Covalent Attachment of Biological Molecules." *Journal of Biomedical Materials Research*. vol. 40, pp. 324-335.

Tsui, Y. C., C. Doyle, and T. W. Clyne. 1998. "Plasma Sprayed Hydroxyapatite Coatings on Titanium Substrates Part 2: Optimisation of Coating Properties." *Biomaterials*. vol. 19, pp. 2031-2043.

Weiner, S. and H. D. Wagner. 1998. "The Material Bone: Structure-Mechanical Function Relations." *Annu. Rev. Mater. Sci.* vol. 28, pp. 271-298.

Wen, H. B., J. R. de Wijn, F. Z. Cui, and K. de Groot. 1998. "Preparation of Calcium Phosphate Coatings on Titanium Implant Materials by Simple Chemistry." *Journal of Biomedical Materials Research*. vol. 41, pp. 227-236.

Wheeler, Donna L., David L. Chamberland, John M. Schmitt, David C. Buck, John H. Brekke, Jeffrey O. Hollinger, S.-P. Joh, and K.-W. Suh. 1998. "Radiomorphometry and Biomechanical Assessment of Recombinant Human Bone Morphogenetic Protein 2 and Polymer in Rabbit Radius Ostectomy Model." *Journal of Biomedical Materials Research (Appl. Biomater.)*. vol. 43, pp. 365-373.

Wolke, J. G. C., K. de Groot, and J. A. Jansen. 1998. "In Vivo Dissolution Behavior of Various RF Magnetron Sputtered Ca-P Coatings." *Journal of Biomedical Materials Research*. vol. 39, pp. 524-530.

Xiao, Shou-Jun, Marcus Textor, and Nicholas D. Spencer. 1998. "Covalent Attachment of Cell-Adhesive, (Arg-Gly-Asp)-Containing Peptides to Titanium Surfaces." *Langmuir*. vol. 14, No. 19, pp. 5507-5516.

Xu, Guofeng, Nan Yao, Ilhan A. Aksay, and John T. Groves. 1998. "Biomimetic Synthesis of Macroscopic-Scale Calcium Carbonate Thin Films. Evidence for a Multistep Assembly Process." *Journal of the American Chemical Society*. vol. 120, No. 46, pp. 11977-11985.

Yamada, Norihiro, Katsuhiko Ariga, Masanobu Naito, Kazuhiro Matsubara, and Emiko Koyama. 1998. "Regulation of β-Sheet Structures Within Amyloid-Like β-Sheet Assemblage from Tripeptide Derivatives." *Journal of the American Chemical Society*. vol. 120, No. 47, pp. 12192-12199.

Chusuei, Charles C., D. Wayne Goodman, Michael J. Van Stipdonk, Dina R. Justes, and Emile A. Schweikert. Jan. 1, 1999. "Calcium Phosphate Phase Identification Using XPS and Time-of-Flight Cluster SIMS." *Analytical Chemistry*. vol. 71, No. 1, pp. 149-153.

Zubarev, Eugene R., Martin U. Pralle, Leiming Li, and Samuel I. Stupp. Jan. 22, 1999. "Conversion of Supramolecular Clusters to Macromolecular Objects." *Science*. vol. 283, pp. 523-526.

Won, You-Yeon, H. Ted Davis, and Frank S. Bates. Feb. 12, 1999. "Giant Wormlike Rubber Micelles." *Science*. vol. 283, No. 5404, pp. 960-963.

Corral, Claudio J., Aamir Siddiqui, Liancun Wu, Catherine L. Farrell, David Lyons, and Thomas A. Mustoe. Feb. 1999. "Vascular Endothelial Growth Factor is More Important Than Basic Fibroblastic Growth Factor During Ischemic Wound Healing." *Arch. Surg.* vol. 134, pp. 200-205.

Wheeler, B. C., J. M. Corey, G. J. Brewer, and D. W. Branch. Feb. 1999. "Microcontact Printing for Precise Control of Nerve Cell Growth in Culture." *Journal of Biomechanical Engineering*. vol. 121, pp. 73-78.

Cao, H., Y. G. Zhao, S. T. Ho, E. W. Seelig, Q. H. Wang, and R. P. H. Chang. Mar. 15, 1999. "Random Laser Action in Semiconductor Powder." *Physical Review Letters*. vol. 82, No. 11, pp. 2278-2281.

Aizenberg, Joanna, Andrew J. Black, and George M. Whitesides. Apr. 8, 1999. "Control of Crystal Nucleation by Patterned Self-Assembled Monolayers." *Nature*. vol. 398, pp. 495-498.

Niklason, L. E., J. Gao, W. M. Abbott, K. K. Hirschi, S. Houser, R. Marini, and R. Langer. Apr. 16, 1999. "Functional Arteries Grown in Vitro." *Science*. vol. 284, pp. 489-493.

Hahn, Jungseok and Stephen E. Webber. Apr. 1999. "Modification of Surfaces by Covalent Attachment of Polymer Micelles." *Macromolecular Symposia*. vol. 139, pp. 39-47.

Liu, Yi, Duckhyun Kim, B. Timothy Himes, Stella Y. Chow, Timothy Schallert, Marion Murray, Alan Tessler, and Itzhak Fischer. Jun. 1, 1999. "Transplants of Fibroblasts Genetically Modified to Express BDNF Promote Regeneration of Adult Rat Rubrospinal Axons and Recovery of Forelimb Function." *The Journal of Neuroscience*. vol. 19, No. 11, pp. 4370-4387.

Mehler, Mark F. and John A. Kessler. Jul. 1999. "Progenitor Cell Biology: Implications for Neural Regeneration." *Arch. Neurol.* vol. 56, pp. 780-784.

Tirrell, M. Oct. 27, 1999. "Biofunctionalization of Surfaces with Peptide Amphiphiles." *AVS: Science & Technology*. Invited Paper BI-WeM7.

McDonald, John W., Xiao-Zhong Liu, Yun Qu, Su Liu, Shannon K. Mickey, Dorothy Turetsky, David I. Gottlieb, and Dennis W. Choi. Dec. 1999. "Transplanted Embryonic Stem Cells Survive, Differentiate and Promote Recovery in Injured Rat Spinal Cord." *Nature Medicine*. vol. 5, No. 12, pp. 1410-1412.

Bradt, Jens-Hilmar, Michael Mertig, Angelika Teresiak, and Wolfgang Pompe. 1999. "Biomimetic Mineralization of Collagen by Combined Fibril Assembly and Calcium Phosphate Formation." *Chem. Mater.* vol. 11, No. 10, pp. 2694-2701.

Braun, Paul V. and Samuel I. Stupp. 1999. "CdS Mineralization of Hexagonal, Lamellar, and Cubic Lyotropic Liquid Crystals." *Materials Research Bulletin*. vol. 34, No. 3, pp. 463-469.

Butler, C. E., I. V. Yannas, C. C. Compton, C. A. Correia, and D. P. Orgill. 1999. "Comparison of Cultured and Uncultured Keratinocytes Seeded into a Collagen-GAG Matrix for Skin Replacements." *British Journal of Plastic Surgery*. vol. 52, pp. 127-132.

Chai, C. S. and B. Ben-Nissan. 1999. "Bioactive Nanocrystalline Sol-Gel Hydroxyapatite Coatings." *Journal of Materials Science: Materials in Medicine*. vol. 10, pp. 465-469.

Clark, Thomas D., Kenji Kobayashi, and M. Reza Ghadiri. 1999. "Covalent Capture and Stabilization of Cylindrical β-Sheet Peptide Assemblies." *Chem. Eur. J.* vol. 5, No. 2, pp. 782-792.

Cornish, J., K. E. Callon, C. Q.-X. Lin, C. L. Xiao, T. B. Mulvey, G. J. S. Cooper, and I. R. Reid. 1999. "Trifluoroacetate, a Contaminant in Purified Proteins, Inhibits Proliferation of Osteoblasts and Chondrocytes." *Am. J Physiol. Endocrinol. Metab.* vol. 277, pp. 779-783.

Emoto, Kazunori, Yukio Nagasaki, and Kazunori Kataoka. 1999. "Coating of Surfaces with Stabilized Reactive Micelles from Poly(ethylene glycol)—Poly(DL-Lactic Acid) Block Copolymer." *Langmuir*. vol. 15, No. 16, pp. 5212-5218.

Fields, Gregg B. 1999. "Induction of Protein-like Molecular Architecture by Self-Assembly Processes." *Bioorganic & Medicinal Chemistry*. vol. 7, pp. 75-81.

Haynes, Andrew J., Wei-Qun Huang, Jamie Mallah, Dajun Yang, Marc E. Lippman, and Lu-Yuan Li. 1999. "Angiopoietin-1 and its Receptor Tie-2 Participate in the Regulation of Capillary-like Tubule Formation and Survival of Endothelial Cells." *Microvascular Research*. vol. 58, pp. 224-237.

Hwang, Julia J., Kevin Jaeger, James Hancock, and Samuel I. Stupp. 1999. "Organoapatite Growth on an Orthopedic Alloy Surface." *Journal of Biomedical Materials Research*. vol. 47, pp. 504-515.

Ignjatović, Nenad, Simonida Tornić, Momčilo Dakić, Miroslav Miljković, Milenko Plavšić, and Dragan Uskoković. 1999. "Synthesis and Properties of Hydroxyapatite/Poly-L-Lactide Composite Biomaterials." *Biomaterials*. vol. 20, pp. 809-816.

Lee, Kevin J. and Thomas M. Jessell. 1999. "The Specification of Dorsal Cell Fates in the Vertebrate Central Nervous System." *Annual Review of Neuroscience*. vol. 22, pp. 261-294.

Lee, Kyujin C., Paul A. Carlson, Alex S. Goldstein, Paul Yager, and Michael H. Gelb. 1999. "Protection of a Decapeptide from Proteolytic Cleavage by Lipidation and Self-Assembly into High-Axial-Ratio Microstructures: A Kinetic and Structural Study." *Langmuir*. vol. 15, No. 17, pp. 5500-5508.

Mao, Chuanbin, Hengde Li, Fuzhai Cui, Chunlai Ma, and Qinglin Feng. 1999. "Oriented Growth of Phosphates on Polycrystalline Titanium in a Process Mimicking Biomineralization." *Journal of Crystal Growth*. vol. 206, pp. 308-321.

Miyaji, Fumiaki, Hyun-Min Kim, Shinichi Handa, Tadashi Kokubo, and Takashi Nakamura 1999. "Bonelike Apatite Coating on Organic Polymers: Novel Nucleation Process Using Sodium Silicate Solution." *Biomaterials*. vol. 20, pp. 913-919.

Pakalns, Teika, Kraig L. Haverstick, Gregg B. Fields, James B. McCarthy, Daniel L. Mooradian, and Matthew Tirrell. 1999. "Cellular Recognition of Synthetic Peptide Amphiphiles in Self-Assembled Monolayer Films." *Biomaterials*. vol. 20, pp. 2265-2279.

Pittenger, Mark F., Alastair M. Mackay, Stephen C. Beck, Rama K. Jaiswal, Robin Douglas, Joseph D. Mosca, Mark A. Moorman, Donald W. Simonetti, Stewart Craig, and Daniel R. Marshak. Apr. 2, 1999. "Multilineage Potential of Adult Human Mesenchymal Stem Cells." *Science*. vol. 284, pp. 143-147.

Rezania, Alireza, Robert Johnson, Anthony R. Lefkow, and Kevin E. Healy. 1999. "Bioactivation of Metal Oxide Surfaces. 1. Surface Characterization and Cell Response." *Langmuir*. vol. 15, No. 20, pp. 6931-6939.

Rowley, Jon A., Gerard Madlambayan, and David J. Mooney. 1999. "Alginate Hydrogels as Synthetic Extracellular Matrix Materials." *Biomaterials*. vol. 20, pp. 45-53.

Schense, Jason C. and Jeffrey A. Hubbell. 1999. "Cross-Linking Exogenous Bifunctional Peptides into Fibrin Gels with Factor XIIIa." *Bioconjugate Chem*. vol. 10, No. 1, pp. 75-81.

Varma, H. K., Y. Yokogawa, F. F. Espinosa, Y. Kawamoto, K. Nishizawa, F. Nagata, and T. Kameyama. 1999. "In-Vitro Calcium Phosphate Growth over Functionalized Cotton Fibers." *Journal of Materials Science: Materials in Medicine*. vol. 10, pp. 395-400.

Vernon, Robert B. and E. Helene Sage. 1999. "A Novel, Quantitative Model for Study of Endothelial Cell Migration and Sprout Formation Within Three-Dimensional Collagen Matrices." *Microvascular Research*. vol. 57, pp. 188-133.

Wei, M., A. J. Ruys, M. V. Swain, S. H. Kim, B. K. Milthorpe, and C. C. Sorrell. 1999. "Interfacial Bond Strength of Electrophoretically Deposited Hydroxyapatite Coatings on Metals." *Journal of Materials Science: Materials in Medicine*. vol. 10, pp. 401-409.

Yagi, Nobuhiro, Yoshikatsu Ogawa, Masato Kodaka, Tomoko Okada, Takenori Tomohiro, Takeo Konakahara, and Hiroaki Okuno. 1999. "A Surface-Modified Functional Liposome Capable of Binding to Cell Membranes." *Chem. Commun*. pp. 1687-1688.

Yu, Ying-Ching, Vikram Roontga, Vladimir A. Daragan, Kevin H. Mayo, Matthew Tirrell, and Gregg B. Fields. 1999. "Structure and Dynamics of Peptide—Amphiphiles Incorporating Triple-Helical Proteinlike Molecular Architecture." *Biochemistry*. vol. 38, No. 5, pp. 1659-1668.

Huq, N. Laila, Keith J. Cross, and Eric C. Reynolds. Feb. 4, 2000. "Molecular Modelling of a Multiphosphorylated Sequence Motif Bound to Hydroxyapatite Surfaces." *Journal of Molecular Modeling*. vol. 6, pp. 35-47.

Martinez, J. S., G. P. Zhang, P. D. Holt, H. -T. Jung, C. J. Carrano, M. G. Haygood, and Alison Butler. Feb. 18, 2000. "Self-Assembling Amphiphilic Siderophores from Marine Bacteria." *Science*. vol. 287, No. 5456, pp. 1245-1247.

Verrecchio, Angela, Markus W. Germann, Barbara P. Schick, Brian Kung, Thomas Twardowski, and James D. San Antonio. Mar. 17, 2000. "Design of Peptides with High Affinities for Heparin and Endothelial Cell Proteoglycans." *The Journal of Biological Chemistry*. vol. 275, No. 11, pp. 7701-7707.

Cao, H., J. Y. Xu, E. W. Seelig, and R. P. H. Chang. May 22, 2000. "Microlaser Made of Disordered Media." *Applied Physics Letters*. vol. 76, No. 21, pp. 2997-2999.

Marler, Jennifer J., Amrita Guha, Jonathan Rowley, Rahul Koka, David Mooney, Joseph Upton, and Joseph Vacanti. May 2000. "Soft-Tissue Augmentation with Injectable Alginate and Syngeneic Fibroblasts." *Plastic and Reconstructive Surgery*. vol. 105, No. 6, pp. 2049-2058.

Holmes, Todd C., Sonsoles de Lacalle, Xing Su, Guosong Liu, Alexander Rich, and Shuguang Zhang. Jun. 6, 2000. "Extensive Neurite Outgrowth and Active Synapse Formation on Self-Assembling Peptide Scaffolds." *Proceedings of the National Academy of Sciences of the United States of America*. vol. 97, No. 12, pp. 6728-6733.

Whaley, Sandra R., D. S. English, Evelyn L. Hu, Paul F. Barbara, and Angela M. Belcher. Jun. 8, 2000. "Selection of Peptides with Semiconductor Binding Specificity for Directed Nanocrystal Assembly." *Nature*. vol. 405, pp. 665-668.

Sun, Xiu-xia and Chi-chen Wang. Jul. 28, 2000. "The N-Terminal Sequence (Residues 1-65) is Essential for Dimerization, Activities, and Peptide Binding of *Escherichia coli* DsbC." *The Journal of Biological Chemistry*. vol. 275, No. 30, pp. 22743-22749.

Hsu, Wei-Cherng, Mark H. Spilker, Ioannis V. Yannas, and Peter A. D. Rubin. Aug. 2000. "Inhibition of Conjunctival Scarring and Contraction by a Porous Collagen-Glycosaminoglycan Implant." *Investigative Ophthalmology & Visual Science*. vol. 41, No. 9, pp. 2404-2411.

Schlessinger, Joseph, Alexander N. Plotnikov, Omar A. Ibrahimi, Anna V. Eliseenkova, Brian K. Yeh, Avner Yayon, Robert J. Linhardt, and Moosa Mohammadi. Sep. 2000. "Crystal Structure of a Ternary FGF-FGFR-Heparin Complex Reveals a Dual Role for Heparin in FGFR Binding and Dimerization." *Molecular Cell*. vol. 6, pp. 743-750.

Sun, Y., J. B. Ketterson, and G. K. L. Wong. Oct. 9, 2000. "Excitonic Gain and Stimulated Ultraviolet Emission in Nanocrystalline Zinc-Oxide Powder." *Applied Physics Letters*. vol. 77, No. 15, pp. 2322-2324.

Schuldiner, Maya, Ofra Yanuka, Joseph Itskovitz-Eldor, Douglas A. Melton, and Nissim Benvenisty. Oct. 10, 2000. "Effects of Eight Growth Factors on the Differentiation of Cells Derived from Human Embryonic Stem Cells." *Proceedings of the National Academy of Sciences of the United States of America*. vol. 97, No. 21, pp. 11307-11312.

Altman, Michael, Peter Lee, Alexander Rich, and Shuguang Zhang. 2000. "Conformational Behavior of Ionic Self-Complementary Peptides." *Protein Science*. vol. 9, pp. 1095-1105.

Archer, Eric A., Noah T. Goldberg, Vincent Lynch, and Michael J. Krische. 2000. "Nanostructured Polymer Duplexes via the Covalent Casting of 1-Dimensional H-Bonding Motifs: A New Strategy for the Self-Assembly of Macromolecular Precursors." *Journal of the American Chemical Society*. vol. 122, No. 20, pp. 5006-5007.

Ariga, Katsuhiko, Jun-ichi Kikuchi, Masanobu Naito, Emiko Koyama, and Norihiro Yamada. 2000. "Modulated Supramolecular Assemblies Composed of Tripeptide Derivatives: Formation of Micrometer-Scale Rods, Nanometer-Size Needles, and Regular Patterns with Molecular-Level Flatness from the Same Compound." *Langmuir*. vol. 16, No. 11, pp. 4929-4939.

Beniash, E., W. Traub, A. Veis, and S. Weiner. 2000. "A Transmission Electron Microscope Study Using Vitrified Ice Sections of Predentin: Structural Changes in the Dentin Collagenous Matrix Prior to Mineralization." *Journal of Structural Biology*. vol. 132, pp. 212-225.

Bigi, Adriana, Elisa Boanini, Silvia Panzavolta, and Norberto Roveri. 2000. "Biomimetic Growth of Hydroxyapatite on Gelatin Films Doped with Sodium Polyacrylate." *Biomacromolecules*. vol. 1, No. 4, pp. 752-756.

Bourel, Line, Olivier Carion, Hélène Gras-Masse, and Oleg Melnyk. 2000. "The Deprotection of Lys(Mtt) Revisited." *Journal of Peptide Science*. vol. 6, pp. 264-270.

Caplan, Michael R., Peter N. Moore, Shuguang Zhang, Roger D. Kamm, and Douglas A. Lauffenburger. 2000. "Self-Assembly of a β-Sheet Protein Governed by Relief of Electrostatic Repulsion Relative to van der Waals Attraction." *Biomacromolecules*. vol. 1, No. 4, pp. 627-631.

Cardullo, F., M. Crego Calama, B. H. M. Snellink-Ruël, J.-L. Weidmann, A Bielejewska, R. Fokkens, N. M. M. Nibbering, P. Timmerman, and D. N. Reinhoudt. 2000. "Covalent Capture of Dynamic Hydrogen-Bonded Assemblies." *Chem. Commun*. pp. 367-368.

Chamberlain, L. J., I. V. Yannas, H-P. Hsu, G. R. Strichartz, and M. Spector. 2000. "Near-Terminus Axonal Structure and Function Following Rat Sciatic Nerve Regeneration Through a Collagen-GAG Matrix in a Ten-Millimeter Gap." *Journal of Neuroscience Research*. vol. 60, pp. 666-677.

David, Sunil A., Satish K. Awasthi, and P. Balaram. 2000. "The Role of Polar and Facial Amphipathic Character in Determining Lipopolysaccharide-Binding Properties in Synthetic Cationic Peptides." *Journal of Endotoxin Research*. vol. 6, No. 3, pp. 249-256.

Dori, Yoav, Havazelet Bianco-Peled, Sushil K. Satija, Gregg B. Fields, James B. McCarthy, and Matthew Tirrell. 2000. "Ligand Accessibility as Means to Control Cell Response to Bioactive Bilayer Membranes." *Journal of Biomedical Materials Research*. vol. 50, pp. 75-81.

Forns, Pilar, Janelle L. Lauer-Fields, Su Gao, and Gregg B. Fields. 2000. "Induction of Protein-Like Molecular Architecture by Monoalkyl Hydrocarbon Chains." *Biopolymers*. vol. 54, pp. 531-546.

Hisaeda, Yoshio, Eiji Ohshima, and Makiko Arimura. 2000. "Aggregation Behavior of Synthetic Peptide Lipids with Arginine in Aqueous Solution and Construction of a Vitamin $B_{12}$ Artifical Enzyme." *Colloids and Surfaces A: Physicochemical and Engineering Aspects*. vol. 169, pp. 143-153.

Kogiso, Masaki, Yuji Okada, Takeshi Hanada, Kiyoshi Yase, and Toshimi Shimizu. 2000. "Self-Assembled Peptide Fibers from Valylvaline Bola-Amphiphiles by a Parallel β-Sheet Network." *Biochimica et Biophysica Acta*. vol. 1475, pp. 346-352.

Langer, Robert. 2000. "Biomaterials in Drug Delivery and Tissue Engineering: One Laboratory's Experience." *Accounts of Chemical Research*. vol. 33, No. 2, pp. 94-101.

Liu, X. D., M. Skold, T. Umino, Y. K. Zhu, D. J. Romberger, J. R. Spurzem, and S. I. Rennard. 2000. "Endothelial Cell-Mediated Type I Collagen Gel Contraction is Regulated by Hemin." *J. Lab. Clin. Med.* vol. 136, No. 2, pp. 100-109.

Lu, Lichun, Susan J. Peter, Michelle D. Lyman, Hui-Lin Lai, Susan M. Leite, Janet A. Tamada, Shiro Uyama, Joseph P. Vacanti, Robert Langer, and Antonios G. Mikos. 2000. "In Vitro and in Vivo Degradation of Porous Poly(DL-Lactic-*co*-Glycolic Acid) Foams." *Biomaterials*. vol. 21, pp. 1837-1845.

Matsuura, T., R. Hosokawa, K. Okamoto, T. Kimoto, and Y. Akagawa. 2000. "Diverse Mechanisms of Osteoblast Spreading on Hydroxyapatite and Titanium." *Biomaterials*. vol. 21, pp. 1121-1127.

Mulloy, Barbara and Mark J. Forster. 2000. "Conformation and Dynamics of Heparin and Heparan Sulfate." *Glycobiology*. vol. 10, No. 11, pp. 1147-1156.

Ponticiello, Michael S., Robert M. Schinagl, Sudha Kadiyala, and Frank P. Barry. 2000. "Gelatin-Based Resorbable Sponge as a Carrier Matrix for Human Mesenchymal Stem Cells in Cartilage Regeneration Therapy." *Journal of Biomedical Materials Research*. vol. 52, pp. 246-255.

Powell, Sharon K., Jayashree Rao, Eva Roque, Motoyoshi Nomizu, Yuichiro Kuratomi, Yoshihiko Yamada, and Hynda K. Kleinman. 2000. "Neural Cell Response to Multiple Novel Sites on Laminin-1." *Journal of Neuroscience Research*. vol. 61, pp. 302-312.

Sakiyama-Elbert, Shelly E. and Jeffrey A. Hubbell. 2000. "Controlled Release of Nerve Growth Factor from a Heparin-Containing Fibrin-Based Cell Ingrowth Matrix." *Journal of Controlled Release*. vol. 69, pp. 149-158.

Sakiyama-Elbert, Shelly E. and Jeffrey A. Hubbell. 2000. "Development of Fibrin Derivatives for Controlled Release of Heparin-Binding Growth Factors." *Journal of Controlled Release*. vol. 65, pp. 389-402.

Thareja, R. K. and A. Mitra. 2000. "Random Laser Action in ZnO." *Appl. Phys*. vol. B 71, pp. 181-184.

Tunggal, Patrick, Neil Smyth, Mats Paulsson, and Mark-Christoph Ott. 2000. "Laminins: Structure and Genetic Regulation." *Microscopy Research and Technique*. vol. 51, pp. 214-227.

do Serro, Ana Paula Valagão Amadeu, Anabela Catarino Fernandes, and Benilde de Jesus Vieira Saramago. 2000. "Calcium Phosphate Deposition on Titanium Surfaces in the Presence of Fibronectin." *Journal of Biomedical Materials Research*. vol. 49, pp. 345-352.

Yamada, Norihiro and Katsuhiko Ariga. 2000. "Formation of β-Sheet Assemblage with a View to Developing an Amyloid Model." *Synlett*. vol. 5, pp. 575-586.

Yang, Lin and Paschalis Alexandridis. 2000. "Physicochemical Aspects of Drug Delivery and Release from Polymer-Based Colloids." *Current Opinion in Colloid & Interface Science*. vol. 5, pp. 132-143.

Yu, Huanran, Hiroshi Narusawa, Kisae Itoh, Akihiro Oshi, Narutoshi Yoshino, Kazuo Ohbu, Toshiaki Shirakawa, Kazuhiro Fukada, Masatoshi Fujii, Tadashi Kato, and Tsutomu Seimiya. 2000. "Hydrophilicity of Polar and Apolar Domains of Amphiphiles." *Journal of Colloid and Interface Science*. vol. 229, pp. 375-390.

Zhu, G., M. F. Mehler, P. C. Mabie, and J. A. Kessler. 2000. "Developmental Changes in Neural Progenitor Cell Lineage Commitment Do Not Depend on Epidermal Growth Factor Receptor Signaling." *Journal of Neuroscience Research*. vol. 59, pp. 312-320.

Jin, Young-Gu and K. J. Chang. Feb. 26, 2001. "Mechanism for the Enhanced Diffusion of Charged Oxygen Ions in $SiO_2$." *Physical Review Letters*. vol. 86, No. 9, pp. 1793-1796.

Orlic, Donald, Jan Kajstura, Stefano Chimenti, Igor Jakonuk, Stacie M. Anderson, Baosheng Li, James Pickel, Ronald McKay, Bernardo Nadal-Ginard, David M. Bodine, Annarosa Leri, and Piero Anversa. Apr. 5, 2001. "Bone Marrow Cells Regenerate Infarcted Myocardium." *Nature*. vol. 410, pp. 701-705.

Vailhé, Bruno, Daniel Vittet, and Jean-Jacques Feige. Apr. 2001. "In Vitro Models of Vasculogenesis and Angiogenesis." *Laboratory Investigation*. vol. 81, No. 4, pp. 439-452.

Davis, N. G., J. Teisen, C. Schuh, and D. C. Dunand. May 2001. "Solid-State Foaming of Titanium by Superplastic Expansion of Argon-Filled Pores." *J. Mater. Res.* vol. 16, No. 5, pp. 1508-1519.

Rabchevsky, Alexander G. and George M. Smith. May 2001. "Therapeutic Interventions Following Mammalian Spinal Cord Injury." *Arch. Neurol.* vol. 58, pp. 721-726.

Huang, Michael H., Samuel Mao, Henning Feick, Haoquan Yan, Yiying Wu, Hannes Kind, Eicke Weber, Richard Russo, and Peidong Yang. Jun. 8, 2001. "Room-Temperature Ultraviolet Nanowire Nanolasers." *Science*. vol. 292, pp. 1897-1899.

Lee, Kuen Yong and David J. Mooney. Jul. 2001. "Hydrogels for Tissue Engineering." *Chemical Reviews*. vol. 101, No. 7, pp. 1869-1879.

Aggeli, A., I. A. Nyrkova, M. Bell, R. Harding, L. Carrick, T. C. B. McLeish, A. N. Semenov, and N. Boden. Oct. 9, 2001. "Hierarchical Self-Assembly of Chiral Rod-Like Molecules as a Model for Peptide β-Sheet Tapes, Ribbons, Fibrils, and Fibers." *Proceedings of the National Academy of Sciences of the United States of America*. vol. 98, No. 21, pp. 11857-11862.

Hartgerink, Jeffrey D., Elia Beniash, and Samuel I. Stupp. Nov. 23, 2001. "Self-Assembly and Mineralization of Peptide-Amphiphile Nanofibers." *Science*. vol. 294, pp. 1684-1688.

Richardson, Thomas P., Martin C. Peters, Alessandra B. Ennett, and David J. Mooney. Nov. 2001. "Polymeric System for Dual Growth Factor Delivery." *Nature Biotechnology*. vol. 19, pp. 1029-1034.

Matsui, Hiroshi and Robert MacCuspie. Dec. 2001. "Metalloporphyrin Nanotube Fabrication Using Peptide Nanotubes as Templates." *Nano Letters*. vol. 1, No. 12, pp. 671-675.

Mathew, Mathai and Shozo Takagi. Nov.-Dec. 2001. "Structures of Biological Minerals in Dental Research." *Journal of Research of the National Institute of Standards and Technology*. vol. 106, No. 6, pp. 1035-1044.

Woo, Byung Ho, Betsy F. Fink, Richard Page, Jay A. Schrier, Yeong Woo Jo, Ge Jiang, Michelle DeLuca, Henry C. Vasconez, and Patrick P. DeLuca. Dec. 2001. "Enhancement of Bone Growth by Sustained Delivery of Recombinant Human Bone Morphogenetic Protein-2 in a Polymeric Matrix." *Pharmaceutical Research*. vol. 18, No. 12, pp. 1747-1753.

Barrère, F., P. Layrolle, C. A. Van Blitterswijk, and K. de Groot. 2001. "Biomimetic Coatings on Titanium: A Crystal Growth Study of Octacalcium Phosphate." *Journal of Materials Science: Materials in Medicine*. vol. 12, pp. 529-534.

Bianco-Peled, Havazelet, Yoav Dori, James Schneider, Li-Piin Sung, Sushil Satija, and Matthew Tirrell. 2001. "Structural Study of Langmuir Monolayers Containing Lipidated Poly(ethylene glycol) and Peptides." *Langmuir*. vol. 17, No. 22, pp. 6931-6937.

Cavalli, M., G. Gnappi, A. Montenero, D. Bersani, P. P. Lottici, S. Kaciulis, G. Mattogno, and M. Fini. 2001. "Hydroxy- and Fluorapatite Films on Ti Alloy Substrates: Sol-gel Preparation and Characterization." *Journal of Materials Science*. vol. 36, pp. 3253-3260.

Chang, John C., Gregory J. Brewer, and Bruce C. Wheeler. 2001. "Modulation of Neural Network Activity by Patterning." *Biosensors & Bioelectronics*. vol. 16, pp. 527-533.

Chang, Sophia C. N., Jon A. Rowley, Geoffrey Tobias, Nicholas G. Genes, Amit K. Roy, David J. Mooney, Charles A. Vacanti, and Lawrence J. Bonassar. 2001. "Injection Molding of Chondrocyte/Alginate Constructs in the Shape of Facial Implants." *Journal of Biomedical Materials Research*. vol. 55, pp. 503-511.

Doi, Tomokiyo, Takatoshi Kinoshita, Hiroki Kamiya, Shintaro Washizu, Yoshiharu Tsujita, and Hiraoki Yoshimizu. 2001. "Aggregation of Polypeptide-Based Amphiphiles in Water." *Polymer Journal*. vol. 33, No. 2, pp. 160-164.

Gore, Tushar, Yoav Dori, Yeshayahu Talmon, Matthew Tirrell, and Havazelet Bianco-Peled. 2001. "Self-Assembly of Model Collagen Peptide Amphiphiles." *Langmuir*. vol. 17, No. 17, pp. 5352-5360.

Hoess, Ronald H. 2001. "Protein Design and Phage Display." *Chemical Reviews*. vol. 101, No. 10, pp. 3205-3218.

Huang, Eric J. and Louis F. Reichardt. 2001. "Neurotrophins: Roles in Neuronal Development and Function." *Annual Review of Neuroscience*. vol. 24, pp. 677-736.

Irvine, Darrell J. and Anne M. Mayes. 2001. "Nanoscale Clustering of RGD Peptides at Surfaces Using Comb Polymers. 1. Synthesis and Characterization of Comb Thin Films." *Biomacromolecules*. vol. 2, No. 1, pp. 85-94.

Kam, L., W. Shain, J. N. Turner, and R. Bizios. 2001. "Axonal Outgrowth of Hippocampal Neurons on Micro-Scale Networks of Polylysine-Conjugated Laminin." *Biomaterials*. vol. 22, pp. 1049-1054.

Kikuchi, Masanori, Soichiro Itoh, Shizuko Ichinose, Kenichi Shinomiya, and Junzo Tanaka. 2001. "Self-Organization Mechanism in a Bone-Like Hydroxyapatite/Collagen Nancomposite Synthesized in Vitro and Its Biological Reaction in Vivo." *Biomaterials*. vol. 22, pp. 1705-1711.

Liu, Yuelian, Pierre Layrolle, Joost de Bruijn, Clemens van Blitterswijk, and Klaas de Groot. 2001. "Biomimetic Coprecipitation of Calcium Phosphate and Bovine Serum Albumin on Titanium Alloy." *Journal of Biomedical Materials Research*. vol. 57, pp. 327-335.

Look, D. C. 2001. "Recent Advances in ZnO Materials and Devices." *Materials Science and Engineering*. vol. B80, pp. 383-387.

Luo, Yi and Glenn D. Prestwich. 2001. "Novel Biomaterials for Drug Delivery." Expert Opin. Ther. Patents. vol. 11, No. 9, pp. 1395-1410.

Marchi-Artzner, Valerie, Barbara Lorz, Ulrike Hellerer, Martin Kantlehner, Horst Kessler, and Erich Sackmann 2001. "Selective Adhesion of Endothelial Cells to Artificial Membranes with a Synthetic RGD-Lipopeptide." *Chem. Eur. J.* vol. 7, No. 5, pp. 1095-1101.

Irvine, Darrell J. and Anne M. Mayes. 2001. "Nanoscale Clustering of RGD Peptides at Surfaces Using Comb Polymers. 1. Synthesis and Characterization of Comb Thin Films." *Biomacromolecules*. vol. 2, No. 1, pp. 85-94.

Matsui, Hiroshi, and Gary E. Douberly, Jr. 2001. "Organization of Peptide Nanotubes into Macroscopic Bundles." *Langmuir*. vol. 17, No. 25, pp. 7918-7922.

Matsui, Hiroshi, Precila Porrata, and Gary E. Douberly, Jr. 2001. "Protein Tubule Immobilization on Self-Assembled Monolayers on Au Substrates." *Nano Letters*. vol. 1, No. 9, pp. 461-464.

Neet, K. E. and R. B. Campenot. 2001. "Receptor Binding, Internalization, and Retrograde Transport of Neurotrophic Factors." *CMLS, Cell Mol. Life Sci.* vol. 58, pp. 1021-1035.

Otsuka, Hidenori, Yukio Nagasaki, and Kazunori Kataoka. 2001. "Self-Assembly of Poly(ethylene glycol)—based Block Copolymers for Biomedical Applications." *Current Opinion in Colloid & Interface Science*. vol. 6, pp. 3-10.

Shimizu, Toshimi, Rika Iwaura, Mitsutoshi Masuda, Takeshi Hanada, and Kiyoshi Yase. 2001. "Internucleobase-Interaction-Directed Self-Assembly of Nanofibers from Homo- and Heteroditopic 1,ω-Nucleobase Bolaamphiphiles." *Journal of the American Chemical Society*. vol. 123, No. 25, pp. 5947-5955, S1-S16.

Socrates, George. 2001. *Infrared and Raman Characteristic Group Frequencies: Tables and Charts*. Third Edition. Chichester, England: John Wiley & Sons Ltd.

Spanos, Nikos and Petros G. Koutsoukos. 2001. "Model Studies of the Effect of Orthophospho-L-Serine on Biological Mineralization." *Langmuir*. vol. 17, No. 3, pp. 866-872.

Takadama, Hiroaki, Hyun-Min Kim, Tadashi Kokubo, and Takashi Nakamura. 2001. "TEM-EDX Study of Mechanism of Bonelike Apatite Formation on Bioactive Titanium Metal in Simulated Body Fluid." *Journal of Biomedical Materials Research*. vol. 57, pp. 441-448.

Tanihara, Masao, Yasuo Suzuki, Eriko Yamamoto, Atsushi Noguchi, and Yutaka Mizushima. 2001. "Sustained Release of Basic Fibroblast Growth Factor and Angiogenesis in a Novel Covalently Crosslinked Gel of Heparin and Alginate." *Journal of Biomedical Materials Research*. vol. 56, pp. 216-221.

Torchilin, Vladimir P. 2001. "Structure and Design of Polymeric Surfactant-Based Drug Delivery Systems." *Journal of Controlled Release*. vol. 73, pp. 137-172.

Yeung, C. K., L. Lauer, A. Offenhäusser, and W. Knoll. 2001. "Modulation of the Growth and Guidance of Rat Brain Stem Neurons Using Patterned Extracellular Matrix Proteins." *Neuroscience Letters*. vol. 301, pp. 147-150.

Zubarev, Eugene R., Martin U. Pralle, Eli D. Sone, and Samuel I. Stupp. 2001. "Self-Assembly of Dendron Rodcoil Molecules into Nanoribbons." *Journal of the American Chemical Society*. vol. 123, No. 17, pp. 4105-4106.

Hirschi, Karen K., Lihua Lai, Narasimhaswamy S. Belaguli, David A. Dean, Robert J. Schwartz, and Warren E. Zimmer. Feb. 22, 2002. "Transforming Growth Factor-β Induction of Smooth Muscle Cell Phenotype Requires Transcriptional and Post-transcriptional Control of Serum Response Factor." *The Journal of Biological Chemistry*. vol. 277, No. 8, pp. 6287-6295.

Xu, Weiming, Lizhi Liu, and Ian G. Charles. Feb. 2002. "Microencapsulated iNOS-expressing Cells Cause Tumor Suppression in Mice." *The FASEB Journal*. vol. 16, pp. 213-215.

Zubarev, Eugene R., Martin U. Pralle, Eli D. Sone, and Samuel I. Stupp. Feb. 2002. "Scaffolding of Polymers by Supramolecular Nanoribbons." *Advanced Materials*. vol. 14, No. 3, pp. 198-203.

Slocik, Joseph M., Joshua T. Moore, and David W. Wright. Mar. 2002. Monoclonal Antibody Recognition of Histidine-Rich Peptide Encapsulated Nanoclusters. *Nano Letters*. vol. 2, No. 3, pp. 169-173.

Teng, Yang D., Erin B. Lavik, Xianlu Qu, Kook I. Park, Jitka Ourednik, David Zurakowski, Robert Langer, and Evan Y. Snyder. Mar. 5, 2002. "Functional Recovery Following Traumatic Spinal Cord Injury Mediated by a Unique Polymer Scaffold Seeded with Neural Stem Cells." *Proceedings of the National Academy of Sciences of the United States of America*. vol. 99, No. 5, pp. 3024-3029.

Bradbury, Elizabeth J., Lawrence D. F. Moon, Reena J. Popat, Von R. King, Gavin S. Bennett, Preena N. Patel, James W. Fawcett, and Stephen B. McMahon. Apr. 11, 2002. "Chondroitinase ABC Promotes Functional Recovery After Spinal Cord Injury." *Nature*. vol. 416, pp. 636-640.

Hartgerink, Jeffrey D., Elia Beniash, and Samuel I. Stupp. Apr. 16, 2002. "Supramolecular Chemistry and Self-Assembly Special Feature: Peptide-Amphiphile Nanofibers: A Versatile Scaffold for the Preparation of Self-Assembling Materials." *Proceedings of the National Academy of Sciences of the United States of America*. vol. 99, No. 8, pp. 5133-5138.

Vauthey, Sylvain, Steve Santoso, Haiyan Gong, Nicki Watson, and Shuguang Zhang. Apr. 16, 2002. "Molecular Self-Assembly of Surfactant-like Peptides to Form Nanotubes and Nanovesicles." *Proceedings of the National Academy of Sciences of the United States of America*. vol. 99, No. 8, pp. 5355-5360.

Nowak, Andrew P., Victor Breedveld, Lisa Pakstis, Bulent Ozbas, David J. Pine, Darrin Pochan, and Timothy J. Deming. May 23, 2002. "Rapidly Recovering Hydrogel Scaffolds from Self-Assembling Diblock Copolypeptide Amphiphiles." *Nature*. vol. 417, pp. 424-428.

GrandPré, Tadzia, Shuxin Li, and Stephen M. Strittmatter. May 30, 2002. "Nogo-66 Receptor Antagonist Peptide Promotes Axonal Regeneration." *Nature*. vol. 417, pp. 547-551.

Storch, Alexander and Johannes Schwarz. May 2002. "Neural Stem Cells and Neurodegeneration." *Current Opinion in Investigational Drugs*. vol. 3, No. 5, pp. 774-781.

Lendlein, Andreas and Robert Langer. May 31, 2002. "Biodegradable, Elastic Shape-Memory Polymers for Potential Biomedical Applications." *Science*. vol. 296, pp. 1673-1676.

Qiu, Jin, Dongming Cai, Haining Dai, Marietta McAttee, Paul N. Hoffman, Barbara S. Bregman, and Marie T. Filbin. Jun. 13, 2002. "Spinal Axon Regeneration Induced by Elevation of Cyclic AMP." *Neuron*. vol. 34, pp. 895-903.

Catledge, Shane A., Marc D. Fries, Yogesh K. Vohra, William R. Lacefield, Jack E. Lemons, Shanna Woodard, and Ramakrishna Venugopalan. Jun.-Aug. 2002. "Nanostructured Ceramics for Biomedical Implants." *Journal of Nanoscience and Nanotechnology*. vol. 2, No. 3/4, pp. 293-312.

Alsberg, Eben, Kenneth W. Anderson, Amru Albeiruti, Jon A. Rowley, and David J. Mooney. Sep. 17, 2002. "Engineering Growing Tissues." *Proceedings of the National Academy of Sciences of the United States of America.* vol. 99, No. 19, pp. 12025-12030.

Kay, Sarina, Anil Thapa, Karen M. Haberstroh, and Thomas J. Webster. Oct. 2002. "Nanostructured Polymer/Nanophase Ceramic Composites Enhance Osteoblast and Chondrocyte Adhesion." *Tissue Engineering.* vol. 8, No. 5, pp. 753-761.

Blight, Andrew R. Nov. 2002. "Miracles and Molecules—Progress in Spinal Cord Repair." Nature Neuroscience Supplement. vol. 5, pp. 1051-1054.

Chang, Hua, Chester W. Brown, and Martin M. Matzuk. Dec. 2002. "Genetic Analysis of the Mammalian Transforming Growth Factor-β Superfamily." *Endocrine Reviews.* vol. 23, No. 6, pp. 787-823.

Busqué, Felix, Stephanie A. Hopkins, and Joseph P. Konopelski. 2002. "Progress Toward a Peptidomimetic of Laminin-Derived Pentapeptide YIGSR: Synthesis of the Unique Tricyclic Core Structure." *J. Org. Chem.* vol. 67, No. 17, pp. 6097-6103.

Canaple, Laurence, Annemie Rehor, and David Hunkeler. 2002. "Improving Cell Encapsulation Through Size Control." *J. Biomater. Sci. Polymer Edn.* vol. 13, No. 7, pp. 783-796.

Caplan, Michael R., Elissa M. Schwartzfarb, Shuguang Zhang, Roger D. Kamm, and Douglas A. Lauffenburger. 2002. "Control of Self-Assembling Oligopeptide Matrix Formation Through Systematic Variation of Amino Acid Sequence." *Biomaterials.* vol. 23, pp. 219-227.

Chen, Zhi Jiang, Yvonne Ughrin, and Joel M. Levine. 2002. "Inhibition of Axon Growth by Oligodendrocyte Precursor Cells." *Molecular and Cellular Neuroscience.* vol. 20, pp. 125-139.

Cornish, Toby, Darren W. Branch, Bruce C. Wheeler, and James T. Campanelli. 2002. "Microcontact Printing: A Versatile Technique for the Study of Synaptogenic Molecules." *Molecular and Cellular Neuroscience.* vol. 20, pp. 140-153.

Costa, Silvia, Thierry Planchenault, Cecile Charriere-Bertrand, Yann Mouchel, Christiane Fages, Sharon Juliano, Thierry Lefrançois, Georgia Barlovatz-Meimon, and Marcienne Tardy. 2002. "Astroglial Permissivity for Neuritic Outgrowth in Neuron-Astrocyte Cocultures Depends on Regulation of Laminin Bioavailability." *GLIA.* vol. 37, pp. 105-113.

Gariépy, Jean, Sandrine Rémy, Xiuguo Zhang, James R. Ballinger, Eleonora Bolewska-Pedyczak, Michael Rauth, and Stuart K. Bisland. 2002. "A Simple Two-Step Approach for Introducing a Protected Diaminedithiol Chelator During Solid-Phase Assembly of Peptides." *Bioconjugate Chem.* vol. 13, No. 3, pp. 679-684.

Glättli, Alice, Xavier Daum, Dieter Seebach, and Wilfred F. van Gunsteren. 2002. "Can One Derive the Confrontational Preference of a β-Peptide from Its CD Spectrum?" *Journal of the American Chemical Society.* vol. 124, No. 44, pp. 12972-12978.

Gutwein, Luke G. and Thomas J. Webster. 2002. "Osteoblast and Chrondrocyte Proliferation in the Presence of Alumina and Titania Nanoparticles." *Journal of Nanoparticle Research.* vol. 4, pp. 231-238.

Huang, Ning-Ping, Gabor Csucs, Kazunori Emoto, Yukio Nagasaki, Kazunori Kataoka, Marcus Textor, and Nicholas D. Spencer. 2002. "Covalent Attachment of Novel Poly(ethylene glycol)—Poly(DL-lactic acid) Copolymeric Micelles to $TiO_2$ Surfaces." *Langmuir.* vol. 18, No. 1, pp. 252-258.

Issac, Roy and Jean Chmielewski. 2002. "Approaching Exponential Growth with a Self-Replicating Peptide." *Journal of the American Chemical Society.* vol. 124, No. 24, pp. 6808-6809.

Joshi, Mital and Michael G. Fehlings. 2002. "Development and Characterization of a Novel, Graded Model of Clip Compressive Spinal Cord Injury in the Mouse: Part 1. Clip Design, Behavioral Outcomes, and Histopathology." *Journal of Neurotrauma.* vol. 19, No. 2, pp. 175-190.

Joshi, Mital and Michael G. Fehlings. 2002. "Development and Characterization of a Novel, Graded Model of Clip Compressive Spinal Cord Injury in the Mouse: Part 2. Quantitative Neuroanatomical Assessment and Analysis of the Relationships Between Axonal Tracts, Residual Tissue, and Locomotor Recovery." *Journal of Neurotrauma.* vol. 19, No. 2, pp. 191-203.

Kruger, Ryan G., Patrick Dostal, and Dewey G. McCafferty. 2002. "An Economical and Preparative Orthogonal Solid Phase Synthesis of Fluorescein and Rhodamine Derivatized Peptides: FRET Substrates for the *Staphylococcus aureus* Sortase SrtA Transpeptidase Reaction." *Chem. Commun.* pp. 2092-2093.

Lauer, L., A. Vogt, C. K. Yeung, W. Knoll, and A. Offenhäusser. 2002. "Electrophysiological Recordings of Patterned Rat Brain Stem Slice Neurons." *Biomaterials.* vol. 23, pp. 3123-3130.

Lavik, Erin, Yang D. Teng, Evan Snyder, and Robert Langer. 2002. "Speeding Neural Stem Cells on Scaffolds of PGA, PLA, and Their Copolymers." *Methods in Molecular Biology: Neural Stem Cells: Methods and Protocols.* vol. 198, pp. 89-97.

Marini, Davide M., Wonmuk Hwang, Douglas A. Lauffenburger, Shuguang Zhang, and Roger D. Kamm. 2002. "Left-Handed Helical Ribbon Intermediates in the Self-Assembly of a β-Sheet Peptide." *Nano Letters.* vol. 2, No. 4, pp. 295-299.

Ohsaki, Mio, Tatsuya Okuda, Akihiro Wada, Toshiya Hirayama, Takuro Niidome, and Haruhiko Aoyagi. 2002. "In Vitro Gene Transfection Using Dendritic Poly(L-lysine)." *Bioconjugate Chem.* vol. 13, No. 3, pp. 510-517.

Okano, Hideyuki. 2002. "Stem Cell Biology of the Central Nervous System." *Journal of Neuroscience Research.* vol. 69, pp. 698-707.

Parmar, Malin, Charlotta Skogh, Anders Björklund, and Kenneth Campbell. 2002. "Regional Specification of Neurosphere Cultures Derived from Subregions of the Embryonic Telencephalon." *Molecular and Cellular Neuroscience.* vol. 21, pp. 645-656.

Porter, A. E., L. W. Hobbs, V. Benezra Rosen, and M. Spector. 2002. "The Ultrastructure of the Plasma-Sprayed Hydroxyapatite-bone Interface Predisposing to Bone Bonding." *Biomaterials.* vol. 23, pp. 725-733.

Rodger, Alison, Jascindra Rajendra, Rachel Marrington, Malin Ardhammar, Bengt Norden, Jonathan D. Hirst, Andrew T. B. Gilbert, Timothy R. Dafforn, David J. Halsall, Cheryl A. Woolhead, Colin Robinson, Teresa J. T. Pinheiro, Jurate Kazlauskaite, Mark Seymour, Niuvis Perez, and Michael J. Hannon. 2002. "Flow Oriented Linear Dichroism to Probe Protein Orientation in Membrane Environments." *Phys. Chem. Chem. Phys.* vol. 4, pp. 4051-4057.

Rowley, Jon A. and David J. Mooney. 2002. "Alginate Type and RGD Density Control Myoblast Phenotype." *Journal of Biomedical Materials Research.* vol. 60, pp. 217-223.

Santoso, Steve S., Sylvain Vauthey, and Shuguang Zhang. 2002. "Structures, Function and Applications of Amphiphilic Peptides." *Current Opinion in Colloid & Interface Science.* vol. 7, pp. 262-266.

Shih, Sheng-Ming, Wei-Fang Su, Yuh-Jiuan Lin, Cen-Shawn Wu, and Chii-Dong Chen. 2002. "Two-Dimensional Arrays of Self-Assembled Gold and Sulfur-Containing Fullerene Nanoparticles." *Langmuir.* vol. 18, No. 8, pp. 3332-3335.

Thiébaud, Pierre, Lars Lauer, Wolfgang Knoll, and Andreas Offenhäuser. 2002. "PDMS Device for Patterned Application of Microfluids to Neuronal Cells Arranged by Microcontact Printing." *Biosensors & Bioelectronics.* vol. 17, pp. 87-93.

Tryoen-Tóth, Petra, Dominique Vautier, Youssef Haikel, Jean-Claude Voegel, Pierre Schaaf, Johanna Chluba, and Joëlle Ogier. 2002. "Viability, Adhesion, and Bone Phenotype of Osteoblast-like Cells on Polyelectrolyte Multilayer Films." *Journal of Biomedical Materials Research.* vol. 60, pp. 657-667.

Wong, Michael S., Jennifer N. Cha, Kyoung-Shin Choi, Timothy J. Deming, and Galen D. Stucky. 2002. "Assembly of Nanoparticles into Hollow Spheres Using Block Copolypeptides." *Nano Letters.* vol. 2, No. 6, pp. 583-587.

Young, Wise. 2002. "Spinal Cord Contusion Models." *Progress in Brain Research.* vol. 137, pp. 231-255.

Bruggeman, Holger, Sebastian Baumer, Wolfgang Florian Fricke, Arnim Wiezer, Heiko Liesegang, Iwona Decker, Christina Herzberg, Rosa Martinez-Arias, Rainer Merkl, Anke Henne, and Gerhard Gottschalk. Feb. 4, 2003. "The Genome Sequence of *Clostridium tetani*, the Causative Agent of Tetanus Disease." *PNAS.* vol. 100, No. 3, pp. 1316-1321.

Lutolf, Matthias P., Franz E. Weber, Hugo G. Schmoekel, Jason C. Schense, Thomas Kohler, Ralph Müller, and Jeffrey A. Hubbell. May 2003. "Repair of Bone Defects Using Synthetic Mimetics of Collagenous Extracellular Matrices." *Nature Biotechnology.* vol. 21, pp. 513-518.

Shaw, Derek and Molly S. Shoichet. May 2003. "Toward Spinal Cord Injury Repair Strategies: Peptide Surface Modification of Expanded Poly(Tetrafluoroethylene) Fibers for Guided Neurite Outgrowth in Vitro." *The Journal of Craniofacial Surgery*. vol. 14, No. 3, pp. 308-316.

Silva, G. A., K. L. Kehl, K. L. Niece, and S. I. Stupp. May 4, 2003. "Nanoengineered Peptide Amphiphile Network for Photoreceptor Replacement in Degenerative Retinal Disorders." Investigative Ophthalmology & Visual Science. Abstract No. 492 from Annual Meeting of the Association for Research in Vision and Opthalmology.

Cheng, Hongwei, Wei Jiang, Frank M. Phillips, Rex C. Haydon, Ying Peng, Lan Zhou, Hue H. Luu, Naili An, Benjamin Breyer, Pantila Vanichakarn, Jan Paul Szatkowski, Jae Yoon Park, and Tong-Chuan He. Aug. 2003. "Osteogenic Activity of the Fourteen Types of Human Bone Morphogenetic Proteins (BMPs)." *The Journal of Bone & Joint Surgery*. vol. 85-A, No. 8, pp. 1544-1552, 141.

Arinzeh, Treena Livingston, Susan J. Peter, Michael P. Archambault, Christian van den Bos, Steve Gordon, Karl Kraus, Alan Smith, and Sudha Kadiyala. Oct. 2003. "Allogeneic Mesenchymal Stem Cells Regenerate Bone in a Critical-Sized Canine Segmental Defect." *The Journal of Bone & Joint Surgery*. vol. 85-A, No. 10, pp. 1927-1935.

Zhang, Shuguang. Oct. 2003. "Fabrication of Novel Biomaterials Through Molecular Self-Assembly." *Nature Biotechnology*. vol. 21, No. 10, pp. 1171-1178.

Aggeli, Amalia, Mark Bell, Lisa M. Carrick, Colin W. G. Fishwick, Richard Harding, Peter J. Mawer, Sheena E. Radford, Andrew E. Strong, and Neville Boden. 2003. "pH as a Trigger of Peptide β-Sheet Self-Assembly and Reversible Switching Between Nematic and Isotropic Phases." *Journal of the American Chemical Society*. vol. 125, No. 32, pp. 9619-9628.

Alsina, Jordi and Fernando Albericio. 2003. "Solid-Phase Synthesis of C-Terminal Modified Peptides." *Biopolymers (Peptide Science)*. vol. 71, pp. 454-477.

Anthony, Shawn G. 2003. "Injectable Biomaterials for Bone Tissue Engineering."

Boontheekul, Tanyarut and David J. Mooney. 2003. "Protein-Based Signaling Systems in Tissue Engineering." *Current Opinion in Biotechnology*. vol. 14, pp. 559-565.

Brandenburg, Klaus, Frauke Wagner, Mareike Muller, Holger Heine, Jorg Andra, Michel H. J. Koch, Ulrich Zahringer, and Ulrich Seydel. 2003. "Physicochemical Characterization and Biological Activity of a Glycoglycerolipid from *Mycoplasma* fermentans." Eur. J. Biochem. vol. 270, pp. 3271-3279.

Czeisler, C., V. M. Tysseling-Mattiace, G. A. Silva, S. I. Stupp, and J. A. Kessler. 2003. "Behavoral Improvement and Increased Survival Rate after Treatment with a Self Assembling Gel in a Rat Model of Spinal Cord Injury." 2003 Abstract Viewer/Itinerary Planner. Program No. 245.22. Washington, DC: Society for Neuroscience. Printed Feb. 5, 2007. p. 1. http://sfn.scholarone.com/itin2003/main.html?new_page_id=126&abstract_id=1554....

Fauza, Dario O. 2003. "Tissue Engineering: Current State of Clinical Application." *Current Opinion in Pediatrics*. vol. 15, pp. 267-271.

Ganesh, S. and R. Jayakumar. 2003. "Structural Transitions Involved in a Novel Amyloid-Like β-Sheet Assemblage of Tripeptide Derivatives." *Biopolymers*. vol. 70, pp. 336-345.

Ganesh, S., S. Prakash, and R. Jayakumar. 2003. "Spectroscopic Investigation on Gel-Forming β-Sheet Assemblage of Peptide Derivatives." *Biopolymers*. vol. 70, pp. 346-354.

Gergely, C. S., P. Bar Yosef, R. Govrin-Lippman, F. Cuisinier, and H. Füredi-Milhofer. 2003. "The Deposition of Calcium Phosphates Within Polyelectrolyte Multilayer Films." *Key Engineering Materials*. vols. 240-242 (Bioceramics), pp. 287-290.

Goeden-Wood, Nichole L., Jay D. Keasling, and Susan J. Muller. 2003. "Self-Assembly of a Designed Protein Polymer into β-Sheet Fibrils and Responsive Gels." *Macromolecules*. vol. 36, No. 8, pp. 2932-2938.

Ishihara, Masayuki, Kiyohaya Obara, Toshiaki Ishizuka, Masanori Fujita, Masato Sato, Kazunori Masuoka, Yoshio Saito, Hirofumi Yura, Takemi Matsui, Hidemi Hattori, Makoto Kikuchi, and Akira Kurita. 2003. "Controlled Release of Fibroblast Growth Factors and Heparin from Photocrosslinked Chitosan Hydrogels and Subsequent Effect on in Vivo Vascularization." *Journal of Biomedical Materials Research*. vol. 64A, pp. 551-559.

Malkar, Navdeep B., Janette L. Lauer-Fields, Darius Juska, and Gregg B. Fields. 2003. "Characterization of Peptide-Amphiphiles Possessing Cellular Activation Sequences." *Biomacromolecules*. vol. 4, No. 3, pp. 518-528.

Niece, Krista L., Jeffrey D. Hartgerink, Jack J. J. M. Donners, and Samuel I. Stupp. 2003. "Self-Assembly Combining Two Bioactive Peptide-Amphiphile Molecules into Nanofibers by Electrostatic Attraction." *Journal of the American Chemical Society*. vol. 125, No. 24, pp. 7146-7147.

Pavlov, Georges, Stephanie Finet, Karine Tatarenko, Evgueniya Komeeva, and Christine Ebel. 2003. "Conformation of Heparin Studied with Macromolecular Hydrodynamic Methods and X-ray Scattering." *Eur. Biophys. J.* vol. 32, pp. 437-449.

Schmidt, Christine E. and Jennie Baier Leach. 2003. "Neural Tissue Engineering: Strategies for Repair and Regeneration." Annu. Rev. Biomed. Eng. vol. 5, pp. 293-347.

Steward, Oswald, Binhai Zheng, and Marc Tessier-Lavigne. 2003. "False Resurrections: Distinguishing Regenerated from Spared Axons in the Injured Central Nervous System." *The Journal of Comparative Neurology*. vol. 459, pp. 1-8.

t' Hart, Bert A. and Sandra Amor. 2003. "The Use of Animal Models to Investigate the Pathogenesis of Neuroinflammatory Disorders of the Central Nervous System." Current Opinion in Neurology. vol. 16, pp. 375-383.

Wu, Sufan, Yoshihisa Suzuki, Yoko Ejiri, Toru Noda, Hongliang Bai, Masaaki Kitada, Kazuya Kataoka, Masayoshi Ohta, Hirotomi Chou, and Chizuka Ide. 2003. "Bone Marrow Stromal Cells Enhance Differentiation of Cocultured Neurosphere Cells and Promote Regeneration of Injured Spinal Cord." *Journal of Neuroscience Research*. vol. 72, pp. 343-351.

Yamada, Norihiro, Tsukasa Komatsu, Hirotsugu Yoshinaga, Kayo Yoshizawa, Susumu Edo, and Masashi Kunitake. 2003. "Self-Supporting Elastic Film without Covalent Linkages as a Hierarchically Integrated β-Sheet Assembly." Angew. Chem. Int. Ed. Vol. 42, pp. 5496-5499.

Zhang, Yan, Hongwei Gu, Zhimou Yang, and Bing Xu. 2003. "Supramolecular Hydrogels Respond to Ligand-Receptor Interaction." *Journal of the American Chemical Society*. vol. 125, No. 45, pp. 13680-13681.

Hirano, Yoshiaki and David J. Mooney. Jan. 5, 2004. "Peptide and Protein Presenting Materials for Tissue Engineering." *Advanced Materials*. vol. 16, No. 1, pp. 17-25.

Silva, Gabriel A., Catherine Czeisler, Krista L. Niece, Elia Beniash, Daniel A Harrington, John A. Kessler, and Samuel I. Stupp. Feb. 27, 2004. "Selective Differentiation of Neural Progenitor Cells by High-Epitope Density Nanofibers." *Science*. vol. 303, pp. 1352-1355.

Faulkner, Jill R., Julia E. Herrmann, Michael J. Woo, Keith E. Tansey, Ngan B. Doan, and Michael V. Sofroniew. Mar. 3, 2004. "Reactive Astrocytes Protect Tissue and Preserve Function after Spinal Cord Injury." *The Journal of Neuroscience*. vol. 24, No. 9, pp. 2143-2155.

Cao, Renhai, Anna Eriksson, Hajime Kubo, Kari Alitalo, Yihai Cao, Johan Thyberg. Mar. 19, 2004. "Comparative Evaluation of FGF-2-, VEGF-A-, and VEGF-C-Induced Angiogenesis, Lymphangiogenesis, Vascular Fenestrations, and Permeability." *Circulation Research*. vol. 94, pp. 664-670.

Anthony, Shawn G. Mar. 28-Apr. 1, 2004. "Self-Assembling Nanofiber Matrix for Bone Regeneration." *The 227th ACS National Meeting*. Anaheim, CA.

Donners, Jack J. J. M. Mar. 28-Apr. 1, 2004. "Growth Factor Binding Self-Assembling Nanofiber Networks for Tissue Regeneration." *The 227th ACS National Meeting*. Anaheim, CA.

Nikulina Elena, J. Lille Tidwell, Hai Ning Dai, Barbara S. Bregman, and Marie T. Filbin. Jun. 8, 2004. "The Phosphodiesterase Inhibitor Rolipram Delivered after a Spinal Cord Lesion Promotes Axonal Regeneration and Functional Recovery." *Proceedings of the National Academy of Sciences of the United States of America*. vol. 101, No. 23, pp. 8786-8790.

Pearse, Damien D., Francisco C. Pereira, Alexander E. Marcillo, Margaret L. Bates, Yerko A. Berrocal, Marie T. Filbin, and Mary Bartlett Bunge. Jun. 2004. "cAMP and Schwann Cells Promote Axonal Growth and Functional Recovery After Spinal Cord Injury." *Nature Medicine*. vol. 10, No. 6, pp. 610-616.

Lu, Paul, Hong Yang, Leonard L. Jones, Marie T. Filbin, and Mark H. Tuszynski. Jul. 14, 2004. "Combinatorial Therapy with Neurotrophins and cAMP Promotes Axonal Regeneration beyond Sites of Spinal Cord Injury." *The Journal of Neuroscience*. vol. 24, No. 28, pp. 6402-6409.

Lee, K. W., J. J. Yoon, J. H. Lee, S. Y. Kim, H. J. Jung, S. J. Kim, J. W. Joh, H. H. Lee, D. S. Lee, and S. K. Lee. 2004. "Sustained Release of Vascular Endothelial Growth Factor From Calcium-Induced Alginate Hydrogels Reinforced by Heparin and Chitosan." *Transplantation Proceedings*. vol. 36, pp. 2464-2465.

Matsumura, Sachiko, Shinobu Uemura, and Hisakazu Mihara. 2004. "Fabrication of Nanofibers with Uniform Morphology by Self-Assembly of Designed Peptides." *Chem. Eur. J.* vol. 10, pp. 2789-2794.

Sieminski, A. L., R. P. Hebbel, and K. J. Gooch. 2004. "The Relative Magnitudes of Endothelial Force Generation and Matrix Stiffness Modulate Capillary Morphogenesis in Vitro." *Experimental Cell Research*. vol. 297, pp. 574-584.

Vandermeulen, Guido W. M. and Harm-Anton Klok. 2004. "Peptide/Protein Hybrid Materials: Enhanced Control of Structure and Improved Performance through Conjugation of Biological and Synthetic Polymers." *Macromolecular Bioscience*. vol. 4, pp. 383-398.

Wang, Lin-Fa and Meng Yu. 2004. "Epitope Identification and Discovery Using Phage Display Libraries: Applications in Vaccine Development and Diagnostics." *Current Drug Targets*. vol. 5, No. 1, pp. 1-15.

Sayle, Roger. Printed Nov. 9, 2005. "Physiological Ionization and pKa Prediction." http://www.daylight.com/meetings/emug00/Sayle/pkapredict.html. pp. 1-13.

Beniash, Elia, Jeffery D. Hartgerink, Hannah Storrie, John C. Stendahl, and Samuel I. Stupp. 2005. "Self-Assembling Peptide Amphiphile Nanofiber Matrices for Cell Entrapment." *Acta Biomaterialia*. vol. 1, pp. 387-397.

Bull, Steve R., Mustafa O. Guler, Rafael E. Bras, Thomas J. Meade, and Samuel I. Stupp. 2005. "Self-Assembled Peptide Amphiphile Nanofibers Conjugated to MRI Contrast Agents." *Nano Letters*. vol. 5, No. 1, pp. 1-4.

Guler, Mustafa O., Stephen Soukasene, James F. Hulvat, and Samuel I. Stupp. 2005. "Presentation and Recognition of Biotin on Nanofibers Formed by Branched Peptide Amphiphiles." *Nano Letters*. vol. 5, No. 2, pp. 249-252.

Knake, Rene, Amir W. Fahmi, Syed A. M. Tofail, Jason Clohessy, Miroslav Mihov, and Vincent J. Cunnane. 2005. "Electrochemical Nucleation of Gold Nanoparticles in a Polymer Film at a Liquid-Liquid Interface." *Langmuir*. vol. 21, No. 3, pp. 1001-1008.

Loudon, M. "Amino Acid Structures at Physiological pH." Printed Jun. 5, 2006. www.brynmawr.edu/Acads/Chem/mnerzsto/amino_acids.htm, amino_acids_2.gif, and amino_acids3.htm.

Hoke, Ahmet. Aug. 2006. "Mechanisms of Disease: What Factors Limit the Success of Peripheral Nerve Regeneration in Humans?" *Nature Clinical Practice Neurology*. vol. 2, No. 8, pp. 448-454.

Kokkoli, Efrosini, Anastasia Mardilovich, Alison Wedekind, Emilie L. Rexeisen, Ashish Garg, and Jennifer A. Craig. 2006. "Self-Assembly and Applications of Biomimetic and Bioactive Peptide-Amphiphiles." Soft Matter. vol. 2, pp. 1015-1024.

"AccessScience Search Results. Amphiphile." Accessed online May 7, 2007. http://www.accessscience.com/search/asearch?location=titlestext&newSearch=1&pubpriv=private&categories=dictionary&categval=dictionary&text=amphiphile. McGraw-Hill Encyclopedia of Science & Technology Online.

The LabRat.com. 2007, updated. Hank's Buffered Salt Solution (HBSS) Recipe. http://www.thelabrat.com/protocolsHanks.shtml. Printed Jan. 19, 2007. pp. 1-2.

Invitrogen. Printed Jan. 22, 2008. "Dulbecco's Modified Eagle Medium (D-MEM) (1X) Liquid (High Glucose)." http://www.invitrogen.com/content.cfm?pageId=95&fuseaction=MediaForm.dsp_mediaForm&productId....

Uniprot entry for Q899Z6. Printed Mar. 14, 2008. http://www.pir.uniprot.org/cgi-bin/upEntry?id=Q899Z6_CLOTE. 3 pages.

Kibbey, Maura C., Mathias Jucker, Benjamin S. Weeks, Rachael L. Neve, Wiliam E. Van Nostrand, and Hynda K. Kleinman. Nov. 1993. "β-Amyloid Precursor Protein Binds to the Neurite-Promoting IKVAV Site of Laminin." *Proc. Natl. Acad. Sci. U.S.A.* vol. 90, pp. 10150-10153.

Oka, Kazunari, Masaaki Yamamoto, Toshiharu Nonaka, and Masamichi Tomonaga. Apr. 1996. "The Significance of Artificial Cerebrospinal Fluid as Perfusate and Endoneurosurgery." Neurosurgery Online. vol. 38, No. 4, pp. 733-736.

Rapaport, Hanna, Kristian Kjaer, Torben R. Jensen, Leslie Leiserowitz, and David A. Tirrell. 2000. "Two-Dimensional Order in β-Sheet Peptide Monolayers." Journal of the American Chemical Society. vol. 122, No. 50, pp. 12523-12529.

Avrahami, Dorit and Yechiel Shai. 2002. "Conjugation of a Magainin Analogue with Lipophilic Acids Controls Hydrophobicity, Solution Assembly, and Cell Selectivity." Biochemistry. vol. 41, No. 7, pp. 2254-2263.

Yamada, Masanori, Yuichi Kadoya, Shingo Kasai, Kozue Kato, Mayumi Mochizuki, Norio Nishi, Nobuhisa Watanabe, Hynda K. Kleinman, Yoshihiko Yamada, and Motoyoshi Nomizu. 2002. "Ile-Lys-Val-Ala-Val (IKVAV)-Containing Laminin α1 Chain Peptides Form Amyloid-like Fibrils." FEBS Letters. vol. 530, pp. 48-52.

McGregor, Clare-Louise, Lu Chen, Neil C. Pomroy, Peter Hwang, Sandy Go, Avijit Chakrabartty, and Gilbert G. Privé. Feb. 2003. "Lipopeptide Detergents Designed for the Structural Study of Membrane Proteins." Nature Biotechnology. vol. 21, pp. 171-176.

Ohmori, Hideya, Yasumitsu Sato, and Akiyoshi Namiki. 2004. "The Anticonvulsant Action of Propofol on Epileptiform Activity in Rat Hippocampal Slices." Anesth. Analg. vol. 99, pp. 1095-1101.

Shahraki, Ali and Trevor W. Stone. 2004. "Blockade of Presynaptic Adenosine A1 Receptor Responses by Nitric Oxide and Superoxide in Rat Hippocampus." European Journal of Neuroscience. vol. 20, pp. 719-728.

Sone, Eli D. and Samuel I. Stupp. 2004. "Semiconductor-Encapsulated Peptide-Amphiphile Nanofibers." Journal of the American Chemical Society. vol. 126, No. 40, pp. 12756-12757.

Smith, L. A. and P. X. Ma. 2004. "Nano-Fibrous Scaffolds for Tissue Engineering." Colloids and Surfaces. B: Biointerfaces. vol. 39, pp. 125-131.

Tsonchev, Stefan, George C. Schatz, and Mark A. Ratner. 2004. "Electrostatically-Directed Self-Assembly of Cylindrical Peptide Amphiphile Nanostructures." J. Phys. Chem. B. vol. 108, No. 26, pp. 8817-8822.

Tsonchev, Stefan, Alessandro Troisi, George C. Schatz, and Mark A. Ratner. 2004. "All-Atom Numerical Studies of Self-Assembly of Zwitterionic Peptide Amphiphiles." J. Phys. Chem. B. vol. 108, No. 39, pp. 15278-15284.

Tsonchev, Stefan, Alessandro Troisi, George C. Schatz, and Mark A. Ratner. 2004. "On the Structure and Stability of Self-Assembled Zwitterionic Peptide Amphiphiles: A Theoretical Study." Nano Letters. vol. 4, No. 3, pp. 427-431.

Arnold, Michael S., Mustafa O. Guler, Mark C. Hersam, and Samuel I. Stupp. 2005. "Encapsulation of Carbon Nanotubes by Self-Assembling Peptide Amphiphiles." Langmuir. vol. 21, No. 10, pp. 4705-4709.

Behanna, Heather A., Jack J. J. M. Donners, Alex C. Gordon, and Samuel I. Stupp. 2005. "Coassembly of Amphiphiles with Opposite Peptide Polarities into Nanofibers." Journal of the American Chemical Society. vol. 127, No. 4, pp. 1193-1200.

Bitton, Ronit, Judith Schmidt, Markus Biesalski, Raymond Tu, Matthew Tirrell, and Havazelet Bianco-Peled. 2005. "Self-Assembly of Model DNA-Binding Peptide Amphiphiles." Langmuir. vol. 21, No. 25, pp. 11888-11895.

Bull, Steve R., Mustafa O. Guler, Rafael E. Bras, Palamadai N. Venkatasubramanian, Samuel I. Stupp, and Thomas J. Meade. 2005. "Magnetic Resonance Imaging of Self-Assembled Biomaterial Scaffolds." Bioconjugate Chem. vol. 16, No. 6, pp. 1343-1348.

de Loos, Maaike, Ben L. Feringa, and Jan H. van Esch. 2005. "Design and Application of Self-Assembled Low Molecular Weight Hydrogels." Eur. J. Org. Chem. pp. 3615-3631.

Guler, Mustafa O., Randal C. Claussen, and Samuel I. Stupp. 2005. "Encapsulation of Pyrene Within Self-Assembled Peptide Amphiphile Nanofibers." Journal of Materials Chemistry. vol. 15, pp. 4507-4512.

Guler, Mustafa O., Jonathan K. Pokorski, Daniel H. Appella, and Samuel I. Supp. 2005. "Enhanced Oligonucleotide Binding to Self-Assembled Nanofibers." Bioconjugate Chem. vol. 16, No. 3, pp. 501-503.

Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." Adv. Mater. vol. 17, pp. 2612-2617.
Silva, Gabriel A. 2005. "Nanotechnology Approaches for the Regeneration and Neuroprotection of the Central Nervous System." Surgical Neurology. vol. 63, pp. 301-306.
Silva, Gabriel A. 2005. "Small Neuroscience: The Nanostructure of the Central Nervous System and Emerging Nanotechnology Applications." Current Nanoscience. vol. 1, No. 3, pp. 225-236.
Solis., F. J., S. I. Stupp, and M. Olvera de la Cruz. 2005. "Charge Induced Pattern Formation on Surfaces: Segregation in Cylindrical Micelles of Cationic-Anionic Peptide-Amphiphiles." The Journal of Chemical Physics. vol. 122, No. 5, 054905-1-054905-9.
Tovar, John D., Randal C. Claussen, and Samuel I. Stupp. 2005. "Probing the Interior of Peptide Amphiphile Supramolecular Aggregates." Journal of the American Chemical Society. vol. 127, No. 20, pp. 7337-7345.
Hosseinkhani, Hossein, Mohsen Hosseinkhani, and Hisatoshi Kobayashi. Jul. 2006. "Design of Tissue-Engineered Nanoscaffold Through Self-Assembly of Peptide Amphiphile." Journal of Bioactive and Compatible Polymers. vol. 21, No. 4, pp. 277-296.
Engler, Adam J., Shamik Sen, H. Lee Sweeney, and Dennis E. Discher. Aug. 25, 2006. "Matrix Elasticity Directs Stem Cell Lineage Specification." Cell. vol. 126, pp. 677-689.
Brunsveld, L., J. Kuhlmann, and H. Waldmann. 2006. "Synthesis of Palmitoylated Ras-Peptides and -Proteins." Methods. vol. 40, pp. 151-165.
Elgersma, Ronald C., Tania Meijneke, Remco de Jong, Arwin J. Brouwer, George Posthuma, Dirk T. S. Rijkers, and Rob M. J. Liskamp. 2006. "Synthesis and Structural Investigations of N-alkylated β-peptidosulfonamide-peptide Hybrids of the Amyloidogenic Amylin(20-29) Sequence: Implications of Supramolecular Folding for the Design of Peptide-Based Bionanomaterials." Organic & Biomolecular Chemistry. vol. 4, pp. 3587-3597.
Guler, Mustafa O., Lorraine Hsu, Stephen Soukasene, Daniel A. Harrington, James F. Hulvat, and Samuel I. Stupp. 2006. "Presentation of RGDS Epitopes on Self-Assembled Nanofibers of Branched Peptide Amphiphiles." Biomacromolecules. vol. 7, No. 6, pp. 1855-1863.
Harrington, Daniel A., Earl Y. Cheng, Mustafa O. Guler, Leslie K. Lee, Jena L. Donovan, Randal C. Claussen, and Samuel I. Stupp. 2006. "Branched Peptide-Amphiphiles as Self-Assembling Coatings for Tissue Engineering Scaffolds." Journal of Biomedical Materials Research Part A. pp. 157-167.
Hosseinkhani, Hossein, Mohsen Hosseinkhani, Ali Khademhosseini, Hisatoshi Kobayashi, and Yasuhiko Tabata. 2006. "Enhanced Angiogenesis Through Controlled Release of Basic Fibroblast Growth Factor from Peptide Amphiphile for Tissue Regeneration." Biomaterials. vol. 27, pp. 5836-5844.
Mardilovich, Anastasia, Jennifer A. Craig, Matthew Q. McCammon, Ashish Garg, and Efrosini Kokkoli. 2006. "Design of a Novel Fibronectin-Mimetic Peptide-Amphiphile for Functionalized Biomaterials." Langmuir. vol. 22, No. 7, pp. 3259-3264.
Paramonov, Sergey E., Ho-Wook Jun, and Jeffrey D. Hartgerink. 2006. "Self-Assembly of Peptide-Amphiphile Nanofibers: The Roles of Hydrogen Bonding and Amphiphilic Packing." Journal of the American Chemical Society. vol. 128, No. 22, pp. 7291-7298.
Rajangam, Kanya, Heather A. Behanna, Michael J. Hui, Xiaoqiang Han, James F. Hulvat, Jon W. Lomasney, and Samuel I. Stupp. 2006. "Heparin Binding Nanostructures to Promote Growth of Blood Vessels." Nano Letters. vol. 6, No. 9, pp. 2086-2090.
Reches, Meital and Ehud Gazit. 2006. "Molecular Self-Assembly of Peptide Nanostructures: Mechanism of Association and Potential Uses." Current Nanoscience. vol. 2, No. 2, pp. 105-111.
Stendahl, John C., Mukti S. Rao, Mustafa O. Guler, and Samuel I. Stupp. 2006. "Intermolecular Forces in the Self-Assembly of Peptide Amphiphile Nanofibers." Advanced Functional Materials. vol. 16, pp. 499-508.
Behanna, Heather A., Kanya Rajangam, and Samuel I. Stupp. 2007. "Modulation of Fluorescence Through Coassembly of Molecules in Organic Nanostructures." Journal of the American Chemical Society. vol. 129, No. 2, pp. 321-327.
Meijer, Joris T., Marjolijn Roeters, Valentina Viola, Dennis W. P. M. Löwik, Gert Vriend, and Jan C. M. van Hest. 2007. "Stabilization of Peptide Fibrils by Hydrophobic Interaction." Langmuir. vol. 23, No. 4, pp. 2058-2063.
Niece, Krista L., Catherine Czeisler, Vibhu Sahni, Vicki Tysseling-Mattiace, Eugene T. Pashuck, John A. Kessler, and Samuel I. Stupp. 2008. "Modification of Gelation Kinetics in Bioactive Peptide Amphiphiles." Biomaterials. vol. 29, pp. 4501-4509.
Löwik, Dennis W. P. M., Jeffrey G. Linhardt, P. J. Hans M. Adams, and Jan C. M. van Hest. 2003. "Non-Covalent Stabilization of a β-Hairpin Peptide into Liposomes." Org. Biomol. Chem. vol. 1, pp. 1827-1829.
Extended European Search Report mailed Nov. 17, 2010 for corresponding European Patent Application No. 08746046.5.
Jun, Ho-Wook, Virany Yuwono, Sergey E. Paramonov, and Jeffrey D. Hartgerink. 2005. "Enzyme-Mediated Degradation of Peptide-Amphiphile Nanofiber Networks." Advanced Materials. vol. 17, pp. 2612-2617.
Kirkham, J., A. Firth, D. Vernals, N. Boden, C. Robinson, R. C. Shore, S. J. Brookes, and A. Aggeli. 2007. "Self-Assembling Peptide Scaffolds Promote Enamel Remineralization." J. Dent. Res. vol. 86, No. 5, pp. 426-430.
Stryker, Lori. 2008. "Titanium Dioxide: Toxic or Safe?" The Organic Make-up Company Inc. www.organicmakeup.ca/ca/titaniumdioxide.asp. 4 pages. Printed Aug. 25, 2010.
Martin, Ivan, R. Suetterlin, W. Baschong, M. Heberer, G. Vunjak-Novakovic, and L. E. Freed. 2001. "Enhanced Cartilage Tissue Engineering by Sequential Exposure of Chondrocytes to FGF-2 During 2D Expansion and BMP-2 During 3D Cultivation." Journal of Cellular Biochemistry. vol. 83, pp. 121-128.
Oteiza, Patricia I., Gerardo G. Mackenzie, and Sandra V. Verstraeten. 2004. "Metals in Neurodegeneration: Involvement of Oxidants and Oxidant-Sensitive Transcription Factors." Molecular Aspects of Medicine. vol. 25, pp. 103-115.
Shen, Qin, Susan K. Goderie, Li Jin, Nithin Karanth, Yu Sun, Natalia Abramova, Peter Vincent, Kevin Pumiglia, and Sally Temple. May 28, 2004. Science. vol. 304, pp. 1338-1340.
Yang, Zhengqin, Sufen Yang, Steven Y. Qian, Jau-Shyong Hong, Maria B. Kadiiska, Raymond W. Tennant, Michael P. Waalkes, and Jie Liu. 2007. "Cadmium-Induced Toxicity in Rat Primary Mid-brain Neuroglia Cultures: Role of Oxidative Stress from Microglia." Toxicological Sciences. vol. 98, No. 2, pp. 488-494J.
Xia, Qing, Xudong Feng, Haifeng Huang, Lingyan Du, Xiaoda Yang, and Kui Wang. Dec. 20, 2010 (Accepted date). "Gadolinium-Induced Oxidative Stress Triggers Endoplasmic Reticulum Stress in Rat Cortical Neurons." Accepted Article for Journal of Neurochemistry. 23 pages.

* cited by examiner

SEQ ID NO:2

(palmitoyl-Ser-Leu-Ser-Leu-Ala-Ala-Ala-Glu-Glu-Ile-Lys-Val-Ala-Val-OH)

Expected mass = 1638.02 amu

SEQ ID NO:4

(palmitoyl-Ser-Leu-Ser-Leu-Ala-Ala-Ala-Asp-Ile-Lys-Val-Ala-Val-OH)

Expected mass = 1495.89 amu

SEQ ID NO:6

(palmitoyl-Ser-Leu-Ser-Leu-Ala-Ala-Ala-Glu-Ile-Lys-Val-Ala-Val-OH)

Expected mass = 1508.98 amu

SEQ ID NO:7

(palmitoyl-Ala-Ala-Ala-Leu-Leu-Leu-Glu-Glu-Ile-Lys-Val-Ala-Val-OH)

Expected mass = 1577.04 amu

Electrospray Ionization Mass Spectroscopy, negative ion mode (ESA-MS) for SEQ ID NO: 2
[M-2H]/2: expected = 818.0; found = 818.5
[M-3H]/3: expected = 545.0; found = 545.4

Analytical high pressure liquid chromatography (HPLC) for SEQ ID NO:2

Analytical high pressure liquid chromatography for SEQ ID NO:4

Comparison of Rheological Properties of SEQ ID NO:2 and SEQ ID NO:6
Solid line: SEQ ID NO:2, Dashed line: SEQ ID NO:6

Circles: SEQ ID NO:2, Triangles: SEQ ID NO:6

```
                       SEQUENCE LISTING

<160> NUMBER OF SEQ ID NOS: 32

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<223> OTHER INFORMATION: see specification as filed for detailed
      description of substitutions and preferred embodiments
<220> FEATURE:
<221> NAME/KEY: MOD_RES
<222> LOCATION: (8)..(12)
<223> OTHER INFORMATION: Any amino acid with an acidic side chain and
      this region may encompass 0 to 5 residues

<400> SEQUENCE: 1

Ser Leu Ser Leu Ala Ala Ala Xaa Xaa Xaa Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Acylated-Ser

<400> SEQUENCE: 2

Ser Leu Ser Leu Ala Ala Ala Glu Glu Ile Lys Val Ala Val
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any alpha substitued amino acid residue with 0
      to 5 carbon atoms

<400> SEQUENCE: 3

Ser Leu Ser Leu Ala Ala Ala Xaa
1               5

<210> SEQ ID NO 4
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: Mod_res
<222> LOCATION: (1)..(1)
<223> OTHER INFORMATION: Acylated-Ser

<400> SEQUENCE: 4

Ser Leu Ser Leu Ala Ala Ala Asp Ile Lys Val Ala Val
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Lys Val Ala Val
1               5

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: Mod_Res
<222> LOCATION: (1)..(1)
<223> OTHER INFORMATION: Acylated-Ser

<400> SEQUENCE: 6

Ser Leu Ser Leu Ala Ala Ala Glu Ile Lys Val Ala Val
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: Mod_Res
<222> LOCATION: (1)..(1)
<223> OTHER INFORMATION: Acylated-Ala

<400> SEQUENCE: 7

Ala Ala Ala Leu Leu Leu Glu Glu Ile Lys Val Ala Val
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Val Val Val Ala Ala Ala
1               5

<210> SEQ ID NO 9
<211> LENGTH: 6
<212> TYPE: PRT
```

```
<213> ORGANISM: Artificial Sequence
<220> FEATURE:
<223> OTHER INFORMATION: Synthetic peptide

<400> SEQUENCE: 9

Ala Ala Ala Val Val Val
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Leu Leu Leu Ala Ala Ala
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Val Val Val Val Val Val
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Val Val Val Leu Leu Leu
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Leu Leu Leu Val Val Val
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Ala Ala Ala Ala Ala Ala
1               5

<210> SEQ ID NO 15
<211> LENGTH: 7
<212> TYPE: PRT
<213> ORGANISM: Artificial Sequence
<220> FEATURE:
```

```
<223> OTHER INFORMATION: Synthetic peptide

<400> SEQUENCE: 15

Ala Ala Ala Ala Gly Gly Gly
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Leu Leu Leu Leu Leu Leu
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

Ala Ala Ala Gly Gly Gly
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Leu Leu Leu Gly Gly Gly
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Ala Ala Ala Leu Leu Leu
1               5

<210> SEQ ID NO 20
<211> LENGTH: 4
<212> TYPE: PRT
<213> ORGANISM: Artificial Sequence
<220> FEATURE:
<223> OTHER INFORMATION: Synthetic peptide

<400> SEQUENCE: 20

Ser Leu Ser Leu
1

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 21

Ser Leu Ser Leu Ala Ala Ala
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: Mod_Res
<222> LOCATION: (1)..(5)
<223> OTHER INFORMATION: This region may encompass 0 to 5 residues,
      preferably 2-5 residues or 1-3 residues.

<400> SEQUENCE: 22

Glu Glu Glu Glu Glu Ile Lys Val Ala Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: see specification as filed for detailed
      description of substitutions and preferred embodiments
<220> FEATURE:
<221> NAME/KEY: Mod_Res
<222> LOCATION: (1)..(5)
<223> OTHER INFORMATION: Xaa is any amino acid with an acidic side
      chain, preferably Ama, Asp, Aib, Apm or Gla.  This region may
      encompass 0 to 5 residues, preferably 1-5, and more preferably
      1-3.

<400> SEQUENCE: 23

Xaa Xaa Xaa Xaa Xaa Ile Lys Val Ala Val
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<223> OTHER INFORMATION: see specification as filed for detailed
      description of substitutions and preferred embodiments
<220> FEATURE:
<221> NAME/KEY: Mod_RES
<222> LOCATION: (1)..(5)
<223> OTHER INFORMATION: Xaa is any amino acid with an acidic side
      chain, preferably Ama, Asp, Aib, Apm or Gla. This region may
      encompass 0 to 5 residues, preferably 1-5, or more preferably 1-3.

<400> SEQUENCE: 24

Xaa Xaa Xaa Xaa Xaa Val Ala Val Lys Ile
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide

<400> SEQUENCE: 25
```

```
Val Val Ile Ala Lys
1               5

<210> SEQ ID NO 26
<211> LENGTH: 16
<212> TYPE: PRT
<213> ORGANISM: Artificial Sequence
<220> FEATURE:
<223> OTHER INFORMATION: Synthetic peptide

<400> SEQUENCE: 26

Cys Arg Lys Gln Ala Ala Ser Ile Lys Val Ala Val Ser Ala Asp Arg
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(5)
<223> OTHER INFORMATION: Xaa is any amino acid with an acidic side
      chain, preferably Ama, Asp, Aib, Apm, or Gla.  This region may
      encompass 0 to 5 residues, preferably 1-5 residues.
<220> FEATURE:
<221> NAME/KEY: Mod-Res
<222> LOCATION: (11)..(13)
<223> OTHER INFORMATION: Xaa may be any amino acid.  This region may
      encompass 0 to 3 residues.

<400> SEQUENCE: 27

Xaa Xaa Xaa Xaa Xaa Ile Lys Val Ala Val Xaa Xaa Xaa
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(5)
<223> OTHER INFORMATION: Xaa may be any amino acid with an acidic side
      chain, preferably Ama, Asp, Aib, Apm or Gla.  This region may
      encompass 0 to 5 residues, or preferably 1 to 5 residues.
<220> FEATURE:
<221> NAME/KEY: MOD-RES
<222> LOCATION: (11)..(13)
<223> OTHER INFORMATION: Xaa may be any amino acid and this region may
      encompass 0 to 3 residues.

<400> SEQUENCE: 28

Xaa Xaa Xaa Xaa Xaa Val Ala Val Lys Ile Xaa Xaa Xaa
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29

Glu Glu Ile Lys Val Ala Val
1               5

<210> SEQ ID NO 30
```

```
<211> LENGTH: 6
<212> TYPE: PRT
<213> ORGANISM: Artificial Sequence
<220> FEATURE:
<223> OTHER INFORMATION: Synthetic peptide

<400> SEQUENCE: 30

Asp Ile Lys Val Ala Val
1               5

<210> SEQ ID NO 31
<211> LENGTH: 3
<212> TYPE: PRT
<213> ORGANISM: Artificial Sequence
<220> FEATURE:
<223> OTHER INFORMATION: Synthetic peptide

<400> SEQUENCE: 31

Arg Gly Asp
1

<210> SEQ ID NO 32
<211> LENGTH: 5
<212> TYPE: PRT
<213> ORGANISM: Artificial Sequence
<220> FEATURE:
<223> OTHER INFORMATION: Synthetic peptide

<400> SEQUENCE: 32

Tyr Ile Gly Ser Arg
1               5
```

PEPTIDE AMPHIPHILES HAVING IMPROVED SOLUBILITY AND METHODS OF USING SAME

PRIORITY

This application claims the benefit of U.S. Provisional Application No. 60/912,289 filed Apr. 17, 2007, the entire contents of which are incorporated by reference herein.

FIELD OF THE INVENTION

The present invention relates generally to new and improved peptide amphiphiles (PAs) having superior gelation kinetics and rheological properties, novel peptide-amphiphile nanofibers self-assembled therefrom and methods of making and using same. More particularly, the present invention relates to amphiphilic molecules composed of at least three distinct segments—namely, a non-peptide, lipophilic segment disposed at or near the N-terminus, an intermediate structural peptide segment, and a functional peptide segment disposed at or near the C-terminus—wherein the particular amino acid sequence of the peptide segments confer the peptide amphiphile with unexpectedly superior properties, for example an increased solubility, that, in turn, enables purification to a level necessary for in vivo applications, such as administration to human subjects (e.g., at least 95% purity).

BACKGROUND OF THE INVENTION

Techniques of tissue engineering employing biocompatible scaffolds provide viable alternatives to materials currently used in prosthetic and reconstructive surgery. These materials also hold promise in the formation of tissue or organ equivalents to replace diseased, defective, or injured tissues. In addition, biocompatible scaffolds can be used to form biodegradable materials which may be used for controlled release of therapeutic materials (e.g. genetic material, cells, hormones, drugs, or pro-drugs) into a predetermined area. However, most polymers used today to create these scaffolds, such as polylactic acid, polyorthoesters, and polyanhydrides, are difficult to control and result in, among other things, poor cell attachment and poor integration into the site where the tissue engineered material is utilized. Accordingly, focus has shifted to scaffolds formed from synthetic biomolecules, more particularly biomimetic scaffolds capable of in situ self-assembly.

The preparation of any synthetic material with structure on the nanoscale that mimics natural tissue is a challenging problem. One approach has been to prepare molecules that spontaneously assemble into fibrils similar in morphology to the proteins and proteoglycans that compose the natural extracellular matrix. In contrast to most synthetic biopolymers, the use of small, self-assembling molecules facilitates control of chemical and structural properties of these macromolecular assemblies.[1-12] To that end, peptide amphiphiles have recently been shown to self-assemble under suitable conditions to form fibril-like micelles (referred to in the art as "nanofibers"), such nanofibers having particular utility as biocompatible scaffolds, more particularly in the area of tissue engineering.[13-26] However, many such molecules have proven difficult to synthesize and/or purify on a large scale. This is due in part to the molecules' zwitterionic nature (i.e., carrying both positive and negative charges), and their propensity to aggregate in solution due to the relative large proportion of non-polar amino acid residues.[1, 27, 28] The present invention addresses this need by providing novel peptide amphiphile molecules and compositions having improved physical and chemical properties that enable automated synthesis and purification to the level required for in vivo applications. In addition, gels of the improved peptide amphiphile compositions of the present invention formed in artificial cerebrospinal fluid (CSF)[29-31] are demonstrated herein to possess an increased mechanical stiffness which better mimics the mechanical properties of natural central nervous system tissues, which, in turn, should correlate to improved neurogenic differentiation of mesenchymal stem cells.[32]

SUMMARY OF THE INVENTION

Accordingly, it is an objective of the present invention to provide improved peptide amphiphile (PA) molecules having superior gelation kinetics and rheological properties, such PA molecules including, at a minimum, the following three segments: (1) a non-peptide, lipophilic segment, composed generally of a single alkyl chain; (2) a structural peptide segment which confers the molecule with both the ability to form a beta-sheet secondary structure and an unexpected increase in solubility, that, in turn, enables purification by liquid chromatography (LC); and (3) a functional peptide segment that includes charged amino acids that, by virtue of the choice of the amino acids and their arrangement in the segment, mimic the binding domains of proteins present in the natural extracellular matrix of the central nervous system during development.

It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

Accordingly, it is an object of the present invention to provide a peptide-amphiphile (PA) molecule as described above, wherein the peptide portion of the molecule includes the amino acid sequence "SLSLAAA(X)$_n$," (e.g., SEQ ID NO:1), wherein n is an integer that ranges between 0 and 5, more preferably between 1 and 3, and wherein X is an amino acid residue selected from those with acidic side-chains, including, for example, glutamic acid (E) and aspartic acid (D). One particularly preferred peptide amphiphile that is uniquely suited for use as a scaffold for spinal cord regeneration has the following structure and is referred to herein as SEQ ID NO:2 ($C_{16}H_{31}$O-Ser-Leu-Ser-Leu-Ala-Ala-Ala-Glu-Glu-Ile-Lys-Val-Ala-Val-OH). In these preferred embodiments, the lipophilic alkyl segment is attached to the N-terminus of the peptide components through a peptide bond, the "structural" and "functional" peptide segments together form a single, linear peptide chain, and the C-terminus of the peptide is a free acid. As discussed in detail below, SEQ ID NO:2 possesses superior gelation kinetics and rheological properties that facilitate automated synthesis and purification using high pressure liquid chromatography (HPLC).

Increasing or decreasing the length of the acidic amino acid residue's side-chain can also modify the solubility of peptide amphiphiles containing that residue, as can changing the number of carboxylic acid groups on the side-chain. Accordingly, it is an object of the present invention to provide a peptide-amphiphile molecule wherein the peptide portion of the molecule includes the amino acid sequence "SLS-LAAAX" (SEQ ID NO:3), where X is an alpha-substituted amino acid with 0 to 5, more preferably 1 to 3 carbon atoms between the alpha carbon and one or more carboxylic acid residues. In a preferred embodiment, X is selected from aminomalonic acid (Ama), aspartic acid (Asp), glutamic acid (Glu), aminoadipic acid (Aib), aminoheptanedioic acid (Apm) or gammacarboxyglutamic acid (Gla). Accordingly, another particularly preferred peptide amphiphile for use as a scaffold for spinal cord regeneration has the following structure and is referred to herein as SEQ ID NO:4 ($C_{16}H_{31}O$-Ser-Leu-Ser-Leu-Ala-Ala-Ala-Asp-Ile-Lys-Val-Ala-Val-OH).

It is a further object of the present invention to provide new and improved PA molecules that have the ability to self-assemble under suitable conditions into cylindrical micelles, also called nanofibers, in which the lipophilic segments are packed into the center and the hydrophilic functional peptide segments are exposed along the surface of the nanofiber. In such embodiments, the functional peptide segment is preferably multiply-charged at physiological pH. While not wishing to be bound by theory, it appears that the specific number of charged amino acids as well as the alpha-amino acid side-chain length and overall hydrophobic and hydrophilic arrangement of the amino acid sequence plays an important role in PA self-assembly. While a large number of specific PA sequences have been disclosed previously in the literature,[1, 2, 7, 14-24, 27, 33-45] despite several attempts,[46-49] no general theory or model has been described that would allow one of ordinary skill in the art to predict the self-assembly, gelation kinetics or rheological properties a particular peptide sequence a priori.

It is a further object of the present invention to provide a composition composed of one or more peptide amphiphiles self-assembled to form one or more non-spherical micelles, for example conical micelles, examples of which include, but are not limited to, nanofibers.

The composition may also take the form of a substrate provided with self-assembled non-spherical micelles over at least a portion of the substrate, for example as a coating of nanofibers disposed thereon.

It is a further object of the present invention to provide biocompatible, biodegradable gels composed of peptide amphiphiles and/or peptide-amphiphile compositions, such gels being useful in the creation of scaffolds or templates, which may or may not include isolated cells, into a human patient to create or induce the body to create an organ or tissue equivalent. Such gels could promote cell engraftment and provide three-dimensional templates for new tissue growth. The resulting tissue is expected to be generally similar in composition and histology to naturally occurring tissue, in contrast to scar tissue that would generally result absent intervention during the body's natural healing process.

To that end, the present invention provides in one embodiment a self-assembling peptide-amphiphile solution than can be directly injected into a target site within a human patient, wherein the self-assembled peptide-amphiphile gel organizes into a fibrillar scaffold or matrix. In another embodiment, cells may be suspended in a self-assembled peptide-amphiphile gel that is pre-formed into a matrix outside the body, which then can be implanted into a human patient. Ultimately, the self-assembled peptide-amphiphile gel degrades, leaving only the resulting tissue. In yet another embodiment of the present invention, the peptide-amphiphiles of the present invention are used in conjunction with other tissue engineering materials, either as a gel, solid, or liquid and are used to template tissue growth in a pre-determined area on a patient.

It is a further object of the present invention to provide a fibrillar (or nanofibrous) scaffold of self-assembling peptide amphiphiles whose design and function is patterned after naturally occurring materials and tissues. For example, in one embodiment, the present invention provides for self-assembling peptide amphiphiles whose design and function is patterned after proteins involved in central nervous system development.[37, 50, 51]

One of skill in the art will readily recognize that a gel or solid comprised of these nanofibers under physiological conditions of pH, temperature and tonicity affords the opportunity to utilize this material for a wide range of purposes and in a number of different potential biomedical and tissue engineering applications.

Accordingly, in one embodiment, the present invention provides a method of treating a patient with tissue engineered material that includes the step of administering a peptide amphiphile composition to a target site on the patient in need of a tissue engineered material.

One particularly preferred utility for the peptide amphiphile molecules and the gels formed therefrom is in the field of nerve regeneration and spinal cord injury treatment. PA compositions are capable of stimulating neural progenitor cell differentiation and of inhibiting scar tissue formation by CNS cells.[37, 50, 51] PAs of the present invention may also find application in regulation, inhibition or promotion of axon outgrowth in neurons as well as the regulation, inhibition or promotion of cell-substrate adhesion among nerve cells.

It is a further object of the present invention to provide methods and compositions for altering (e.g., augmenting or stimulating) differentiation and growth of cells (e.g., neural progenitor cells and neurons). In particular, the present invention relates to compositions comprising one or more self-assembling peptide amphiphiles (e.g., in solution) that generate (e.g., self-assemble into) nanofibers that are able to encapsulate cells and promote cellular differentiation (e.g., neurite development) and methods of using the same. Compositions and methods of the present invention find use in research, clinical (e.g., therapeutic) and diagnostic settings.

In some embodiments, the present invention provides a method of altering development of a neuron comprising contacting the neuron with a composition comprising a peptide amphiphile. In some embodiments, altering development of a neuron comprises axonal growth. In some embodiments, the axonal growth comprises descending motor fiber growth. In some embodiments, the axonal growth comprises ascending sensory fiber growth. In some embodiments, altering development occurs through a lesion site. In some embodiments, altering development of a neuron is accompanied by reduced astrogliosis. In some embodiments, the peptide amphiphile comprises an IKVAV sequence (SEQ ID NO:5) and/or other amino acid sequence selected from the amino acid sequence of laminin, a family of proteins present in the extracellular matrix of the developing mammalian central nervous system.[37] In some embodiments, the neuron is a neuron in a spinal cord that has been damaged. In some embodiments, the spinal cord has been damaged by traumatic spinal cord injury. In some embodiments, the neuron is a sensory neuron. In some embodiments, the neuron is a motor neuron. In some embodiments, altering development of a neuron comprises promoting development of the neuron. In some embodiments, altering development of a neuron comprises regenerating development of a damaged neuron, for example a neurite.

It is a further object of the present invention to provide a method for treating a subject comprising the steps of: administering a composition comprising a peptide amphiphile to a subject with a damaged nerve or nerves, under conditions such that neuron growth occurs in the subject. In some embodiments, the neuron growth comprises axonal growth. In some embodiments, the axonal growth comprises descending motor fiber growth. In some embodiments, the axonal growth comprises ascending sensory fiber growth. In some embodiments, the neuron growth comprises axonal growth at the site of the damaged nerve. In some embodiments, the neuron growth is accompanied by reduced astrogliosis and associated scar tissue formation in the subject. In preferred embodiments, the reduced astrogliosis and the reduced scar formation occur at the site of nerve damage. In some embodiments, the damaged nerve is a nerve in a spinal cord that has been damaged. In some embodiments, the damaged nerve has been damaged by traumatic spinal cord injury. In some embodiments, the damaged nerve comprises a damaged sensory neuron. In some embodiments, the damaged nerve comprises a damaged motor neuron. In some embodiments, neuron growth comprises regenerating development of a damaged neuron. In some embodiments, administering comprises intrathecal injection of an aqueous solution of the peptide amphiphile. In some embodiments, the peptide amphiphile forms a nanofiber gel upon contact with the damaged tissue. In some embodiments, the composition comprising a peptide amphiphile is co-administered with one or more other agents.

It is a further object of the present invention to provide pharmaceutical compositions comprising one or more peptide amphiphiles, for example those comprising an IKVAV sequence (SEQ ID NO:5). See U.S. Patent Publication No. 2006-0247165 (Stupp et al.), the contents of which are incorporated by reference herein.

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art having knowledge of various amphiphilic compounds, self-assembly techniques and peptide synthesis. Such objects, features, benefits and advantages will be apparent from the above as taken into conjunction with the accompanying examples, data, figures and all reasonable inferences to be drawn therefrom, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments which follows:

As shown in FIG. 3A, the complex shear modulus (G*) (defined as the shear stress divided by the shear strain) of SEQ ID NO:2 was found to be an order of magnitude greater that that for SEQ ID NO:6 at one hour post-gelation. In the figure, the solid line is SEQ ID NO:2 and the dashed line is SEQ ID NO:6. As shown in FIG. 3B, SEQ ID NO:2 presented a significantly lower value of tan($\delta$), indicating more "gel-like" properties, as compared to more "liquid-like" behavior for SEQ ID NO:6. In the figure, the circles represent SEQ ID NO:2 and the triangles represent SEQ ID NO:6.

Figure 1:
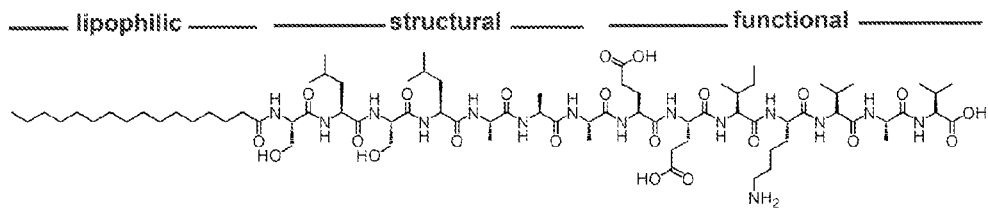
FIG. 1 depicts the chemical structures of peptide amphiphiles referred to herein as SEQ ID NO:2, SEQ ID NO:4, SEQ ID NO:6 and SEQ ID NO:7, with the "lipophilic", "structural" and "functional" peptide segments indicated.
Figure 1:
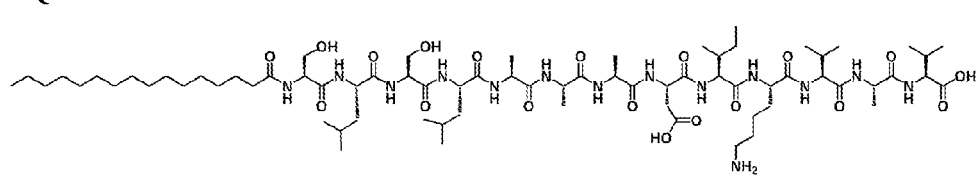
Figure 1:
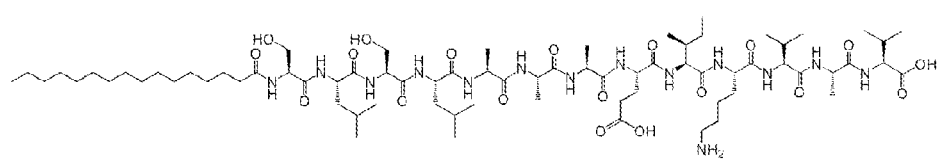
Figure 1:
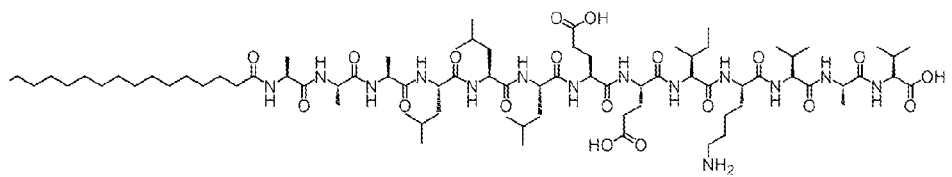

These unexpectedly different gelation kinetics and rheological properties are expected to be superior for tissue engineering application in the spinal cord, given that gels of SEQ ID NO:2 better mimic the mechanical properties of natural central nervous system tissues.[32] In addition, the solubility of this molecule and SEQ ID NO:4 was significantly higher in a broad range of aqueous buffer solutions. For example, the solubility of SEQ ID NO:2 and SEQ ID NO:4 in water containing 0.1% by volume ammonium hydroxide was in excess of 20 mg/mL, whereas the solubility of SEQ ID NO:6 in the same buffer was less than 1 mg/mL. These unexpectedly superior solubility properties enable markedly improved HPLC purification, more particularly the degree of purification required for in vivo applications and for pharmaceutical use.

DETAILED DESCRIPTION OF THE PREFERRED EMBODIMENTS

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

As used herein and in the appended claims, the singular forms a an and "the" include plural reference unless the context clearly dictates otherwise. Thus, for example, reference to a "cell" is a reference to one or more cells and equivalents thereof known to those skilled in the art, and so forth.

As used herein, the term "nanofiber" refers to an elongated or threadlike filament having a diameter of less than 100 nanometers.

As used herein, the term "cylindrical micelle" refers to a colloidal aggregate with a non-spherical, high-aspect-ratio shape (length/diameter >10), composed of amphiphilic molecules in which the hydrophobic (or lipophilic) part of the amphiphiles forming the micelle tends to locate away from the polar phase (e.g. water) while the polar parts of the molecule (head groups) tend to locate at the micelle-solvent interface.

As used herein, the term "physiological conditions" refers to the range of conditions of temperature, pH and tonicity (or osmolality) normally encountered within tissues in the body of a living human.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties of those components.

As used herein, the terms "scaffold" and "matrix" refer interchangeably to a natural or synthetic structure or meshwork of structures with open porosity that is extended in space and provides mechanical or other support for the growth of living tissue, either in the body or in vitro.

As used herein, the term "gel" refers to a semi-solid, viscoelastic material (capable of resisting some mechanical stress without deformation), which is formed by the coagulation of a colloidal liquid, consisting of a fibrous matrix and fluid-filled interstices.

As used herein, the term "peptide amphiphile" refers to a molecule that, at a minimum, includes a non-peptide lipophilic segment, a structural peptide segment and a functional peptide segment. The peptide amphiphile may express a net charge at physiological pH, either a net positive or negative net charge, or may be zwitterionic (i.e., carrying both positive and negative charges).

As used herein and in the appended claims, the term "lipophilic segment" refers to the hydrocarbon moiety disposed on the N-terminus of the peptide amphiphile. This lipophilic segment may be herein and elsewhere referred to as the hydrophobic component or hydrophobic segment. The lipophilic segment should be of a sufficient length to provide amphiphilic behavior and micelle formation in water or another polar solvent system.

Accordingly, in the context of the present invention, the lipophilic segment preferably comprises a single, linear alkyl chain of the formula: $C_{n-1}H_{2n-1}O$—, where n=6-22. A particularly preferred lipophilic molecule is palmitic acid ($C_{15}H_{31}(O)$—). However, other small lipophilic molecules may be used in place of the alkyl chain.

As used herein and in the appended claims, the term "structural peptide segment" refers to the intermediate amino acid sequence of the peptide amphiphile molecule generally composed of three to ten amino acid residues with non-polar, uncharged side chains, selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (O), Leu (L), Thr (T), Ala (A), Gly (G), (listed in order of their propensity to form beta sheets). However, non-naturally occurring amino acids of similar beta-sheet forming propensity may also be used. In a preferred embodiment, the N-terminus of the structural peptide segment is covalently attached to the oxygen of the lipophilic segment and the C-terminus of the structural peptide segment is covalently attached to the N-terminus of the functional peptide segment. In a more preferred embodiment, a strong and a weak beta sheet former are used in combination, for example taking the form $(X_A)_{Na}(X_B)_{Nb}$, where $X_A$ and $X_B$ are selected from A, L, V and G and Na and Nb are 2, 3 or 4. Illustrative examples include (SEQ ID NOs: 8-19)

```
VVVAAA  AAAVVV  LLLAAA  VVVVVV

VVVLLL  LLLVVV  AAAAAA  AAAAGGG

LLLLLL  AAAGGG  LLLGGG  AAALLL
```

In the context of the present invention, one particularly preferred structural peptide segment has the amino acid sequence AAALLL (SEQ ID NO:19). This structural segment is utilized in the exemplary peptide amphiphile SEQ ID NO:7 which has the following structure: $C_{16}H_{32}O$-Ala-Ala-Ala-Leu-Leu-Leu-Glu-Glu-Ile-Lys-Val-Ala-Val-OH In an alternative, more preferred embodiment, the structural peptide segment may take the form $(X_C)(X_A)_{Na}(X_B)_{Nb}$, wherein $X_A$ and $X_B$ are as described above and $X_C$ is "SLSL" (SEQ ID NO:20). The SLSL (SEQ ID NO: 20) modification to the system is expected to lead to slower gelation kinetics. While not wishing to be bound by theory, it is believed that the polar serine hydroxyl interspersed with the bulky leucine side chains may partially inhibit packing of the molecules into the nanofiber. Slower gelation is expected to be particularly applicable to a functional, in situ environment, such as an operating room, where it may be advantageous to have delayed gel formation during deliver of peptide amphiphile nanofibers to various tissue sites in the body. As discussed in further detail below, one particularly preferred structural peptide segment has the amino acid sequence "SLSLAAA" (SEQ ID NO:21).

As used herein and in the appended claims, the term "functional peptide segment" refers to the C-terminally disposed peptide sequence containing anywhere from 3 to 15 amino acid residues, with at least one (and generally 2-7) amino acid residues that have side chains that are ionized under physiological conditions, examples of which selected from the 20 naturally occurring amino acids include Lys (K), Arg (R), Glu (E) and/or Asp (D), however other non-natural amino acid residues with ionizable side chains could be used, as will be evident to one ordinarily skilled in the art. The amino acid sequence of this segment is typically selected based on known binding domains for integrins, proteins, growth factors or other biological molecules. Upon self-assembly, the functional peptide group is exposed at the surface of the nanofiber, thereby serving as a bioactive signal presented to the environment.

Examples of functional peptide sequences suitable for use in the context of the peptide amphiphile of present invention include, but are not limited to, "$E_n$IKVAV" (SEQ ID NO:22, where E represents glutamic acid (Glu) and n is an integer between 0 and 5, preferably between 2 and 5 or 1 and 3. Alternatively, the functional peptide segment may comprise a sequence including $X_n$IKVAV (SEQ ID NO:23), where X is an amino acid residue with acidic side chains, more preferably an amino acid residue selected from aminomalonic acid (Ama), aspartic acid (Asp), aminoadipic acid (Aib), aminoheptanedioic acid (Apm) or gammacarboxyglutamic acid (Gla) and n again is an integer between 0 and 5, preferably between 1 and 5, more preferably between 1 and 3.

Alternately, the sequence of the amino acids may be reversed, such that the functional peptide sequence comprises $X_n$VAVKI (SEQ ID NO:24), where n is an integer between 0 and 5, preferably between 1 and 5, and X is as defined above. Other variations on the functional sequence are possible by substituting one or more of the non-polar amino acid residues (V, A, or I), with another, similarly non-polar residue, including but not limited to I, A, G, V, or L. As will be understood by one skilled in the art, these and similar modifications may potentially retain the biological function of the original IKVAV (SEQ ID NO:5) peptide sequence. Furthermore, some aspects of the present invention may utilize "scrambled" a peptide sequence, such as VVIAK (SEQ ID NO:25), [52] which changes its ability to specifically bind its corresponding receptor, growth factor, etc. and thus may alter (i.e., increase or decrease) the original biological function of the peptide, depending on the particular arrangement employed. In some instances of the present invention, it may be advantageous to use a longer portion of the peptide sequence from the laminin 1α chain, such as CRKQAASIKVAVSADR[53] (SEQ ID NO:26) or a portion thereof [54]. These functional peptide segments may further include other known segments, in their original, reversed or scrambled form, provided that it retains the amphiphilic peptide molecules' ability to bind the functional peptide segments' corresponding receptor, growth factor, or the like.

See WO 2004/018628, the contents of which are incorporated by reference herein. In addition, the amphiphilic peptide molecules of the present invention may include more than one functional peptide sequences, for binding interaction with one or more corresponding receptors, growth factors, or the like. For example, U.S. Patent Publication No. 2005-0208589 (Stupp et al.), the contents of which are incorporated by reference herein, describes a functional segment having a branched structure for enhanced epitope presentation. Multiple epitope peptide amphiphiles are further described in U.S. Patent Publication No. 2005-0209145 (Stupp et al.) and 2005-0208589 (Stupp et al.), the contents of which are incorporated by reference herein.

Amino acids useful in the peptide amphiphiles of the present invention include but are not limited to naturally occurring amino acids and artificial amino acids. Incorporation of artificial amino acids such as beta or gamma amino acids and those containing non-natural side chains, and/or other similar monomers such as hydroxyacids are also contemplated, with the effect that the corresponding component is peptide-like in this respect.

The peptide amphiphile molecules and compositions of the present invention can be synthesized using preparatory techniques well-known to those skilled in the art, preferably, by standard solid-phase peptide synthesis, with the addition of a fatty acid in place of a standard amino acid at the N-terminus of the peptide, in order to create the lipophilic segment. Synthesis typically starts from the C-terminus, to which amino acids are sequentially added using either a Rink amide resin (resulting in an —NH$_2$ group at the C-terminus of the peptide after cleavage from the resin), or a Wang resin (resulting in an —OH group at the C-terminus). Accordingly, the present invention encompasses peptide amphiphiles having a C-terminal moiety that may be selected from the group consisting of —H, —OH, —COOH, —CONH$_2$, and —NH$_2$. In some embodiments, solid phase synthesis can be performed using a polymeric resin support that is pre-loaded with a protected amino acid at a loading fraction of 0.1-0.4 mmole/g, said loading fraction selected to improve synthetic yield of the peptide.

The lipophilic segment is typically incorporated at the N-terminus of the peptide after the last amino acid coupling, and is composed of a fatty acid or other acid that is linked to the N-terminal amino acid through a peptidyl bond. In aqueous solutions, PA molecules self-assemble into cylindrical micelles that bury the lipophilic segment in their core and display the functional peptide on the surface. The structural peptide undergoes intermolecular hydrogen bonding to form beta sheets that orient parallel to the long axis of the micelle. The cylindrical micelles (also referred to as nanofibers) can form gels in water or various aqueous media at concentrations ranging typically from 0.5 to 4 wt %.

To induce self-assembly of an aqueous solution of peptide amphiphiles, the pH of the solution may be changed (raised or lowered) or multivalent ions or charged polymers or other macromolecules may be added to the solution. Though not intending to be bound by theory, self-assembly is facilitated in the instant case by the neutralization or screening (reduction) of electrostatic repulsion between ionized side chains on the functional peptide segment. These cylindrical micelles formed by self-assembly can be viewed as fibrils or high-aspect-ratio nanostructures in which the functional peptide segment is repetitively displayed on the surface of the micelle.

The PAs of the present invention may be used to form biocompatible, biodegradable gels useful in the creation of scaffolds or templates, which may or may not include isolated cells, into a human patient to create or induce the body to create an organ or tissue equivalent. Such gels could promote cell engraftment and provide three-dimensional templates for new tissue growth. The resulting tissue is expected to be generally similar in composition and histology to naturally occurring tissue, in contrast to scar tissue that would generally result absent intervention during the body's natural healing process.

To that end, the present invention provides in one embodiment a self-assembling peptide-amphiphile solution than can be directly injected into a target site within a human patient, wherein the self-assembled peptide-amphiphile gel organizes into a fibrillar scaffold or matrix. In another embodiment, cells may be suspended in a self-assembled peptide-amphiphile gel that is pre-formed into a matrix outside the body, which then can be implanted into a human patient. Ultimately, the self-assembled peptide-amphiphile gel degrades, leaving only the resulting tissue. In yet another embodiment of the present invention, the peptide-amphiphiles of the present invention are used in conjunction with other tissue engineering materials, either as a gel, solid, or liquid and are used to template tissue growth in a pre-determined area on a patient.

It is a further object of the present invention to provide a fibrillar (or nanofibrous) scaffold of self-assembling peptide amphiphiles whose design and function is patterned after naturally occurring materials and tissues. For example, in one embodiment, the present invention provides for self-assembling peptide amphiphiles whose design and function is patterned after proteins involved in central nervous system development. [37, 50, 51]

One of skill in the art will readily recognize that a gel or solid comprised of these nanofibers under physiological conditions of pH, temperature and tonicity affords the opportunity to utilize this material for a wide range of purposes and in a number of different potential biomedical and tissue engineering applications.

In one embodiment, the present invention provides a method of treating a patient with tissue-engineered material that includes the step of administering a peptide amphiphile composition to a target site on the patient in need of a tissue engineered material. One particularly preferred utility for the peptide amphiphile molecules and the gels formed therefrom is in the field of nerve regeneration and spinal cord injury treatment. PA compositions are capable of stimulating neural progenitor cell differentiation and of inhibiting scar tissue formation by CNS cells. [37, 50, 51] PAs of the present invention may also find application in regulation, inhibition or promotion of axon outgrowth in neurons as well as the regulation, inhibition or promotion of cell-substrate adhesion among nerve cells.

It is a further object of the present invention to provide methods and compositions for altering (e.g., augmenting or stimulating) differentiation and growth of cells (e.g., neural progenitor cells and neurons). In particular, the present invention relates to compositions comprising one or more self-assembling peptide amphiphiles (e.g., in solution) that generate (e.g., self-assemble into) nanofibers that are able to encapsulate cells and promote cellular differentiation (e.g., neurite development) and methods of using the same. Compositions and methods of the present invention find use in research, clinical (e.g., therapeutic) and diagnostic settings.

This method of altering development of a neural progenitor cell includes contacting a neural progenitor cell, such as a stem cell, undeveloped neurite, neuron, or immortalized cell, with a composition comprising a peptide amphiphile, which alters the development of the neural progenitor cell. The altered development may include altered growth and/or differentiation of the neural progenitor cell. The altered development can include growth of the neural progenitor cell and/or axonal growth, which may comprise, for example, descending motor fiber growth or ascending sensory fiber growth. The altered development may also include differentiation of the neural progenitor cell. This may be accomplished by reducing astrogliosis by inhibiting the differentiation of the neural progenitor cells into astroglial cells.

The composition of the present invention for neural progenitor cell differentiation and/or growth comprises a peptide amphiphile of the present invention in an amount sufficient to alter development, as described above, and may further include other biologically compatible agents. For example, the composition may further comprise one or more other agents selected from the group consisting of a neurotrophic factor, an inhibitor of a neuronal growth inhibitor, a neuronal growth attractant and a neuronal growth inhibitor.

The site of altered development may occur at any site where altered development or growth of neural progenitor cells is required. For example, the peptide amphiphile composition may be directed through a lesion site or directed to the site of damaged nerve(s) under conditions sufficient for differentiation and/or growth of the neural cells. The damage nerve(s) may be present, for example, in a spinal cord. Alternatively, the damage site may be a damaged sensory neuron or motor neuron.

The composition may be administered in any manner suitable to direct the peptide amphiphile composition to the site of neural progenitor cell growth, including by intrathecal, intravenous, or parenteral administration of an aqueous solution comprising said peptide amphiphile.

It is a further object of the present invention to provide a method for treating a subject comprising the steps of: administering a composition comprising a peptide amphiphile to a subject with a damaged nerve or nerves, under conditions such that neuron growth occurs in the subject. The compositions of the present invention can promote axonal growth such as descending motor fiber growth or ascending sensory fiber growth. In some embodiments, the neuron growth comprises axonal growth at the site of the damaged nerve. In some embodiments, the neuron growth is accompanied by reduced astrogliosis and associated scar tissue formation in the subject. Preferably, the reduced astrogliosis and the reduced scar formation occur at the site of nerve damage. In some embodiments, the peptide amphiphile forms a nanofiber gel upon contact with the damaged tissue. The damaged nerve to be treated may be a nerve in a spinal cord that has been damaged, such as those damaged by traumatic spinal cord injury. In some embodiments, the damaged nerve comprises a damaged sensory neuron. In other embodiments, the damaged nerve comprises a damaged motor neuron. In some embodiments, neuron growth comprises regenerating development of a damaged neuron. The PA composition may be administered in any manner suitable to direct the composition to the site of the damaged nerve or nerves, but preferably is administered by intrathecal injection of an aqueous solution of the peptide amphiphile. In some embodiments, the composition comprising a peptide amphiphile is co-administered with one or more other agents.

It is a further object of the present invention to provide pharmaceutical compositions comprising one or more peptide amphiphiles, for example those comprising an IKVAV sequence (SEQ ID NO:5). See U.S. Patent Publication No. 2006-0247165 (Stupp et al.), the contents of which are incorporated by reference herein.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Example 1

Automated Synthesis and Purification of Peptide Amphiphiles Containing the Functional Peptide Segment $X_n$IKVAV (SEQ ID NO:23)

1.1 Reagents:

The following reagents, or equivalents, were used as received: HBTU (2-(1H-Benzotriazol-1-yl)-1,1,3,3-tetramethyluronium hexafluorophosphate), piperidine, DIEA (n, n,-diisopropylethlamine), DMF (n, n-dimethylformamide), DCM (dichloromethane), TFA (trifluoroacetic acid), TIS (triisopropylsilane). All water was purified by reverse osmosis and filtered using a Millipore™ system to a resistivity of 18.2 Mohm-cm. 9-Fluorenylmethoxycarbonyl (Fmoc) protected amino acids were purchased from EMD Biosciences (La Jolla, Calif.). Peptides were synthesized on low-loading Fmoc-Val-Wang resin (ca. 0.2-0.3 mmole/g) to improve overall yield of the target peptide. Fmoc-Leu-Ser($\psi^{Me,Me}$pro)-OH (termed 'pseudoproline') was used to increase the coupling efficiency of Ser-Leu-Ser-portion of the peptide.

1.2 Peptide Synthesis:

Peptides were synthesized via solid-phase methodology on an automated peptide synthesizer (CS Bio Co. model 136XT), using a 250 mL glass reaction vessel which was inverted 180° every two seconds for the duration of each reaction step, in order to fully expose the resin to each reagent. The resin was first swelled in DCM and DMF, and then Fmoc deprotection was performed with 30 vol % piperidine in DMF solution for 10 min, repeated twice. Amino acid couplings were done with 4.0 equivalents of the Fmoc-protected amino acid (0.5 M in DMF), 3.8 equivalents HBTU (0.475 M in DMF) and 6.0 equivalents of DIEA (0.75 M in DMF) for 3 h per coupling. Each solution was combined and pre-activated by bubbling with high purity nitrogen gas for 3 minutes prior to being added to the resin-containing reaction vessel. Each coupling was repeated twice to improve yield of the target peptide sequence, except for the alanine closest to the N-terminus and the adjacent leucine in the structural peptide, for which the couplings were repeated three times. Acetylation of any unreacted free amines (after the coupling steps) was done with 10 vol % acetic anhydride in DMF for 5 minutes, repeated three times. For a 2 mmole reaction scale, 55 mL of solution was used for each deprotection, acetylation and washing step. All reagents were stored and reactions performed under high purity nitrogen gas. Multiple DCM and DMF washing steps were done between each reaction step. After the peptide portion of the molecule is prepared, the N-terminus of the peptide was capped with palmitic acid using 2.0 equivalents of the fatty acid, 1.9 equivalents of HBTU and 3.0 equivalents of DIEA in DMF. This reaction was allowed to proceed for 2 h and was repeated at least three times, after which the product was checked for free amines by the ninhydrin reaction (also known as the 'Kaiser test') and the capping repeated if necessary to obtain a negative result for free amines.

1.3 Resin Cleavage:

Peptide-loaded resin was transferred to a 200 mL glass shaker vessel, where cleavage and deprotection from the resin was carried out with ca. 50 mL of a mixture of TFA:TIS:water in ratio of 95.0:2.5:2.5 for 3 hours. The peptide amphiphile solution was then decanted into a round-bottom flask and the TFA removed by rotary evaporation while heating the solution to 40° C., using a collector at −78° C. (dry ice/isopropanol) and an ultimate pressure of ca. 20 mtorr. Rotary evaporation was halted prior to complete dryness, and the remaining viscous peptide solution (typically <1 mL) triturated with ca. 200 mL of cold (−20° C.) diethyl ether. The solution was agitated to ensure good mixing of then re-cooled to −20° C. overnight to allow complete precipitation. The resulting precipitated peptide amphiphile was collected in a medium fritted glass funnel, washed three times with cold ether (ca. 200 mL) and dried under vacuum (<20 in. Hg).

Figure 2A:
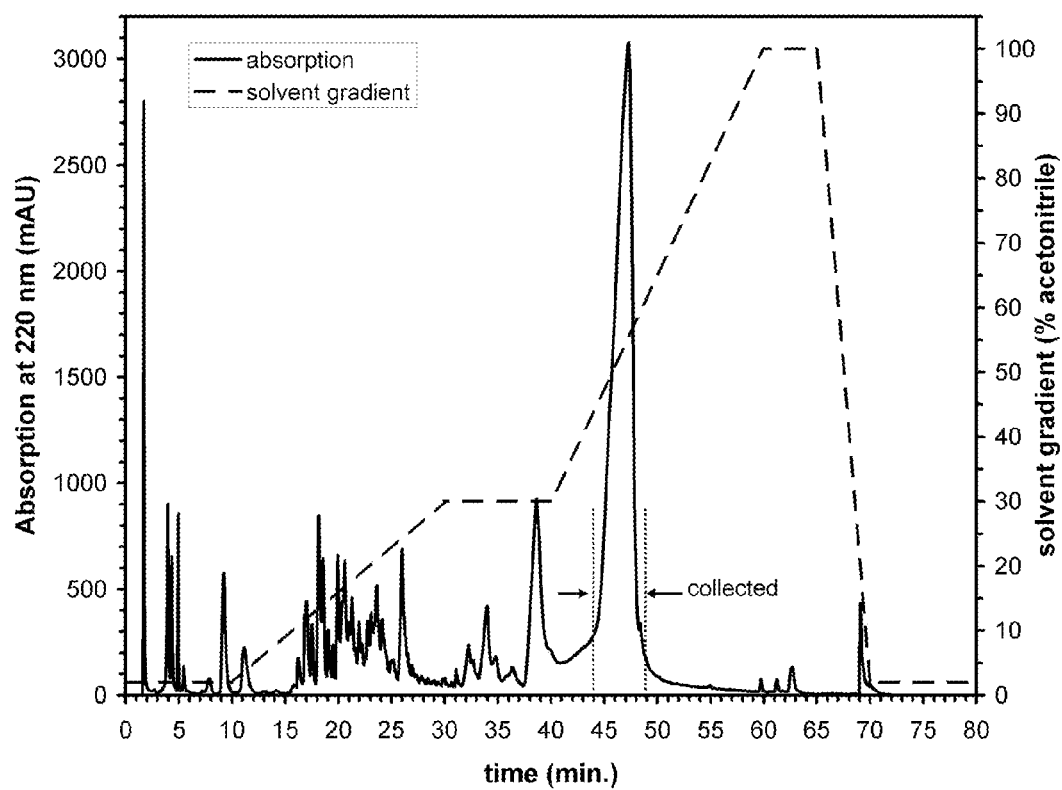
FIG. 2A depicts the results of preparative-scale high pressure liquid chromatography (HPLC) of crude (or as-synthesized) peptide amphiphile (SEQ ID NO:2). This figure shows the HPLC purification of SEQ ID NO:2 as depicted by the 220 nm UV absorption trace (solid line), the solvent gradient (dashed line, corresponding to % acetonitrile in water) and the portion of purified material collected during separation (between dotted lines).
Figure 2B:
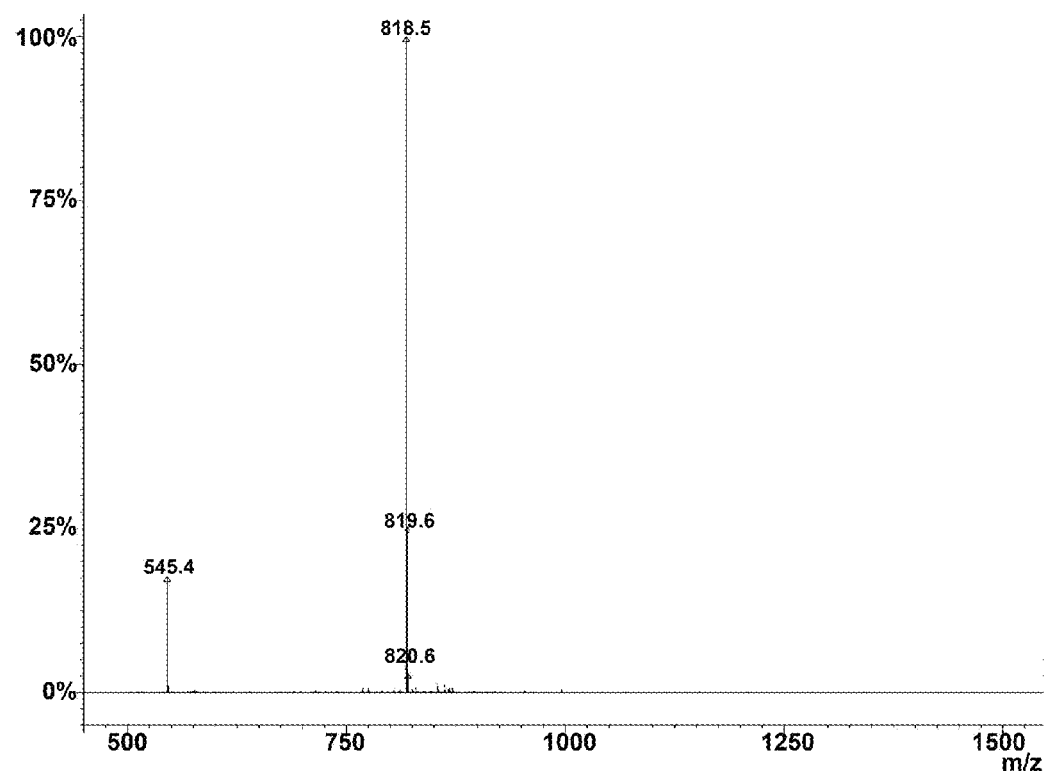
FIG. 2B depicts the electrospray ionization mass spectroscopy, negative ion mode (ESI-MS) of purified SEQ ID NO:2.
Figure 2C:
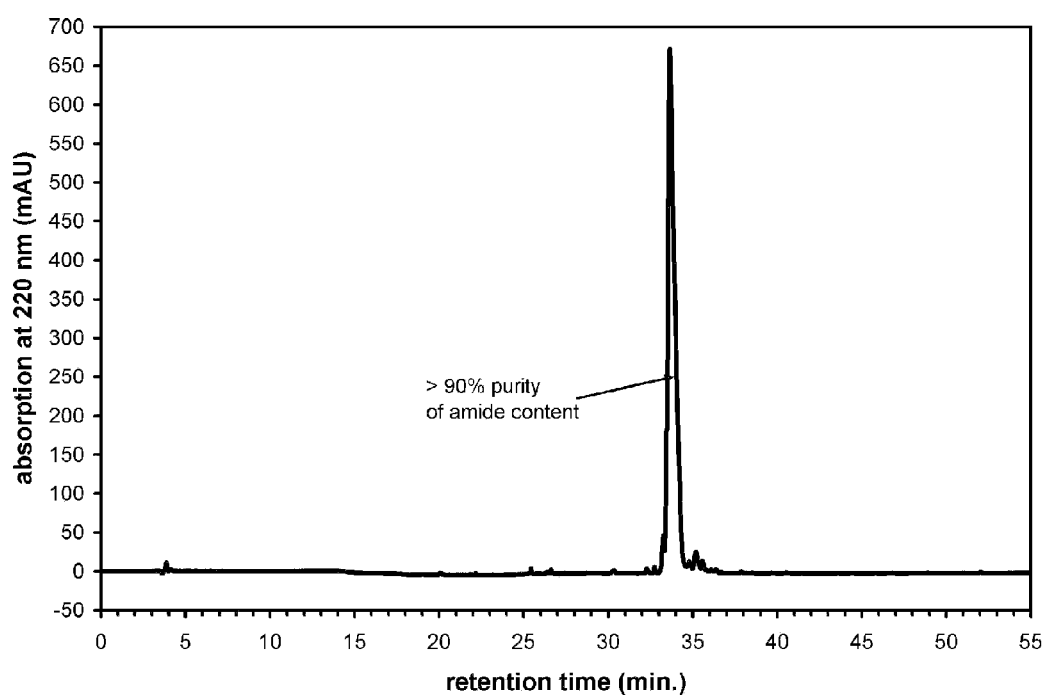
FIGS. 2C and 2D show the analytical-scale high pressure liquid chromatography (HPLC) of purified SEQ ID NO:2 and SEQ ID NO:4, respectively.

1.4 Purification:

SEQ ID NO:2 or SEQ ID NO:4 was dissolved at 20 mg/mL in an aqueous solution with sufficient ammoniumhydroxide to obtain a pH of 9. This solution was purified in 5 mL aliquots using an Agilent, Inc. model 1100 preparative HPLC equipped with a Phenomenex, Inc. Gemini® 5 μm C18 column (100×30 mm). An elution gradient of water and acetonitrile (each containing 0.1 vol % ammonium hydroxide buffer) was used, as shown in FIG. 2A. The flow rate was 15 mL/min, and the mobile phase was pre-heated to ca. 45° C. using a Timberline Instruments TL-105 column heater. UV-absorption was monitored at 220 nm wavelength, and the eluent collected as shown in FIG. 2A. Similar purification attempts with SEQ ID NO:6 were unsuccessful due to the relatively low solubility of this peptide amphiphile in the aqueous buffer employed.

1.5 Lyophilization:

To remove the water and acetonitrile following preparative HPLC, peptide amphiphile solutions were transferred to a glass lyophilization flask, shell frozen in a dry ice/isopropanol bath at −78° C., and lyophilized for at least 48 hrs on a freeze-dryer operating at a collector temperature of −80° C. and a pressure of <0.100 mbar. Typical yields of purified peptide amphiphile were 30-40% of theoretical yield, with a typical 2 mmole reaction scale yielding circa 1.0 g of material with a peptide purity of >95%.

1.6 pH Adjustment:

The lyophilized peptide amphiphile powder was weighed and re-dissolved in USP pharmaceutical grade water at a concentration of 5 mg/mL. The colloidal suspension obtained was agitated in an ultrasonic bath for 30 min. A solution of 1 M sodium hydroxide (NaOH), prepared from USP pharmaceutical grade NaOH and water, was filtered through a sterile 0.2 micron PTFE syringe filter. pH of the suspension was adjusted by the addition of small aliquots of the NaOH solution to a range of pH 7.0-7.5, causing the SEQ ID NO:2 or SEQ ID NO:4 molecule to go readily into solution.

1.7 Aseptic Filtration and Vial Filling:

The pH adjusted peptide amphiphile solution was filtered through a sterile, 25-mm polyethersulfone low-protein-binding membrane (Pall Life Sciences Acrodisc® Supor® 0.8/0.2 micron, or equivalent) into sterile, pre-cleaned glass serum vials. Vials were capped with lyophilization stoppers, frozen and immediately transferred to a freeze-dryer and lyophilized as described above. After 48 hr the vials were back-filled with high purity nitrogen gas filtered through a 0.2 micron PTFE filter and stoppered in situ. Once the vials were removed from the freeze-drying chamber the aluminum caps were crimp-sealed, and vials were stored at −20° C. until use.

Example 2

Comparison of Solubility and Rheological Properties of SEQ ID NO:2, SEQ ID NO:4, and SEQ ID NO:6

The structures of the three peptide amphiphiles examined in detail herein are as follows:

SEQ ID NO: 2:
$C_{16}H_{31}O$-Ser-Leu-Ser-Leu-Ala-Ala-Ala-Glu-Glu-Ile-

Lys-Val-Ala-Val-OH

SEQ ID NO: 4:
$C_{16}H_{31}O$-Ser-Leu-Ser-Leu-Ala-Ala-Ala-Asp-Ile-Lys-

Val-Ala-Val-OH

SEQ ID NO: 6:
$C_{16}H_{31}O$-Ser-Leu-Ser-Leu-Ala-Ala-Ala-Glu-Ile-Lys-

Val-Ala-Val-OH

Chemical structures for these molecules are also depicted in FIG. 1. Experiments were performed to examine the gelation kinetics and rheological properties of SEQ ID NO:2 with SEQ ID NO:6. Peptide amphiphile samples were dissolved in water at a concentration of 10 mg/mL. Then 0.125 mL of the solution was mixed with an equal volume of artificial cerebrospinal fluid (CSF).[29-31] The artificial CSF was formulated to exhibit the normal physiological pH, tonicity and salt concentrations present in tissues of the human spinal cord. This artificial CSF was found to induce self-assembly of the peptide amphiphile SEQ ID NO:2, resulting in a gel with the desired properties.

Figure 3:
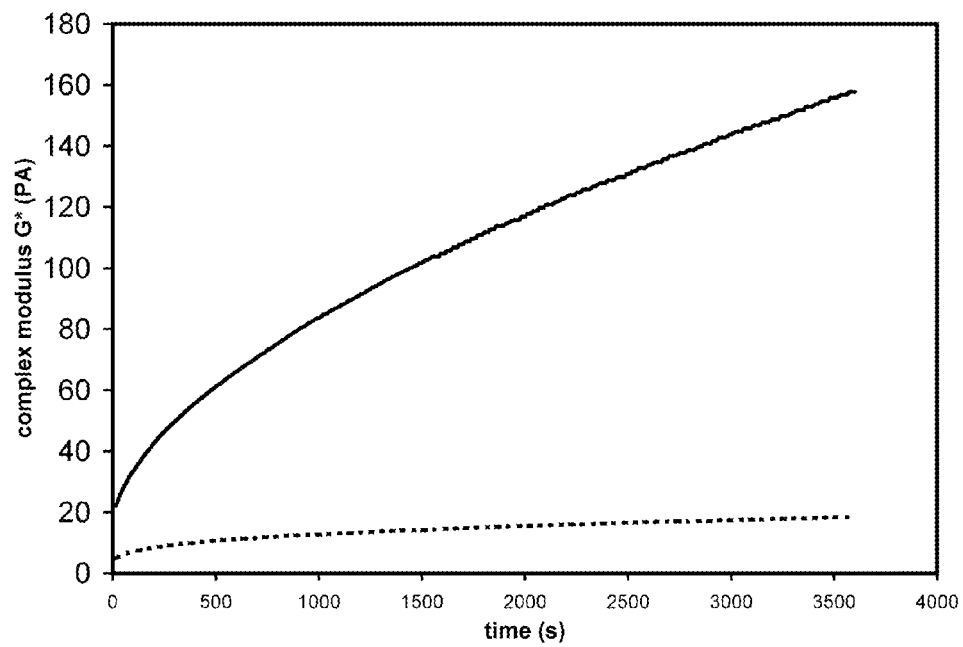
FIG. 3 depicts the results of assays comparing the gelation kinetics and rheological properties of SEQ ID NO:2 and SEQ ID NO:6.
Figure 3:
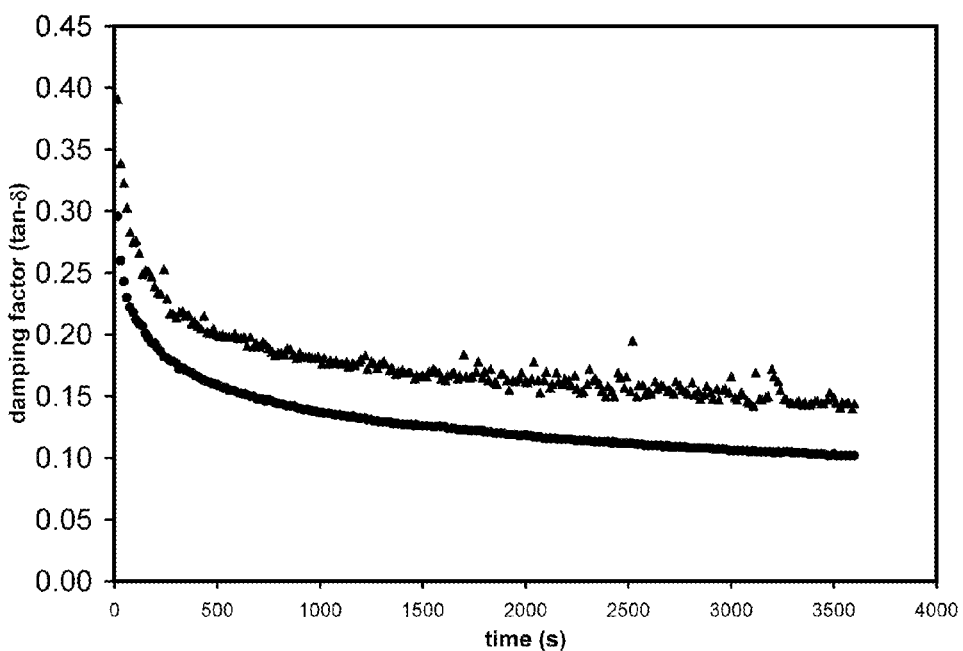

A Physica, Inc. MCR 300 Molecular Compact Rheometer equipped with a 25 mm plate was used to measure stiffness of gels formed by SEQ ID NO:2 and SEQ ID NO:6 in vitro. Samples were measured at 21° C., 0.5% shear strain, with a frequency ($\omega$) of 10 Hz and a gap between the plates of 0.5 mm. G' (storage modulus) and G' (loss modulus) were measured with respect to time post-gelation. The complex shear modulus (G*) (defined as the shear stress divided by the shear strain) of SEQ ID NO:2 was found to be an order of magnitude greater that that for SEQ ID NO:6 at one hour post-gelation. See FIG. 3A.

Tan($\delta$) (defined as the loss modulus divided by the storage modulus) quantifies the balance between energy loss and energy storage in a material, regardless of viscosity. A significantly lower value of tan($\delta$) was obtained for SEQ ID NO:2, indicating more "gel-like" properties, compared to more "liquid-like" behavior for SEQ ID NO:6 in the artificial cerebrospinal fluid. See FIG. 3B.

While the amino acid sequence change between SEQ ID NO:2 and SEQ ID NO:6 appears at first glance to be relatively minor, it nevertheless confers several important and unexpected consequences. The additional glutamic acid residue increases the aqueous solubility and broadens the type of aqueous buffers in which the molecule is soluble. Absent this modification, the only amino acid side chains that are ionized under physiological conditions in SEQ ID NO:6 form a zwitterion (e.g. Glu-Ile-Lys), which limits the molecule's solubility in most aqueous buffers. For example, SEQ ID NO:2 is soluble in a 0.1 vol % ammonium hydroxide buffer at a concentration of 20 mg/mL, whereas SEQ ID NO:6 is only sparingly soluble in this buffer. This change has important implications for the manufacturability and clinical development of the peptide amphiphile, as solubility in an ammonium hydroxide buffer greatly facilitates purification by HPLC.

Figure 2D:
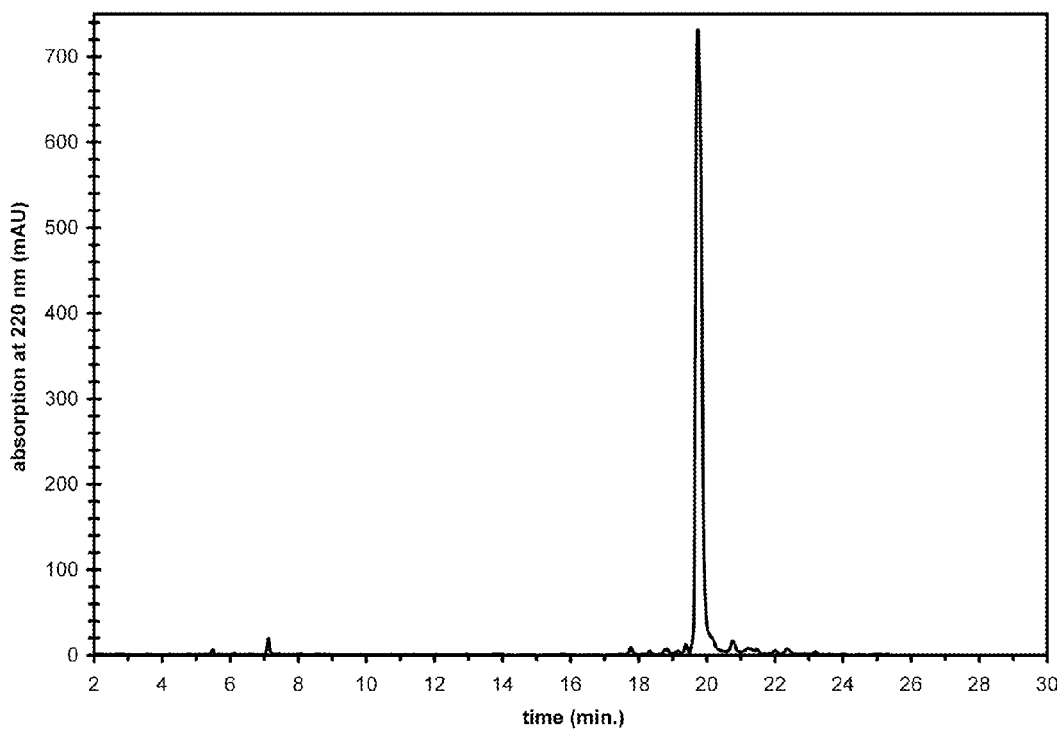

The influence of zwitterion or salt-bridge formation between the carboxylic acid and amine side-chains on the solubility of SEQ ID NO:6 is further demonstrated by replacing the single glutamic acid in SEQ ID NO:6 with an aspartic acid (Asp) (SEQ ID NO:4). This seemingly insignificant modification (the deletion of one methylene group from the residue) results in a greater than 20-fold increase in aqueous solubility of the peptide amphiphile in an ammonium hydroxide buffer, greatly facilitating purification by HPLC (see FIG. 2D).

In addition, the increased stiffness of the gel formed by SEQ ID NO:2 in artificial cerebrospinal fluid better mimics the mechanical properties of natural central nervous system (brain and spinal cord) tissue, which has an elastic modulus of 100-1000 Pa.[32]

These significant and unanticipated changes in properties emphasize the importance of amino acid sequence selection in the design of peptide amphiphiles for tissue engineering applications. The results also highlight the difficulty in predicting solubility, kinetic and macroscopic mechanical properties a priori from the amino acid sequence alone. Importantly, the improvements in solubility and gel stiffness obtained with the SEQ ID NO:2 and SEQ ID NO:4 peptide amphiphile were achieved while retaining the three principle elements of the original SEQ ID NO:6 structure: the palmitoyl lipophilic segment, the beta-sheet forming structural segment SLSLAAA (SEQ ID NO:21) and the functional C-terminal segment IKVAV (SEQ ID NO:5). Thus, the nanoscale morphology of the self-assembled gel and its biological activity are anticipated to be similar if not improved.

INDUSTRIAL APPLICABILITY

The peptide amphiphile compositions described herein possess unexpectedly superior gelation kinetics and rheological properties, for example an improved solubility which, in turn, facilitates the realization of the elevated degree of purity necessary for pharmaceutical applications, for example for in vivo administration to human patients. In addition, gels of the improved peptide amphiphile compositions of the present invention formed in CSF possess an increased mechanical stiffness which better mimics the mechanical properties of tissues in the natural central nervous system, which, in turn, correlates to improved neurogenic differentiation of mesenchymal stem cells.

REFERENCES

1. Stendahl, J. C.; M. S. Rao; M. O. Guler; S. I. Stupp "Intermolecular forces in the self-assembly of peptide amphiphile nanofibers" *Adv. Func. Mater.* 2006, 16, 499-508.
2. Tovar, J. D.; R. C. Claussen; S. I. Stupp "Probing the interior of peptide amphiphile supramolecular aggregates" *J. Am. Chem. Soc.* 2005, 127 (20), 7337-45.
3. Fields, G. B. "Induction of protein-like molecular architecture by self-assembly processes" *Bioorg. Med. Chem.* 1999, 7 (1), 75-81.
4. Yu, Y. C.; M. Tirrell; G. B. Fields "Minimal lipidation stabilizes protein-like molecular architecture" *J. Am. Chem. Soc.* 1998, 120 (39), 9979-87.
5. Fields, G. B.; J. L. Lauer; Y. Dori; P. Forms; Y. C. Yu; M. Tirrell "Proteinlike molecular architecture: Biomaterial applications for inducing cellular receptor binding and signal transduction" *Biopolymers* 1998, 47 (2), 143-51.
6. Yu, Y. C.; P. Berndt; M. Tirrell; G. B. Fields "Self-assembling amphiphiles for construction of protein molecular architecture" *J. Am. Chem. Soc.* 1996, 118 (50), 12515-20.
7. Paramonov, S. E.; H. W. Jun; J. D. Hartgerink "Self-assembly of peptide-amphiphile nanofibers: The roles of hydrogen bonding and amphiphilic packing" *J. Am. Chem. Soc.* 2006, 128 (22), 7291-98.
8. de Loos, M.; B. L. Fering a; J. H. van Esch "Design and application of self-assembled low molecular weight hydrogels" *Eur. J. Org. Chem.* 2005, (17), 3615-31.
9. Forms, P.; J. L. Lauer-Fields; S. Gao; G. B. Fields "Induction of protein-like molecular architecture by monoalkyl hydrocarbon chains" *Biopolymers* 2000, 54 (7), 531-46.
10. Avrahami, D.; Y. Shai "Conjugation of a magainin analogue with lipophilic acids controls hydrophobicity, solution assembly, and cell selectivity" *Biochemistry* 2002, 41 (7), 2254-63.
11. Mardilovich, A.; J. A. Craig; M. Q. McCammon; A. Garg; E. Kokkoli "Design of a novel fibronectin-mimetic peptide-amphiphile for functionalized biomaterials" *Langmuir* 2006, 22 (7), 3259-64.
12. McGregor, C. L.; L. Chen; N. C. Pomroy; P. Hwang; S. Go; A. Chakrabartty; G. G. Prive "Lipopeptide detergents designed for the structural study of membrane proteins" *Nat. Biotechnol.* 2003, 21 (2), 171-76.
13. Harrington, D. A.; E. Y. Cheng; M. O. Guler; L. K. Lee; J. L. Donovan; R. C. Claussen; S. I. Stupp "Branched peptide-amphiphiles as self-assembling coatings for tissue engineering scaffolds" *J. Biomed. Mater. Res. Part A* 2006, 78A (1), 157-67.
14. Rajangam, K.; H. A. Behanna; M. J. Hui; X. Q. Han; J. F. Hulvat; J. W. Lomasney; S. I. Stupp "Heparin binding nanostructures to promote growth of blood vessels" *Nano Lett.* 2006, 6 (9), 2086-90.
15. Guler, M. O.; L. Hsu; S. Soukasene; D. A. Harrington; J. F. Hulvat; S. I. Stupp "Presentation of rgds epitopes on self-assembled nanofibers of branched peptide amphiphiles" *Biomacromolecules* 2006, 7 (6), 1855-63.
16. Guler, M. O.; S. Soukasene; J. F. Hulvat; S. I. Stupp "Presentation and recognition of biotin on nanofibers formed by branched peptide amphiphiles" *Nano Lett.* 2005, 5 (2), 249-52.
17. Guler, M. O.; J. K. Pokorski; D. H. Appella; S. I. Stupp "Enhanced oligonucleotide binding to self-assembled nanofibers" *Bioconjugate Chem.* 2005, 16 (3), 501-03.
18. Guler, M. O.; R. C. Claussen; S. I. Stupp "Encapsulation of pyrene within self-assembled peptide amphiphile nanofibers" *J. Mater. Chem.* 2005, 15 (42), 4507-12.
19. Bull, S. R.; M. O. Guler; R. E. Bras; P. N. Venkatasubramanian; S. I. Stupp; T. J. Meade "Magnetic resonance imaging of self-assembled biomaterial scaffolds" *Bioconjugate Chem.* 2005, 16 (6), 1343-48.

20. Bull, S. R.; M. O. Guler; R. E. Bras; T. J. Meade; S. I. Stupp "Self-assembled peptide amphiphile nanofibers conjugated to mri contrast agents" *Nano Lett.* 2005, 5 (1), 1-4.
21. Beniash, E.; J. D. Hartgerink; H. Storrie; S. I. Stupp "Self-assembling peptide amphiphile nanofiber matrices for cell entrapment" *Acta Biomaterialia* 2005, 1 (4), 387-97.
22. Hosseinkhani, H.; M. Hosseinkhani; A. Khademhosseini; H. Kobayashi; Y. Tabata "Enhanced angiogenesis through controlled release of basic fibroblast growth factor from peptide amphiphile for tissue regeneration" *Biomaterials* 2006, 27 (34), 5836-44.
23. Hosseinkhani, H.; M. Hosseinkhani; H. Kobayashi "Design of tissue-engineered nanoscaffold through self-assembly of peptide amphiphile" *J. Bioact. Compat. Polym.* 2006, 21 (4), 277-96.
24. Bitton, R.; J. Schmidt; M. Biesalski; R. Tu; M. Tirrell; H. Bianco-Peled "Self-assembly of model DNA-binding peptide amphiphiles" *Langmuir* 2005, 21 (25), 11888-95.
25. Brunsveld, L.; J. Kuhlmann; H. Waldmann "Synthesis of palmitoylated ras-peptides and -proteins" *Methods* 2006, 40 (2), 151-65.
26. Smith, L. A.; P. X. Ma "Nano-fibrous scaffolds for tissue engineering" *Colloid Surf. B-Biointerfaces* 2004, 39 (3), 125-31.
27. Behanna, H. A.; J. J. J. M. Donners; A. C. Gordon; S. I. Stupp "Coassembly of amphiphiles with opposite peptide polarities into nanofibers" *J. Am. Chem. Soc.* 2005, 127 (4), 1193-200.
28. Niece, K. L.; J. D. Hartgerink; J. J. J. M. Donners; S. I. Stupp "Self-assembly combining two bioactive peptide-amphiphile molecules into nanofibers by electrostatic attraction" *J. Am. Chem. Soc.* 2003, 125 (24), 7146-47.
29. Ohmori, H.; Y. Sato; A. Namiki "The anticonvulsant action of propofol on epileptiform activity in rat hippocampal slices" *Anesth. Analg.* 2004, 99 (4), 1095-101.
30. Shahraki, A.; T. W. Stone "Blockade of presynaptic adenosine a1 receptor responses by nitric oxide and superoxide in rat hippocampus" *Eur. J. Neurosci.* 2004, 20 (3), 719-28.
31. Oka, K.; M. Yamamoto; T. Nonaka; M. Tomonaga "The significance of artificial cerebrospinal fluid as perfusate and endoneurosurgery" *Neurosurgery* 1996, 38 (4), 733-36.
32. Engler, A. J.; S. Sen; H. L. Sweeney; D. E. Discher "Matrix elasticity directs stem cell lineage specification" *Cell* 2006, 126 (4), 677-89.
33. Hartgerink, J. D.; E. Beniash; S. I. Stupp "Self-assembly and mineralization of peptide-amphiphile nanofibers" *Science* 2001, 294 (5547), 1684-88.
34. Hartgerink, J. D.; E. Beniash; S. I. Stupp "Peptide-amphiphile nanofibers: A versatile scaffold for the preparation of self-assembling materials" *Proc. Natl. Acad. Sci. U.S.A.* 2002, 99 (8), 5133-38.
35. Behanna, H. A.; K. Rajangam; S. I. Stupp "Modulation of fluorescence through coassembly of molecules in organic nanostructures" *J. Am. Chem. Soc.* 2007, 129 (2), 321-27.
36. Arnold, M. S.; M. O. Guler; M. C. Hersam; S. I. Stupp "Encapsulation of carbon nanotubes by self-assembling peptide amphiphiles" *Langmuir* 2005, 21 (10), 4705-09.
37. Silva, G. A.; C. Czeisler; K. L. Niece; E. Beniash; D. A. Harrington; J. A. Kessler; S. I. Stupp "Selective differentiation of neural progenitor cells by high-epitope density nanofibers" *Science* 2004, 303 (5662), 1352-55.
38. Dori, Y.; H. Bianco-Peled; S. K. Satija; G. B. Fields; J. B. McCarthy; M. Tirrell "Ligand accessibility as means to control cell response to bioactive bilayer membranes" *J. Biomed. Mater. Res.* 2000, 50 (1), 75-81.
39. Berndt, P.; G. B. Fields; M. Tirrell "Synthetic lipidation of peptides and amino acids: Monolayer structure and properties" *J. Am. Chem. Soc.* 1995, 117, 9515-22.
40. Meijer, J. T.; M. Roeters; V. Viola; D. Lowik; G. Vriend; J. C. M. van Hest "Stabilization of peptide fibrils by hydrophobic interaction" *Langmuir* 2007, 23 (4), 2058-63.
41. Jun, H. W.; V. Yuwono; S. E. Paramonov; J. D. Hartgerink "Enzyme-mediated degradation of peptide-amphiphile nanofiber networks" *Adv. Mater.* 2005, 17 (21), 2612-+.
42. Kokkoli, E.; A. Mardilovich; A. Wedekind; E. L. Rexeisen; A. Garg; J. A. Craig "Self-assembly and applications of biomimetic and bioactive peptide-amphiphiles" *Soft Matter* 2006, 2 (12), 1015-24.
43. Malkar, N. B.; J. L. Lauer-Fields; D. Juska; G. B. Fields "Characterization of peptide-amphiphiles possessing cellular activation sequences" *Biomacromolecules* 2003, 4 (3), 518-28.
44. Sone, E. D.; S. I. Stupp "Semiconductor-encapsulated peptide-amphiphile nanofibers" *J. Am. Chem. Soc.* 2004, 126 (40), 12756-57.
45. Yu, Y. C.; V. Roontga; V. A. Daragan; K. H. Mayo; M. Tirrell; G. B. Fields "Structure and dynamics of peptide-amphiphiles incorporating triple-helical protein-like molecular architecture" *Biochemistry* 1999, 38 (5), 1659-68.
46. Tsonchev, S.; A. Troisi; G. C. Schatz; M. A. Ratner "All-atom numerical studies of self-assembly of zwitterionic peptide amphiphiles" *J. Phys. Chem. B* 2004, 108 (39), 15278-84.
47. Tsonchev, S.; G. C. Schatz; M. A. Ratner "Electrostatically-directed self-assembly of cylindrical peptide amphiphile nanostructures" *J. Phys. Chem. B* 2004, 108 (26), 8817-22.
48. Tsonchev, S.; A. Troisi; G. C. Schatz; M. A. Ratner "On the structure and stability of self-assembled zwitterionic peptide amphiphiles: A theoretical study" *Nano Lett.* 2004, 4 (3), 427-31.
49. Solis, F. J.; S. I. Stupp; M. O. de la Cruz "Charge induced pattern formation on surfaces: Segregation in cylindrical micelles of cationic-anionic peptide-amphiphiles" *J. Chem. Phys.* 2005, 122 (5), 054905.
50. Silva, G. A. "Small neuroscience: The nanostructure of the central nervous system and emerging nanotechnology applications" *Curr. Nanosci.* 2005, 1 (3), 225-36.
51. Silva, G. A. "Nanotechnology approaches for the regeneration and neuroprotection of the central nervous system" *Surg. Neurol.* 2005, 63 (4), 301-06.
52. Nomizu, M.; A. Utani; N. Shiraishi; M. C. Kibbey; Y. Yamada; P. P. Roller "The all-d-configuration segment containing the ikvav sequence of laminin a-chain has similar activities to the all-1-peptide invitro and invivo" *J. Biol. Chem.* 1992, 267 (20), 14118-21.
53. Yamada, M.; Y. Kadoya; S. Kasai; K. Kato; M. Mochizuki; N. Nishi; N. Watanabe; H. K. Kleinman; Y. Yamada; M. Nomizu "Ile-lys-val-ala-val (ikvav)-containing laminin alpha 1 chain peptides form amyloid-like fibrils" *FEBS Lett.* 2002, 530 (1-3), 48-52.
54. Kibbey, M. C.; M. Jucker; B. S. Weeks; R. L. Neve; W. E. Vannostrand; H. K. Kleinman "Beta-amyloid precursor protein binds to the neurite-promoting ikvav site of laminin" *Proc. Natl. Acad. Sci. U.S.A.* 1993, 90 (21), 10150-53.

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. For instance, various peptide amphiphiles have been described in conjunction with specific amino acid residues; however, other residues can be used herewith to promote a particular tissue growth and regeneration on the nanostructures prepared therefrom. Likewise, while the present invention has been described as applicable to biomedical or tissue engineering use, other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed is:

1. A molecule having one of the following structures: $C_{15}H_{31}C(O)$-Ser-Leu-Ser-Leu-Ala-Ala-Ala-Glu-Glu-Ile-Lys-Val-Ala-Val-OH (SEQ ID NO:2) or $C_{15}H_{31}C(O)$-Ser-Leu-Ser-Leu-Ala-Ala-Ala-Asp-Ile-Lys-Val-Ala-Val-OH (SEQ ID NO:4).

2. A method of treating nerve damage in a subject in need thereof comprising administering to said subject a composition comprising the molecule of claim 1.

3. The method of claim 2, wherein the damaged nerve is a nerve in the spinal cord of said subject.

4. The method of claim 2, wherein the damaged nerve comprises a sensory neuron.

5. The method of claim 2, wherein the damaged nerve comprises a motor neuron.

6. The method of claim 2, wherein said composition is administered intrathecally.

7. The method of claim 6, wherein said composition is an aqueous solution comprising said molecule.

8. The method of claim 7, wherein said molecule forms a nanofiber gel in the subject.

9. The method of claim 8, wherein the nanofiber gel forms upon contact with the damaged nerve.

10. The method of claim 2, wherein said composition further comprises one or more other agents selected from the group consisting of a neurotrophic factor, an inhibitor of a neuronal growth inhibitor, a neuronal growth attractant and a neuronal growth inhibitor.

11. A peptide amphiphile molecule that is soluble in aqueous media and affords a gel under physiological conditions, said peptide amphiphile molecule comprising:
(a) a lipophilic segment selected from the group consisting of a single, linear moiety of the formula $C_{n-1}H_{2n-1}C(O)$—, wherein n=6-22, linked to the N-terminus of the peptide via a peptidyl bond;
(b) a structural peptide segment intermediate to the peptide amphiphile molecule, comprising 3-8 amino acid residues with non-polar side chains, having a propensity for predominantly beta-sheet secondary structure formation; and
(c) a C-terminal, functional peptide segment selected from any one of SEQ ID NOs:24-26, and $(Xaa)_m$-Val-Ala-Val-Lys-Ile-$(Xbb)_p$ (SEQ ID NO:28), where m=1 to 5, p=0 to 3, Xaa is selected from the group consisting of aminomalonic acid (Ama), aspartic acid (Asp), aminoadipic acid (Aib), aminoheptanedioic acid (Apm) and gammacarboxyglutamic acid (Gla), and Xbb is selected from any amino acid.

12. The peptide amphiphile molecule of claim 11, wherein the lipophilic segment comprises palmitic acid.

13. The peptide amphiphile molecule of claim 11, wherein the structural peptide segment is selected from the group consisting of SEQ ID NOs:8-21.

14. The peptide amphiphile molecule of claim 11, wherein the C-terminal functional peptide segment is SEQ ID NO:24.

15. The peptide amphiphile molecule of claim 11, wherein the C-terminal functional peptide segment is SEQ ID NO:25.

16. The peptide amphiphile molecule of claim 11, wherein the C-terminal functional peptide segment is SEQ ID NO:26.

17. The peptide amphiphile molecule of claim 11, wherein the C-terminal functional peptide segment is $(Xaa)_m$-Val-Ala-Val-Lys-Ile-$(Xbb)_p$ (SEQ ID NO:28), where m=1 to 5, p=0 to 3, Xaa is selected from the group consisting of aminomalonic acid (Ama), aspartic acid (Asp), aminoadipic acid (Aib), aminoheptanedioic acid (Apm) and gammacarboxyglutamic acid (Gla), and Xbb is selected from any amino acid.

18. A composition comprising one or more molecules of claim 1 or peptide amphiphile molecules of claim 11 self-assembled to form one or more fibrillar structures.

19. The composition of claim 18, wherein said fibrillar structures are cylindrical micelles.

20. A substrate having the composition of claim 18 coated thereon.

21. A biocompatible, biodegradable gel comprising the molecules of claim 1 or peptide amphiphile molecules of claim 11, said gel serving as a scaffold for tissue growth.

22. A biocompatible, biodegradable gel comprising the fibrillar structures of claim 18, said gel serving as a scaffold for tissue growth.

23. A matrix or scaffold comprising the composition of claim 18.

24. A pharmaceutical composition comprising one or more claim 1 or peptide amphiphile molecules of claim 11 in conjunction with a pharmaceutically acceptable carrier.

25. A method of treating a human subject suffering nerve damage comprising the step of administering a composition comprising the peptide amphiphile molecule having the following structure: $C_{15}H_{31}C(O)$-Ser-Leu-Ser-Leu-Ala-Ala-Ala-Glu-Glu-Ile-Lys-Val-Ala-Val-OH (SEQ ID NO:2) under conditions that stimulate neuron regeneration.

26. A method of treating a human subject suffering nerve damage comprising the step of administering a composition comprising the peptide amphiphile molecule having the following structure: $C_{15}H_{31}C(O)$-Ser-Leu-Ser-Leu-Ala-Ala-Ala-Asp-Ile-Lys-Val-Ala-Val-OH (SEQ ID NO:4) under conditions that stimulate neuron regeneration.

27. A method of making a peptide amphiphile molecule, as described in claim 11, wherein solid phase peptide synthesis is performed using a polymeric resin support that is pre-loaded with a protected amino acid at a loading fraction of 0.1-0.4 mmole/g, said loading fraction selected to improve synthetic yield of the peptide for use in the peptide amphiphile molecule.

28. A method of making a peptide amphiphile molecule, as described in claim 11, wherein a serine amino acid residue is incorporated into the peptide sequence in the form of a pseudoproline (oxazolidine) dipeptide, said method selected to improve the synthetic yield of the peptide for use in the peptide amphiphile molecule.

* * * * *